United States Patent
Ryan et al.

(10) Patent No.: US 10,315,994 B2
(45) Date of Patent: Jun. 11, 2019

(54) PHOTOSTABLE COMPOUNDS, ABSORBING COMPOUNDS AND USES THEREOF

(71) Applicant: Commonwealth Scientific and Industrial Research Organisation, Acton (AU)

(72) Inventors: John Ryan, Clayton (AU); Mark York, Clayton (AU)

(73) Assignee: Commomwealth Scientific and Industrial Research Organization, Acton (AU)

( * ) Notice: Subject to any disclaimer, the term of this patent is extended or adjusted under 35 U.S.C. 154(b) by 0 days.

(21) Appl. No.: 15/518,743

(22) PCT Filed: Nov. 28, 2016

(86) PCT No.: PCT/AU2016/051162
§ 371 (c)(1),
(2) Date: Apr. 12, 2017

(87) PCT Pub. No.: WO2017/088031
PCT Pub. Date: Jun. 1, 2017

(65) Prior Publication Data
US 2018/0016233 A1  Jan. 18, 2018

(30) Foreign Application Priority Data
Nov. 27, 2015 (AU) .................. 2015904932

(51) Int. Cl.
| | |
|---|---|
| *C07D 211/70* | (2006.01) |
| *C07D 211/82* | (2006.01) |
| *C07D 401/10* | (2006.01) |
| *A61K 8/49* | (2006.01) |
| *C09D 5/32* | (2006.01) |
| *A61Q 17/04* | (2006.01) |
| *C07C 49/543* | (2006.01) |
| *C07C 49/792* | (2006.01) |
| *C07C 49/807* | (2006.01) |
| *C09K 15/30* | (2006.01) |

(52) U.S. Cl.
CPC .......... *C07D 211/70* (2013.01); *A61K 8/4926* (2013.01); *A61Q 17/04* (2013.01); *C07C 49/543* (2013.01); *C07C 49/792* (2013.01); *C07C 49/807* (2013.01); *C07D 211/82* (2013.01); *C07D 401/10* (2013.01); *C09D 5/32* (2013.01); *C09K 15/30* (2013.01)

(58) Field of Classification Search
None
See application file for complete search history.

(56) References Cited

U.S. PATENT DOCUMENTS

2012/0040387 A1   2/2012  Matsuoka

FOREIGN PATENT DOCUMENTS

| WO | WO 1988/002251 | 4/1988 |
|---|---|---|
| WO | WO 1990/009995 | 9/1990 |
| WO | WO 2012/070509 | 5/2012 |
| WO | WO 2014/082124 | 6/2014 |
| WO | WO 2015/006803 | 1/2015 |

OTHER PUBLICATIONS

Lyutenko et al.,Tetrahedron Letters, vol. 54, No. 31, pp. 4091-4093 (Year: 2013).*
Beckwith et al., "Diastereoselective radical cyclization reactions; the synthesis of O-methylcorytenchirine," *ARKIVOC*, pp. 80-93, 2004.
Brewster et al., "Reactivity of Biologically Important Reduced Pyridines: Energetics and Effect of Substitution of Hydride versus Electron Transfer in Dihydropyridines, Dihydroquinolines, and Dihydroisoquinolines," *Journal of Organic Chemistry*, vol. 55, pp. 2361-2366, 1990.
De Faria et al., "Synthesis of Indolizines and Pyrrolizidines through the [2+2]Cycloaddition of Five-Membered Endocyclic Enecarbamates to Alkyl Ketenes: Unusual Regioselectivity of Baeyer-Villiger Ring Expansions of Alkyl Aza-Bicyclic Cyclobutatones," *Journal of Organic Chemistry*, vol. 67, pp. 3651-3661, 2002.
Dunlap et al., "Uric acid photo-oxidation assay: in vitro comparison of sunscreening agents," *International Journal of Cosmetic Science*, vol. 20, pp. 1-18, 1998.
Huang et al., "Nickel-, Palladium-, and Platinum-Catalyzed Reactions of Perfluoro- and Polyfluoroalkyl Iodides with Tertiary Amines," *Journal of Organic Chemistry*, vol. 52, pp. 3552-3558, 1987.
International Search Report and Written Opinion issued for International Application No. PCT/AU2016/051162 dated Jan. 19, 2017, 12 pages.

* cited by examiner

*Primary Examiner* — Zinna Northington Davis
(74) *Attorney, Agent, or Firm* — Klarquist Sparkman, LLP

(57) ABSTRACT

The present invention describes compounds and uses thereof in applications relating to absorption of electromagnetic energy. Preferred compounds are double bond-containing cyclic compounds capable of absorbing electromagnetic radiation energy and having improved photostability due to the presence and location of one or more fluorine groups in relation to the double bond of the ring.

12 Claims, 3 Drawing Sheets

PHOTOSTABLE COMPOUNDS, ABSORBING COMPOUNDS AND USES THEREOF

CROSS REFERENCE TO RELATED APPLICATIONS

This is the U.S. National Stage of International Application No. PCT/AU2016/051162, filed Nov. 28, 2016, which was published in English under PCT Article 21(2), which in turn claims the benefit of Australian Application No. 2015904932, filed Nov. 27, 2015.

FIELD OF THE INVENTION

The invention relates to compounds capable of absorbing energy to thereby provide a protective effect. More particularly, this invention relates to compounds for absorbing electromagnetic radiation, approaches to improving their stability and compositions comprising said compounds.

BACKGROUND TO THE INVENTION

Any reference to background art herein is not to be construed as an admission that such art constitutes common general knowledge in Australia or elsewhere.

Ultraviolet light (UV) and visible light absorbing or screening compounds have found use in a range of applications where protection from the sun's harmful UV rays is desirable. This includes their use in glass and lens coatings, paints, packaging, household cleaning formulations and materials including fabrics as well as, perhaps most notably, in sun screen formulations to protect the skin of the user from damage caused by UV radiation.

Compounds suitable for absorbing UV light, and therefore offering a protective function, were described in WO 2015/006803 in the name of the present applicant. The compounds disclosed therein displayed a cyclic enaminoketone core with a range of substitutions designed to provide a useful variance in absorption characteristics to provide for coverage throughout the UV range. While effective for their primary purpose the stability of the compounds to exposure to electromagnetic radiation was not considered or discussed in any form.

Inorganic sunscreens, such as zinc oxide, protect from UV primarily by light scattering. Conversely organic sunscreen agents, such as those described in WO 2015/006803, absorb the UV light and must then emit this energy in order to return to the ground state. Such energy loss can occur by any or all of a variety of pathways such as fluorescence, phosphorescence, transfer to another molecule, isomerisation, heat generation or fragmentation. If destructive pathways such as fragmentation, and some isomerisations, predominate then the ability of the molecule to continue to absorb UV or visible light is destroyed. While protective compounds are not required to be indefinitely photostable it is important that they provide for a useful lifetime and so resist fast degradation.

It would therefore be desirable to provide for compounds which can absorb energy from a variety of ranges within the electromagnetic spectrum and which can demonstrate improved stability to this exposure to provide for a greater operational lifespan.

Further, there is an ongoing need for compounds, whether preferentially stabilised or not, which provide for effective absorption of electromagnetic energy in different regions of the spectrum, particularly in the UV and visible light parts of the spectrum.

SUMMARY OF THE INVENTION

It has been found that cyclic enamine compounds provided with at least one electron withdrawing group, for example, a trifluoroacetyl or perfluoro alkyl chain linked to the ring via a doubly bonded carbon atom, provide for greatly improved stability over their simple alkanoyl analogues. This advantage may be extended out to other double-bond containing compounds, both cyclic and aliphatic. The electron-withdrawing effect of the substituent, such as one or more fluorine atoms, means that exposure of such compounds to electromagnetic radiation results in reduced degradation of the compound thereby providing for an increased operational lifespan when employed in electromagnetic radiation protective applications.

Further, in one embodiment, the present invention provides for compounds which are absorbers of electromagnetic energy and which, due to variation in side chains, provide, in concert, for absorption over a wide range of the electromagnetic spectrum. Effective absorption, and so a useful protective effect, is achieved particularly over the UV-A, UV-B and visible regions of the spectrum.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

DETAILED DESCRIPTION

Figure 1:
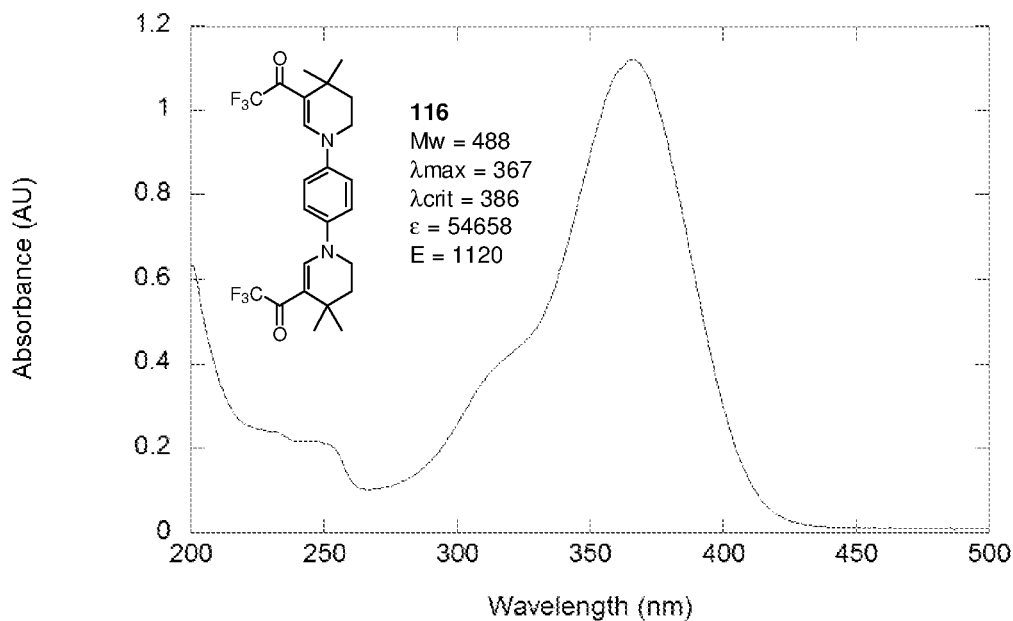
FIG. 1 is a graphical representation of the absorbance of compound 116.

The present invention is predicated, at least in part, on the finding that double bond-containing cyclic compounds capable of absorbing electromagnetic radiation energy can have their stability, upon exposure to the electromagnetic radiation, greatly improved if the carbon atom adjacent a doubly bonded carbon, which is itself attached directly to the ring, has at least one halogen atom, preferably a fluorine, bonded thereto. In highly preferred embodiments, this carbon atom has at least two halogen, preferably fluorine atoms, bonded directly to it. Alternatively, the carbon atom adjacent the doubly bonded carbon, which is itself attached directly to the ring, may be part of or adjacent a ring system to which a halogen, preferably a fluorine, is attached.

While not wishing to be bound by any particular theory the inventors postulate that the improvement in stability over comparable compounds not having carbon-halogen bonds at the same position comes from two complimentary effects. The first is, in some embodiments displaying this arrangement, the removal of all protons α to the carbonyl carbon (as the carbon would be identified if W is oxygen in the below structure) prevents enolisation/hydrogen abstraction at this position which increases stability. Secondly and more importantly, the strong electron withdrawing effect of the halogen on this carbon likely reduces electron density within the cyclic ene system thereby greatly stabilising the ring system.

While it is known that electron withdrawing groups can reduce electron density around adjacent functional groups and thereby decrease chemical reactivity, it is important to realise that chemical reactivity is not the same as, and is certainly not predictive of, photostability. The underlying mechanisms of chemical reactivity and photostability (or release of excitation energy upon irradiation) are significantly different with a variety of different considerations. It could therefore not reasonably be predicted with any degree of certainty that a compound which has reduced chemical reactivity due to the presence of an electron withdrawing group would also demonstrate improved photostability and would, at the same time, prove to be an effective absorber of electromagnetic radiation, such as UV and visible light.

The present invention is further predicated on the identification and synthesis of a number of cyclic enamine compounds which are effective absorbers of electromagnetic energy and which, when looked at holistically as a collection of compounds, have been found to provide for useful protective effects across an important region of the electromagnetic spectrum.

According to a first aspect of the present invention, there is provided a compound of formula Ia, or a salt thereof:

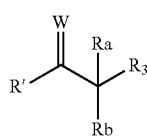

formula Ia wherein, R' is selected from the group consisting of $C_2$ to $C_{20}$ alkenyl, $C_2$ to $C_{20}$ alkynyl, aryl, heteroaryl, aroyl, $C_2$ to $C_{12}$ alkenone, $C_5$ to $C_7$ cycloalkenyl, $C_4$ to $C_7$ cycloalkenone, N-aryl, N-heterocyclyl, heterocyclic and any existing electromagnetic radiation filter all of which groups may be substituted or unsubstituted;

W is selected from O, S, N and C;

$R_a$, $R_b$ and $R_3$, when present, are independently selected from the group consisting of hydrogen, halo, $C_1$ to $C_{20}$ alkyl, $C_2$ to $C_{20}$ alkenyl, $C_2$ to $C_{20}$ alkynyl, aryl, heteroaryl, aroyl, $C_2$ to $C_{12}$ alkanone, $C_5$ to $C_7$ cycloalkyl, $C_4$ to $C_7$ cycloalkanone, $C_5$ to $C_7$ cycloalkenyl, $C_2$ to $C_{12}$ alkanoyl, $C_2$ to $C_{12}$ alkanoyloxy, $C_2$ to $C_{12}$ alkoxycarbonyl, $C_2$ to $C_{12}$ carbamoyl, $C_2$ to $C_{12}$ carboxyl, haloalkyl, N-alkyl, N-aryl, N-heterocyclyl and heterocyclic, all of which groups may be substituted or unsubstituted, or $R_b$ and $R_3$ may together form an alkene, an alkyne, a phenyl ring or a heteroaryl ring each of which is optionally substituted with at least one halogen or halogen-containing group;

with the proviso that if $R_a$, $R_b$ and $R_3$ are all fluorine and R' is a 6-membered nitrogen-containing alkene heterocycle then the nitrogen of that ring is not substituted with any of 4-dimethylaminophenyl, 4-methoxyphenyl, 4-methylphenyl, 4-tert-butylphenyl, isopropyl or 1-naphthyl.

In one embodiment of the first aspect, there is provided a compound of formula Ib, or a salt thereof:

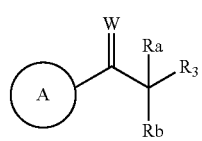

formula Ib wherein, A is a six or seven-membered ring comprising at least one double bond, which ring may be further substituted or unsubstituted;

W is selected from O, S, N and C;

$R_a$, $R_b$ and $R_3$, when present, are independently selected from the group consisting of hydrogen, halo, $C_1$ to $C_{20}$ alkyl, $C_2$ to $C_{20}$ alkenyl, $C_2$ to $C_{20}$ alkynyl, aryl, heteroaryl, aroyl, $C_2$ to $C_{12}$ alkanone, $C_5$ to $C_7$ cycloalkyl, $C_4$ to $C_7$ cycloalkanone, $C_5$ to $C_7$ cycloalkenyl, $C_2$ to $C_{12}$ alkanoyl, $C_2$ to $C_{12}$ alkanoyloxy, $C_2$ to $C_{12}$ alkoxycarbonyl, $C_2$ to $C_{12}$ carbamoyl, $C_2$ to $C_{12}$ carboxyl, haloalkyl, N-alkyl, N-aryl, N-heterocyclyl and heterocyclic, all of which groups may be substituted or unsubstituted, or $R_b$ and $R_3$ may together form an alkene, an alkyne, a phenyl ring or a heteroaryl ring each of which is optionally substituted with at least one halogen or halogen-containing group;

with the proviso that if $R_a$, $R_b$ and $R_3$ are all fluorine and A is a 6-membered nitrogen-containing alkene heterocycle then the nitrogen of that ring is not substituted with any of 4-dimethylaminophenyl, 4-methoxyphenyl, 4-methylphenyl, 4-tert-butylphenyl, isopropyl or 1-naphthyl.

In one embodiment of the first aspect, there is provided a compound of formula II, or a salt thereof:

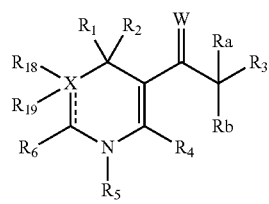

formula II wherein, the dotted line may be a bond;

X is one or two carbon atoms forming part of the ring structure;

$R_1$ and $R_2$ are independently selected from the group consisting of $C_1$ to $C_{10}$ alkyl, $C_1$ to $C_{10}$ alkenyl and $C_1$ to $C_{10}$ alkoxy, each of which groups may be substituted or unsubstituted;

W is selected from O, S, N and C;

$R_a$, $R_b$ and $R_3$, when present, are independently selected from the group consisting of hydrogen, halo, $C_1$ to $C_{20}$ alkyl, $C_2$ to $C_{20}$ alkenyl, $C_2$ to $C_{20}$ alkynyl, aryl, heteroaryl, aroyl, $C_2$ to $C_{12}$ alkanone, $C_5$ to $C_7$ cycloalkyl, $C_4$ to $C_7$ cycloalkanone, $C_5$ to $C_7$ cycloalkenyl, $C_2$ to $C_{12}$ alkanoyl, $C_2$ to $C_{12}$ alkanoyloxy, $C_2$ to $C_{12}$ alkoxycarbonyl, $C_2$ to $C_{12}$ carbamoyl, $C_2$ to $C_{12}$ carboxyl, haloalkyl, N-alkyl, N-aryl, N-heterocyclyl and heterocyclic, all of which groups may be substituted or unsubstituted, or $R_b$ and $R_3$ may together form an alkene, an alkyne, a phenyl ring or a heteroaryl ring each of which is optionally substituted with at least one halogen or halogen-containing group;

$R_4$ is selected from the group consisting of hydrogen, $C_1$ to $C_{12}$ alkyl, $C_2$ to $C_{12}$ alkenyl, aryl, heteroaryl, $C_5$ to $C_7$ cycloalkyl, $C_5$ to $C_7$ cycloalkenyl, $C_1$ to $C_{12}$ alkanoyl, $C_1$ to $C_{12}$ alkanoyloxy, $C_1$ to $C_{12}$ carboalkoxy and $C_1$ to $C_{12}$ alkanone all of which groups may be substituted or unsubstituted;

$R_5$ is selected from the group consisting of $C_1$ to $C_{20}$ alkyl, $C_2$ to $C_{20}$ alkenyl, $C_2$ to $C_{20}$ alkynyl, aryl, amine, heteroaryl, heterocyclyl, $C_5$ to $C_7$ cycloalkyl, $C_5$ to $C_7$ cycloalkenyl, $C_2$ to $C_9$ alkanoyl, $C_1$ to $C_{12}$ alkanoyloxy and carbamoyl all of which groups may be substituted or unsubstituted;

$R_6$ is selected from the group consisting of hydrogen, oxo, substituted or unsubstituted $C_1$ to $C_6$ alkyl, substituted or unsubstituted $C_2$ to $C_6$ alkenyl and substituted or unsubstituted $C_2$ to $C_6$ alkanoyl; and $R_{18}$ and $R_{19}$ are independently selected from the group consisting of hydrogen, $C_1$ to $C_6$ alkyl, $C_1$ to $C_6$ alkenyl and $C_1$ to $C_6$ alkoxy, each of which groups may be substituted or unsubstituted, with the proviso that when $R_1$ and $R_2$ are methyl, $R_a$, $R_b$ and $R_3$ are all fluorine, W is O and $R_4$ is hydrogen then $R_5$ is not any of 4-dimethylaminophenyl, 4-methoxyphenyl, 4-methylphenyl, 4-tert-butylphenyl, isopropyl or 1-naphthyl.

In one embodiment of the compound of formula Ia, R' is selected from the group consisting of $C_2$ to $C_{12}$ alkenyl, $C_2$ to $C_{12}$ alkynyl, $C_5$ to $C_7$ aryl, $C_5$ to $C_7$ heteroaryl, $C_5$ to $C_7$ aroyl, $C_2$ to $C_{12}$ alkenone, $C_5$ to $C_7$ cycloalkenyl, $C_4$ to $C_7$ cycloalkenone, and $C_5$ to $C_7$ heterocyclic, all of which groups may be substituted or unsubstituted.

In one embodiment, R' is selected from the group consisting of $C_2$ to $C_{12}$ alkenyl, $C_2$ to $C_{12}$ alkynyl, $C_5$ or $C_6$ aryl, $C_5$ or $C_6$ heteroaryl, $C_5$ or $C_6$ aroyl, $C_2$ to $C_{12}$ alkenone, $C_5$ or $C_6$ cycloalkenyl, $C_5$ or $C_6$ cycloalkenone, and $C_5$ or $C_6$ heterocyclic, all of which groups may be substituted or unsubstituted.

In one embodiment of the compound of formula Ib, A is selected from the group consisting of a six or seven-membered nitrogen heterocycle comprising at least one double bond, which nitrogen heterocycle may be further substituted or unsubstituted.

In one embodiment of the compound of formula Ib, A is a six-membered nitrogen heterocycle comprising at one double bond, which nitrogen heterocycle may be further substituted or unsubstituted.

In one embodiment of the compound of formula Ib, A is a six-membered nitrogen heterocycle comprising one double bond and having the carbon atom to which W is attached also attached to a double bonded ring carbon, which nitrogen heterocycle may be further substituted or unsubstituted.

In one embodiment, $R_1$ and $R_2$ are independently selected from the group consisting of $C_1$ to $C_6$ alkyl, $C_1$ to $C_6$ alkenyl and $C_1$ to $C_6$ alkoxy, each of which groups may be substituted or unsubstituted.

In any embodiment, $R_1$ and $R_2$ are independently selected from $C_1$ to $C_4$ alkyl which may be substituted or unsubstituted.

In any embodiment, $R_1$ and $R_2$ are independently selected from methyl, ethyl or propyl.

In one preferred embodiment of the above formulae, X is one carbon atom.

In one preferred embodiment of the above formulae, W is O.

In any embodiment of the compound of formula Ia, Ib or II, $R_a$ and $R_b$ are independently selected from hydrogen, $C_1$ to $C_{12}$ alkyl, $C_1$ to $C_{12}$ haloalkyl, fluorine, chlorine, bromine and iodine.

In any embodiment of the compound of formula Ia, Ib or II, at least one of $R_a$, $R_b$ and $R_3$ is a halogen.

In one preferred embodiment of the compound of formula Ia, Ib or II, at least one of $R_a$ and $R_b$ are fluorine.

In one embodiment, both $R_a$ and $R_b$ are fluorine.

When $R_b$ and $R_3$ form a phenyl ring or a heteroaryl ring it will be appreciated that the carbon to which $R_b$ and $R_3$ are attached will form part of that ring and that, in combination with the carbonyl group when W is oxygen, will form a benzoyl or heteroaroyl group attached to the ring for formula Ib and When $R_b$ and $R_3$ form an alkene, an alkyne, a phenyl ring or a heteroaryl ring the at least one halogen substituent is, in each incidence thereof, independently selected from fluorine, chlorine, bromine and iodine. Preferably, the halogen substituent is fluorine.

When $R_b$ and $R_3$ form an alkene, an alkyne, a phenyl ring or a heteroaryl ring the at least one halogen-containing group is, in each incidence thereof, independently selected from $C_1$ to $C_{12}$ haloalkyl, haloaryl and halocycloalkyl. Preferably the $C_1$ to $C_{12}$ haloalkyl is $C_1$ to $C_9$ haloalkyl, even more preferably $C_1$ to $C_6$ haloalkyl.

In one embodiment of the compound of formula Ia, Ib or II, $R_3$ is selected from the group consisting of halo, $C_1$ to $C_9$ alkyl, $C_2$ to $C_9$ alkenyl, $C_5$-$C_6$ aryl, $C_5$-$C_6$ heteroaryl, $C_2$ to $C_{12}$ alkanone, $C_5$-$C_6$ cycloalkyl, $C_5$-$C_6$ cycloalkanone, $C_5$-$C_6$ cycloalkenyl, $C_2$ to $C_9$ alkanoyl, $C_2$ to $C_9$ alkanoyloxy, $C_2$ to $C_9$ alkoxycarbonyl, $C_2$ to $C_9$ carbamoyl, $C_2$ to $C_9$ carboxyl, haloalkyl, N-alkyl, N-aryl, N-heterocyclyl and $C_5$-$C_6$ heterocyclic, all of which groups may be substituted or unsubstituted.

In one embodiment of the compound of formula Ia, Ib or II, $R_3$ is selected from the group consisting of fluoro, chloro, $C_1$ to $C_6$ fluoroalkyl, $C_2$ to $C_6$ fluoroalkenyl, $C_6$ aryl, $C_6$ heteroaryl, $C_2$ to $C_6$ alkanone, $C_6$ cycloalkyl, $C_6$ cycloalkanone, $C_6$ cycloalkenyl, $C_2$ to $C_6$ alkanoyl, $C_2$ to $C_6$ alkanoyloxy, $C_2$ to $C_6$ alkoxycarbonyl, $C_2$ to $C_6$ carbamoyl, $C_1$ to $C_9$ perfluoroalkyl, and $C_6$-$C_6$ heterocyclic, all of which groups may be substituted or unsubstituted.

In one embodiment of the compound of formula Ia, Ib or II, $R_3$ is fluoro or perfluoroalkyl.

Suitably, perfluoroalkyl may be selected from $C_1$ to $C_{12}$ perfluoroalkyl, $C_1$ to $C_9$ perfluoroalkyl, $C_1$ to $C_6$ perfluoroalkyl and $C_1$ to $C_4$ perfluoroalkyl.

In certain embodiments wherein $R_3$ comprises a heterocycle, a cycloalkene or an alkylcycloalkene then the compound may comprise two structures of formula Ia, Ib or II linked by a carbon chain forming both respective $R_3$ groups. Preferably, the carbon chain comprises at least one carbon-fluorine bond. In certain embodiments at least two carbons in the chain have at least one carbon-fluorine bond. In one preferred embodiment, the carbon chain is a chain of between 2 to 8 carbons, suitably 2 to 6 carbons and preferably 2 to 4 carbons. All carbons in the linking chain may have one or two fluorine atoms bonded thereto.

In one embodiment, the first carbon of the $R_3$ group may have at least one carbon-halogen bond.

In certain embodiments, the first carbon of the $R_3$ group has only carbon-halogen bonds, preferably only carbon-fluorine bonds.

In one embodiment of any of formulae Ia, Ib or II, $R_a$, $R_b$ and $R_3$ and the carbon to which they are attached, form a moiety selected from the group consisting of:

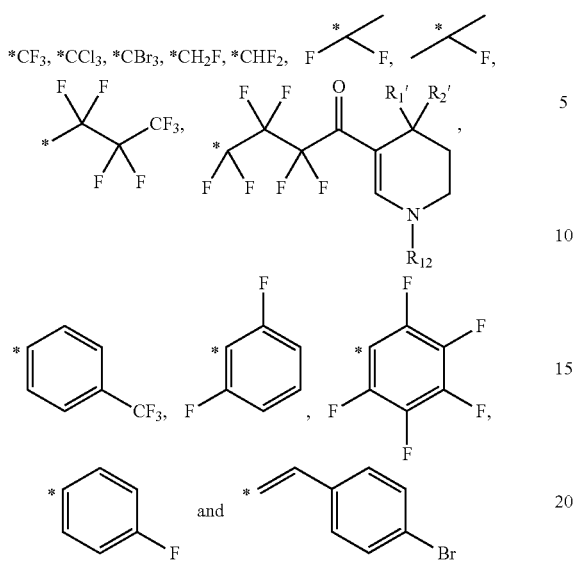

wherein, $R_1'$ and $R_2'$, may be selected from any group already described for $R_1$ and $R_2$, respectively, and $R_{12}$ may be selected from hydrogen, $C_1$-$C_6$ alkyl and $C_1$-$C_6$ alkoxy. In this figure the asterisk shows the carbon atom which is directly attached to the double bonded, preferably carbonyl, carbon.

In certain embodiments, $R_4$ is selected from the group consisting of hydrogen, $C_1$ to $C_6$ alkyl, $C_2$ to $C_6$ alkenyl, phenyl, heteroaryl, $C_6$ cycloalkyl, $C_1$ to $C_{12}$ alkanoyl, $C_1$ to $C_9$ alkanoyloxy, $C_1$ to $C_9$ carboalkoxy and $C_1$ to $C_6$ alkanone all of which groups may be substituted or unsubstituted.

In certain embodiments, $R_4$ is selected from the group consisting of hydrogen, $C_1$ to $C_6$ alkyl, $C_2$ to $C_6$ alkenyl, phenyl, $C_6$ cycloalkyl, $C_1$ to $C_{12}$ alkanoyl and $C_1$ to $C_{12}$ alkanoyloxy all of which groups may be substituted or unsubstituted.

In embodiments, $R_4$ is selected from the group consisting of hydrogen, phenyl, butan-2-one and but-1-ene-2-yl propionate.

In certain embodiments, $R_5$ is selected from the group consisting of $C_1$ to $C_{12}$ alkyl, $C_2$ to $C_{12}$ alkenyl, phenyl, aryl, naphthyl, $C_6$ cycloalkyl, $C_2$ to $C_6$ alkanoyl and $C_2$ to $C_6$ alkanoyloxy all of which groups may be substituted or unsubstituted.

In one embodiment, $R_5$ is selected from the group consisting of $C_1$ to $C_6$ alkyl, $C_2$ to $C_6$ alkenyl, phenyl, $C_6$ aryl and $C_6$ cycloalkyl all of which groups may be substituted or unsubstituted.

In one embodiment, wherein $R_5$ is substituted aryl, then the substitution of the aryl ring may be with a group selected from alkyl, amino, hydroxy, alkoxy, aryloxy, phenyl, benzyl, $C_6$ aryl, $C_6$ heterocycle, alkoxyaryl, each of which groups may be substituted or unsubstituted.

In any of the above embodiments, including reference to substitution of an aryl ring, any reference to a heterocycle is preferably a nitrogen heterocycle. In one embodiment, the nitrogen heterocycle attached to the aryl group may be a 6-membered enamine ring which may be optionally substituted in manner set out for formula II.

In one embodiment, $R_5$ is directly attached to the nitrogen of the ring via a tertiary carbon.

In certain embodiments wherein when $R_5$ is alkyl, it is tert-butyl.

In one embodiment, $R_5$ is selected from the group consisting of:

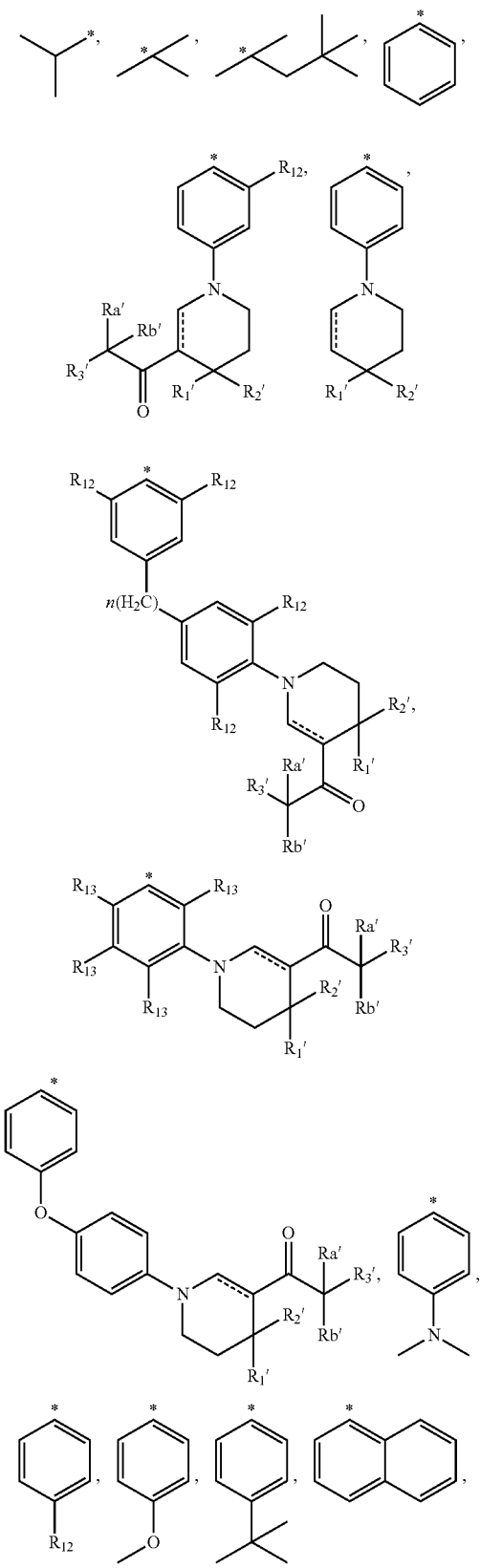

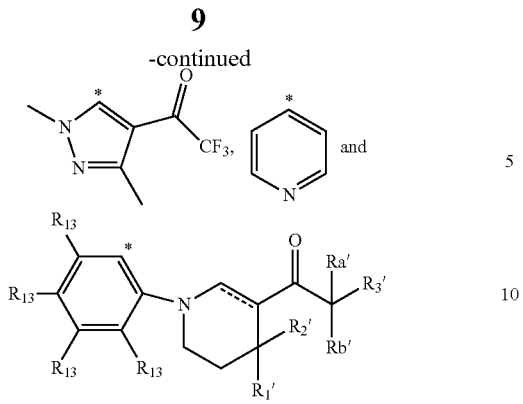

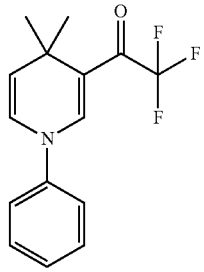

wherein, a dotted line may be a bond, n is from 0 to 5, $R_1'$, $R_2'$, $R_a'$, $R_b'$ and $R_3'$ may be selected from any group already described for $R_1$, $R_2$, $R_a$, $R_b$ and $R_3$, respectively, and each incidence of $R_{12}$ and $R_{13}$ is independently selected from hydrogen, $C_1$-$C_6$ alkyl and $C_1$-$C_6$ alkoxy.

In the figures the asterisk shows the atom of attachment of the relevant group to the ring nitrogen.

In embodiments, $R_6$ is selected from the group consisting of hydrogen, oxo, substituted or unsubstituted $C_1$ to $C_6$ alkyl, substituted or unsubstituted $C_2$ to $C_6$ alkenyl and substituted or unsubstituted $C_2$ to $C_6$ alkanoyl.

In any of the embodiments described, $R_6$ is selected from the group consisting of hydrogen, oxo and substituted or unsubstituted $C_1$ to $C_6$ alkyl.

In a preferred embodiment, $R_6$ is hydrogen or oxo.

In any of the embodiments described, $R_{18}$ and $R_{19}$ are independently selected from the group consisting of hydrogen and $C_1$ to $C_6$ alkyl which may be substituted or unsubstituted.

In certain preferred embodiments, $R_{18}$ and $R_{19}$ are hydrogen.

In one embodiment, the compound of the first aspect is a non-naturally occurring compound.

In one embodiment of the first aspect, the compound may be two formula II structures linked by a linking group. The linking group may be as described for any of $R_a$, $R_b$ and $R_3$. Such a compound may be considered a dimer or a multivalent presentation of a compound of the first aspect.

In one embodiment, the linking group is selected from one or more incidences of aryl, alkylaryl and alkoxyaryl, each of which may themselves be substituted or unsubstituted.

In any one or more of the abovedescribed embodiments of the compounds of formulae Ia, Ib and II, as appropriate, preferably W is O, X is one carbon, the dotted line is not a bond, $R_4$, $R_6$, $R_{18}$ and $R_{19}$ are hydrogen, and $R_1$ and $R_2$ are independently selected from methyl, ethyl and propyl.

In one embodiment, the compound of formula Ia, Ib or II is selected from the group consisting of:

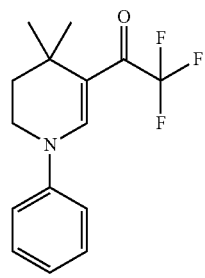

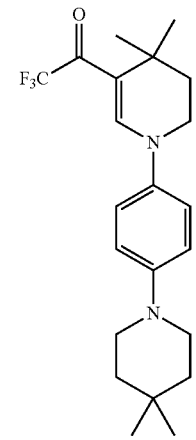

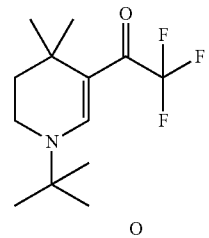

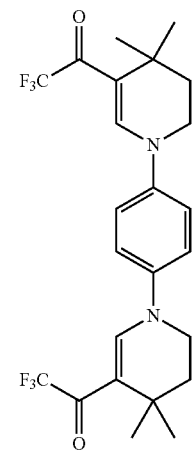

159
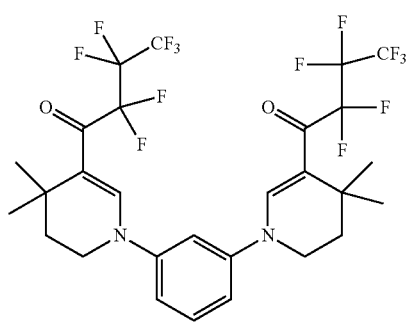
108
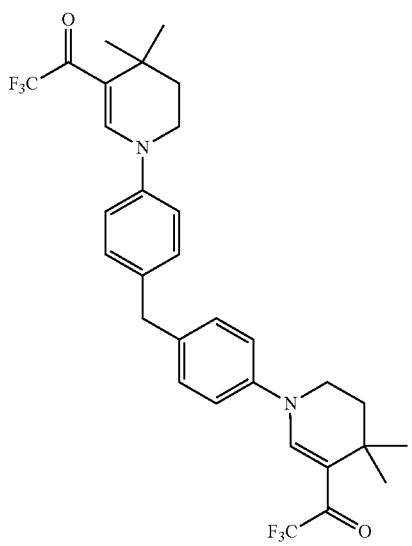
160
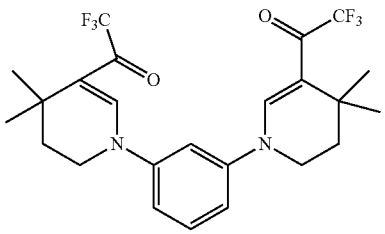
111
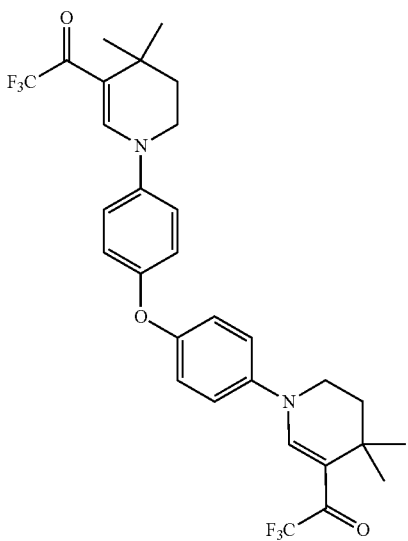
120   121
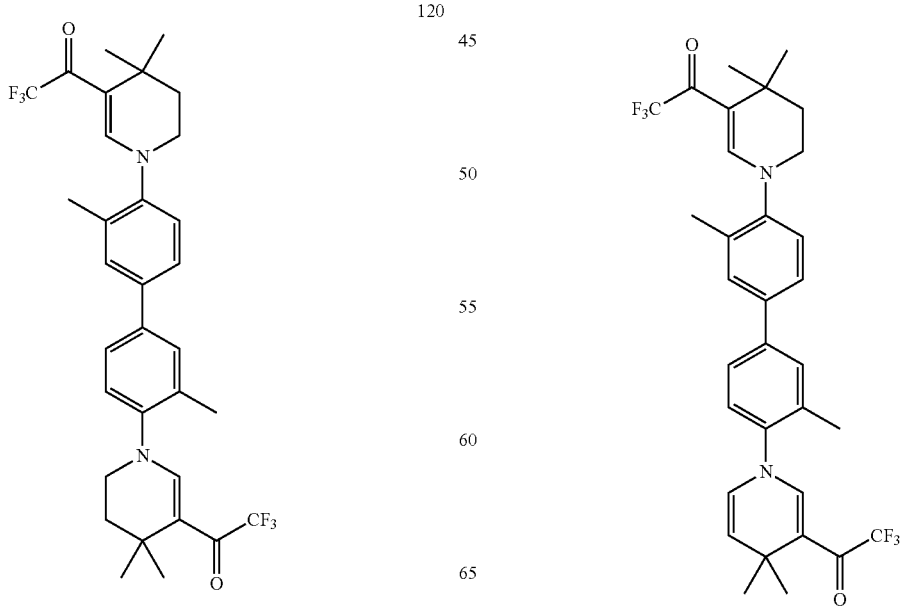

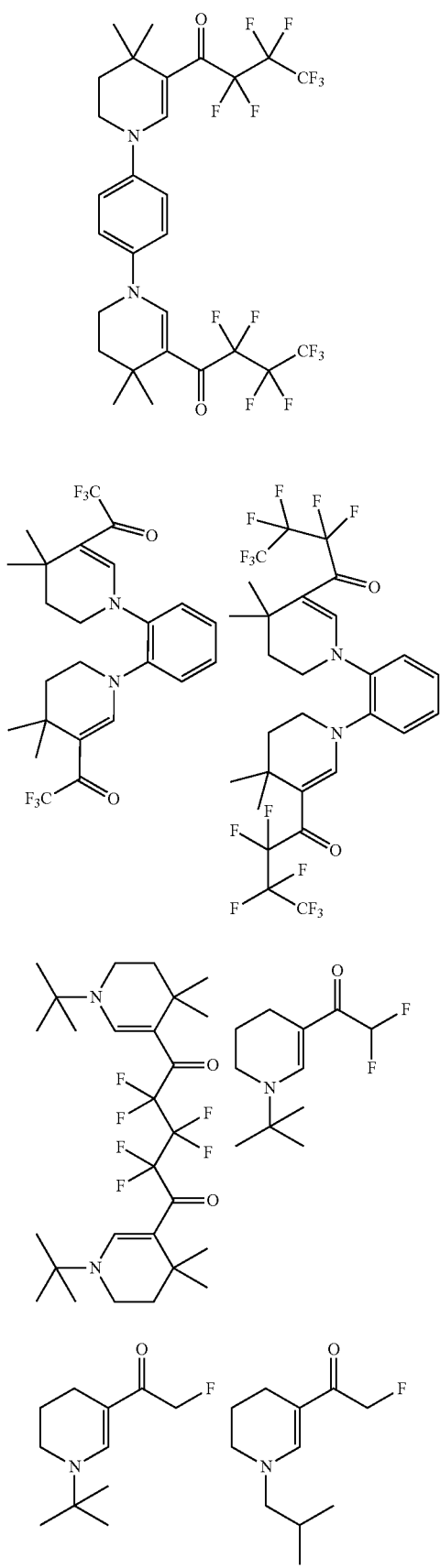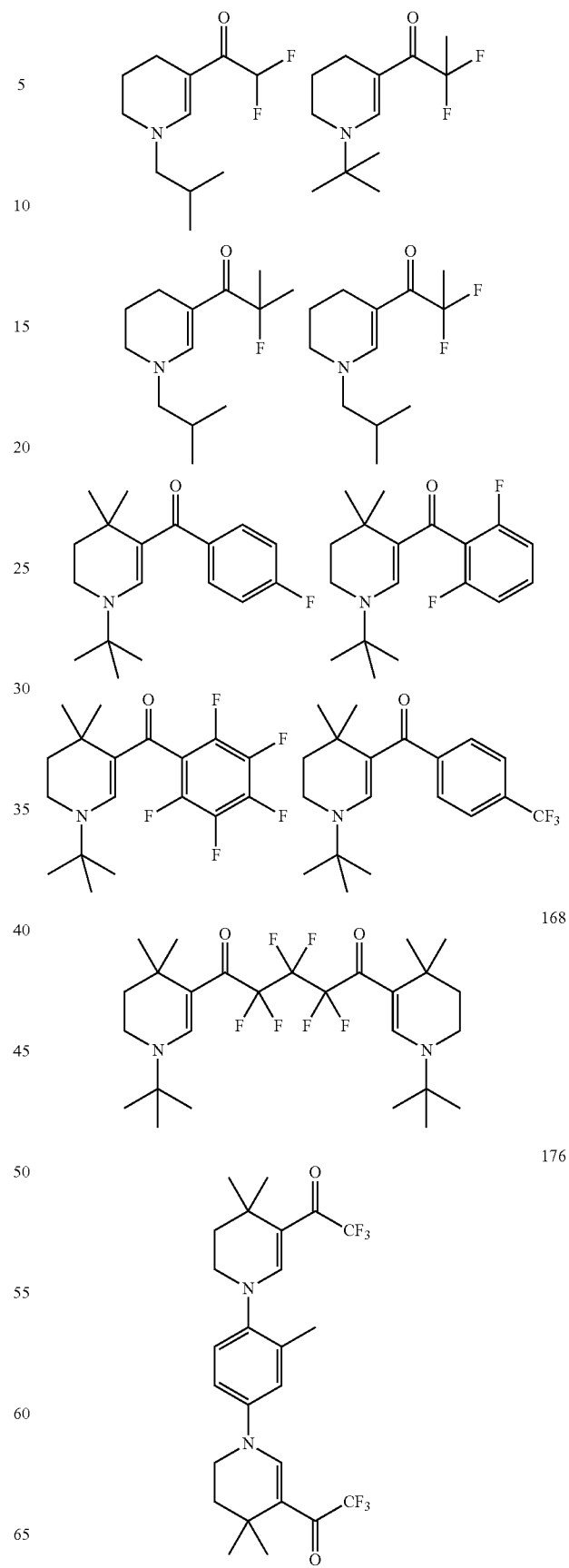

In one embodiment, the compound of formula Ia, Ib or II is not a compound selected from the group consisting of:

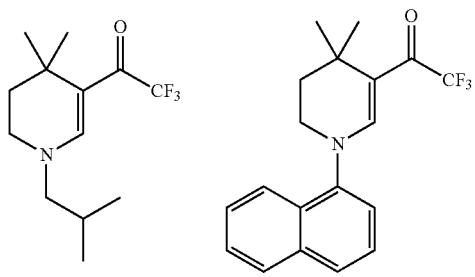

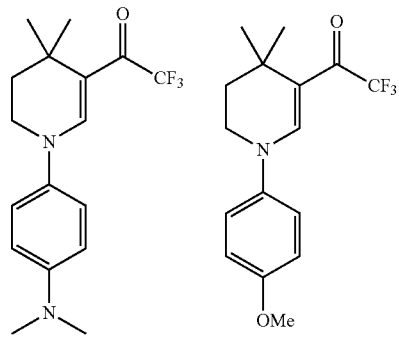

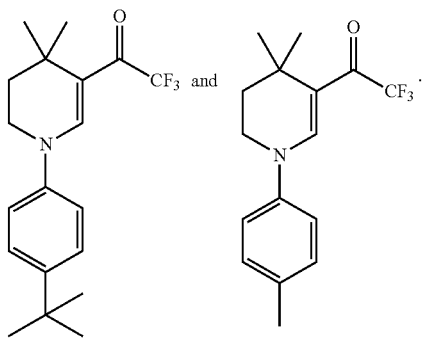

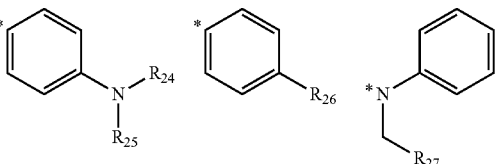

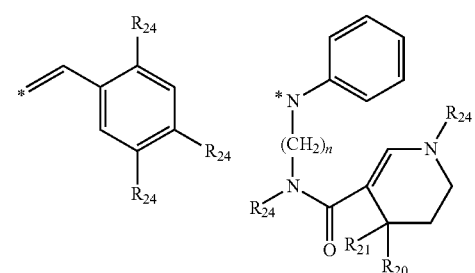

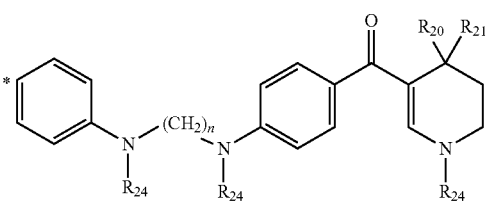

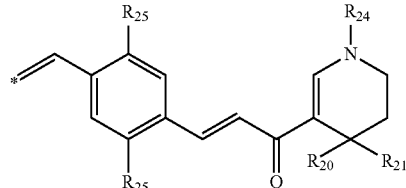

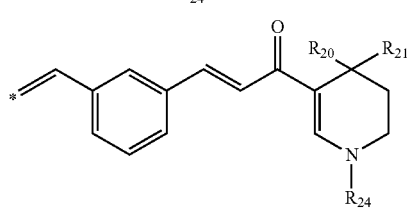

In one alternative embodiment of the first aspect the compound may be a compound of formula V:

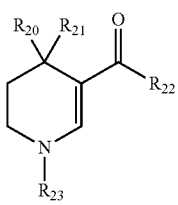

formula V wherein, $R_{20}$ and $R_{21}$ are independently selected from the group consisting of $C_1$ to $C_6$ alkyl, $C_1$ to $C_6$ alkenyl and $C_1$ to $C_6$ alkoxy, each of which groups may be substituted or unsubstituted;

$R_{22}$ is selected from the group consisting of $C_1$ to $C_{20}$ alkyl, $C_1$ to $C_{20}$ alkenyl, $C_2$ to $C_{12}$ alkylalkanoate, $C_5$ or $C_6$ cycloalkyl, $C_5$ or $C_6$ cycloalkenyl, $C_1$ to $C_6$ alkylcycloalkyl, $C_1$ to $C_6$ haloalkyl, $C_5$ or $C_6$ aryl, $C_5$ or $C_6$ aryl substituted with halo, heteroaryl and heterocyclyl, all of which may be substituted or unsubstituted, and from the below groups:

-continued

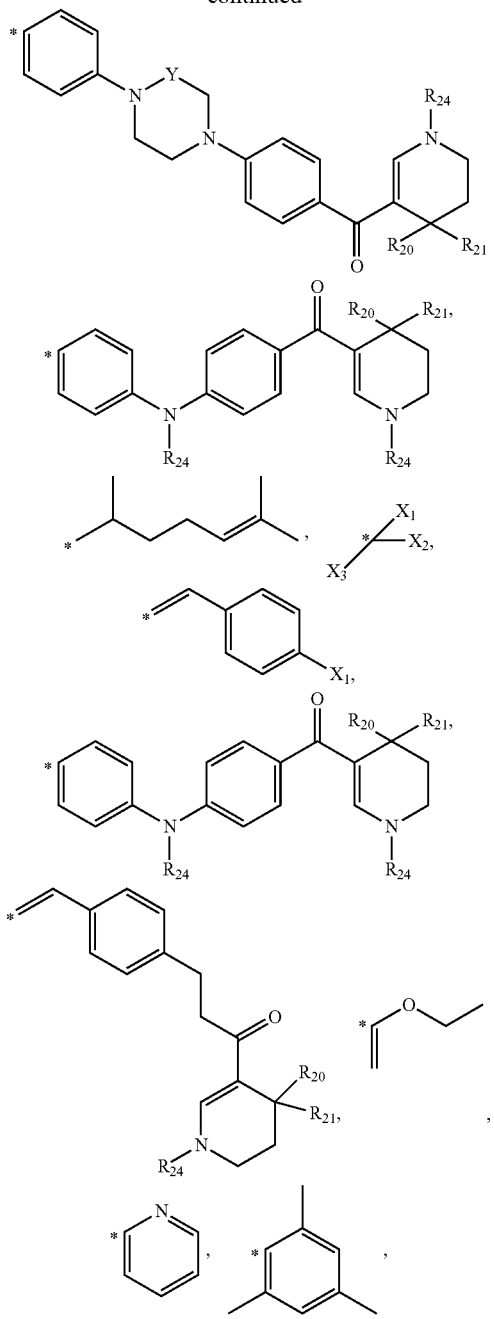

wherein, the asterisk indicates the point of attachment and $R_{20}$ and $R_{21}$ are as previously described;

$R_{24}$ is selected from the group consisting of hydrogen, halo, hydroxyl, $C_1$ to $C_{12}$ alkyl, $C_2$ to $C_{12}$ alkenyl, $C_2$ to $C_{12}$ alkynyl, aryl, heteroaryl, $C_5$ to $C_9$ cycloalkyl, $C_5$ to $C_7$ cycloalkenyl, $C_2$ to $C_9$ alkanoyl, $C_2$ to $C_9$ alkanoyloxy, $C_2$ to $C_{12}$ alkylalkanoate, and carbamoyl all of which groups may be substituted or unsubstituted;

$R_{25}$ is selected from the group consisting of hydrogen, $C_1$ to $C_6$ alkyl, nitro, $C_1$ to $C_6$ alkoxy, $C_2$ to $C_{12}$ alkylalkanoate, each of which may be substituted or unsubstituted, as appropriate;

$R_{26}$ is selected from the group consisting of hydrogen, fluoro, chloro and bromo;

Y is one or two carbon atoms;

n is 0 to 12;

$X_1$, $X_2$ and $X_3$ may be selected from chloro, fluoro and bromo; and $R_{23}$ is selected from the group consisting of $C_1$ to $C_{12}$ alkyl, $C_2$ to $C_{12}$ alkenyl, aryl, heteroaryl, heterocyclyl, $C_5$ to $C_9$ cycloalkyl, $C_5$ to $C_7$ cycloalkenyl, $C_2$ to $C_9$ alkanoyl, $C_2$ to $C_9$ alkanoyloxy and carbamoyl all of which groups may be substituted or unsubstituted, and from the below groups:

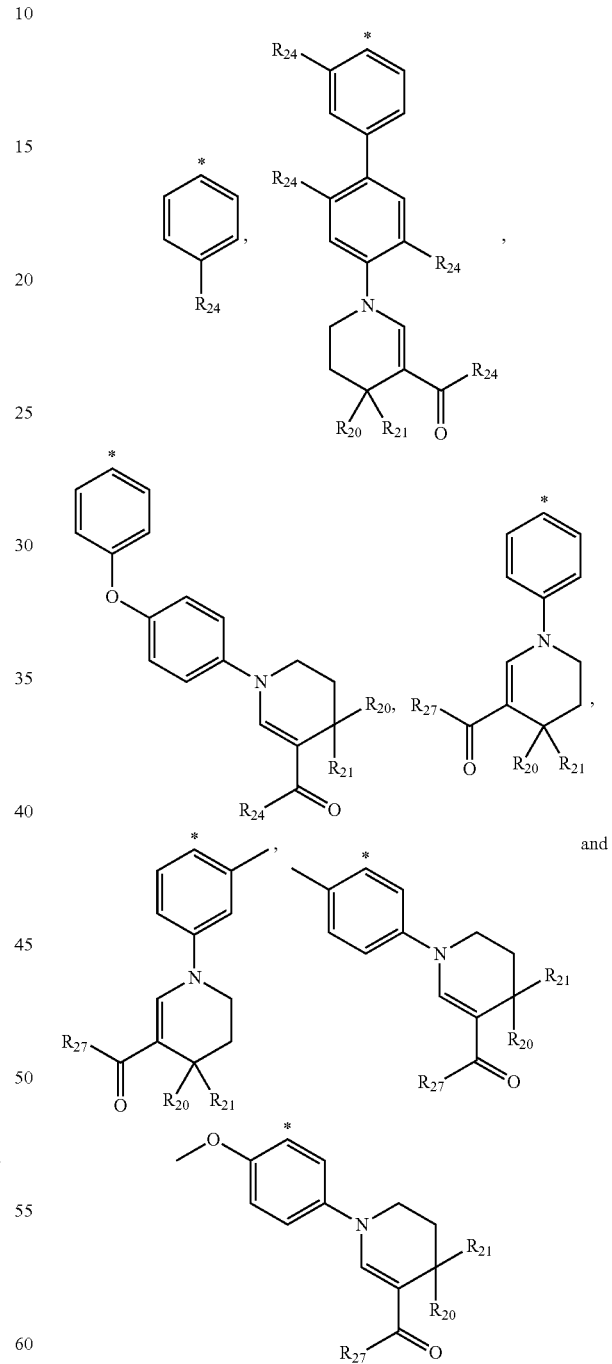

wherein, the asterisk indicates the point of attachment and $R_{20}$, $R_{21}$ and $R_{24}$ are as previously described; and $R_{27}$ is selected from the group consisting of $C_1$ to $C_{20}$ alkyl, $C_1$ to $C_6$ haloalkyl, $C_2$ to $C_{12}$ alkenyl, aryl, heteroaryl, and $C_2$ to $C_{20}$ alkylalkanoate.

In certain embodiments, $R_{20}$ and $R_{21}$ are independently selected from the group consisting of methyl, ethyl, propyl and butyl.

In one embodiment, $R_{24}$ is selected from the group consisting of hydrogen, fluoro, bromo, $C_1$ to $C_6$ alkyl, $C_2$ to $C_{12}$ alkenyl, benzyl, phenyl, $C_5$ to $C_5$ cycloalkyl and $C_2$ to $C_{12}$ alkylalkanoate, all of which groups may be substituted or unsubstituted as appropriate.

In one embodiment, n is 0 to 9, preferably 0 to 6.

In one embodiment, the compound of formula V is selected from the group consisting of:

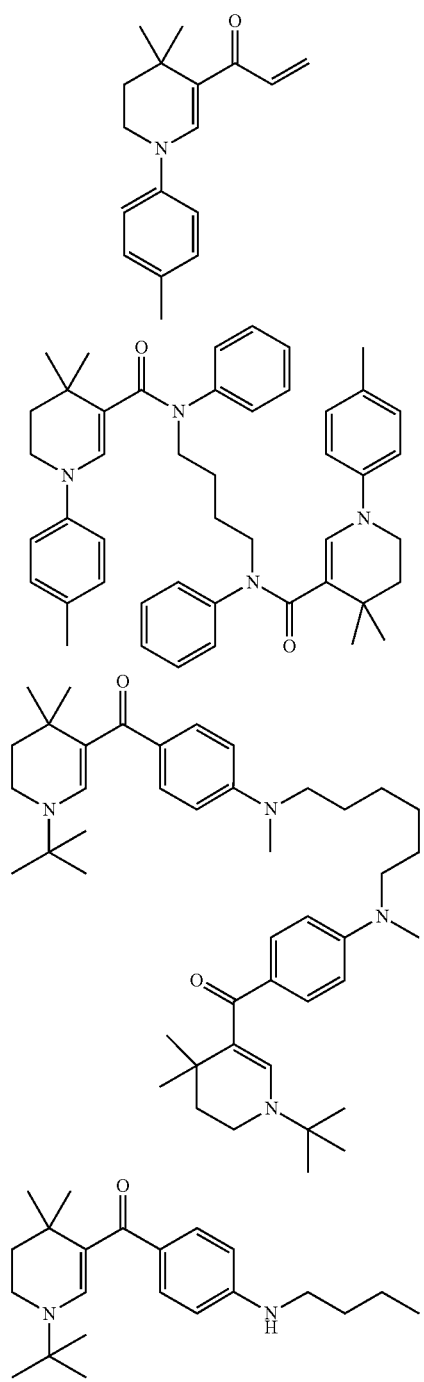

-continued

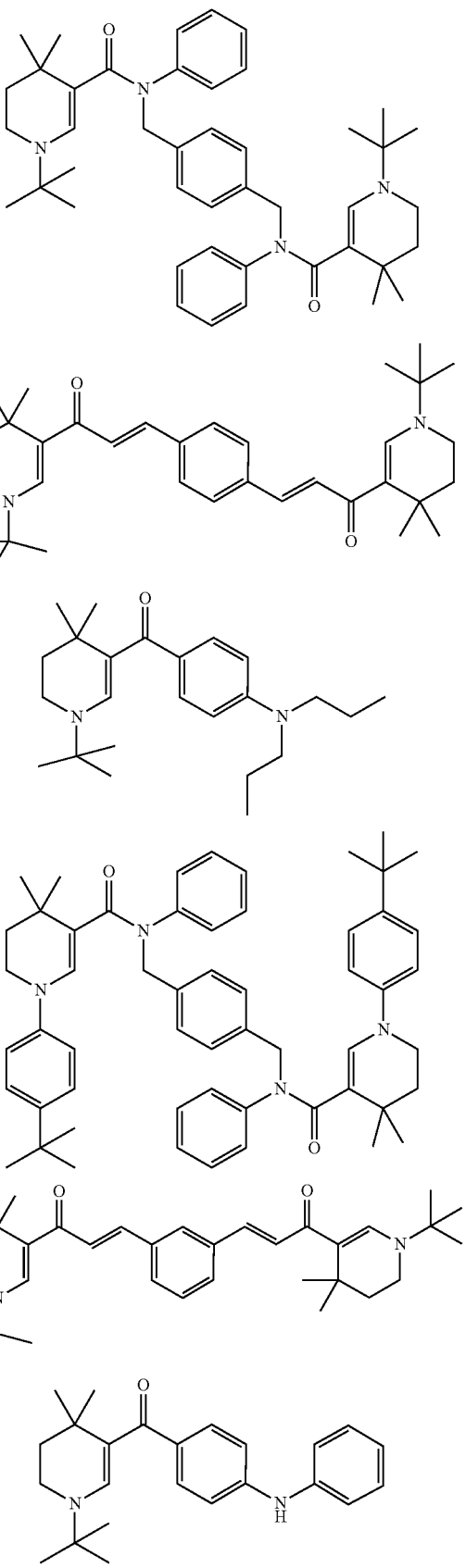

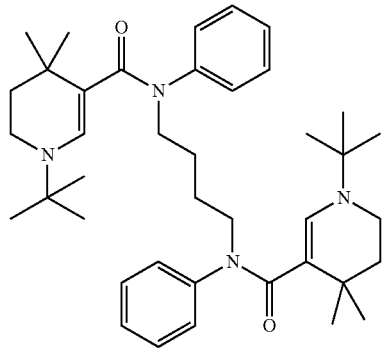
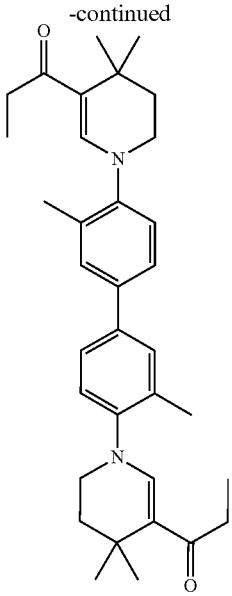
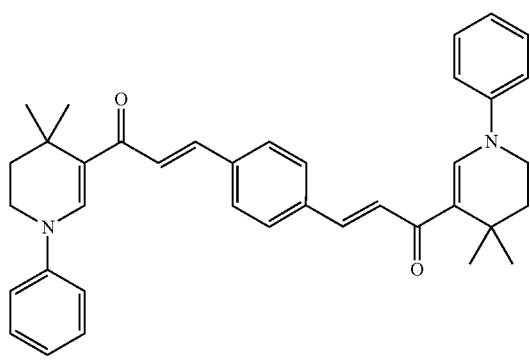
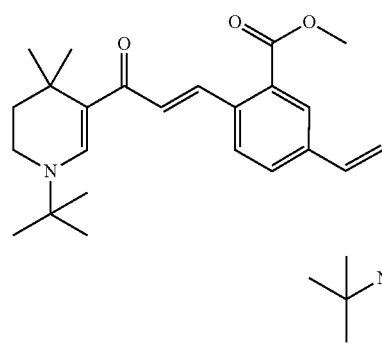
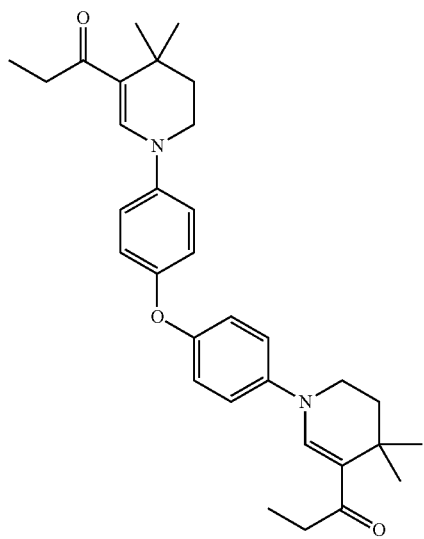
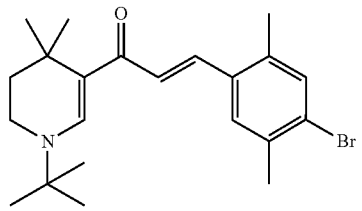
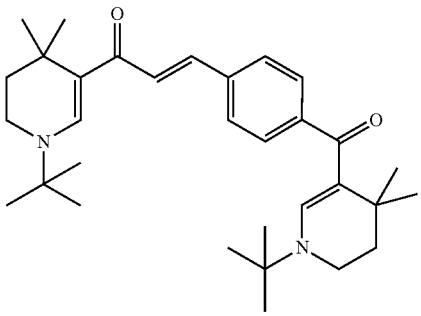

25
-continued
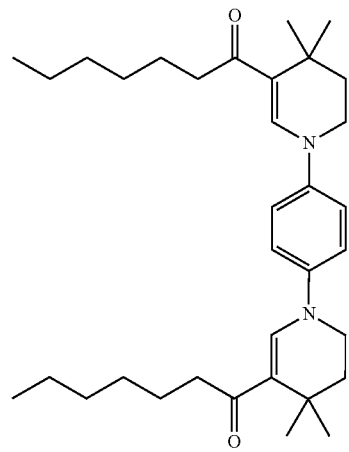
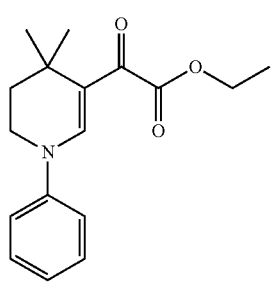
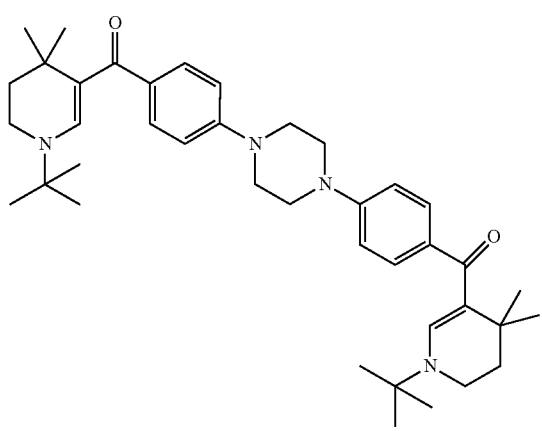
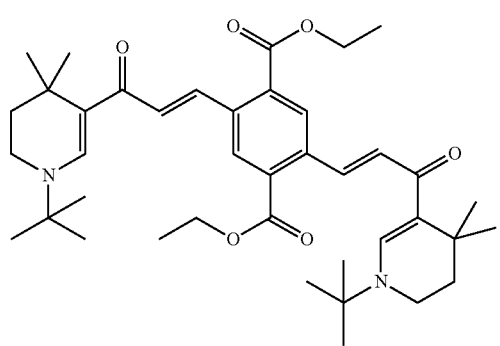
26
-continued
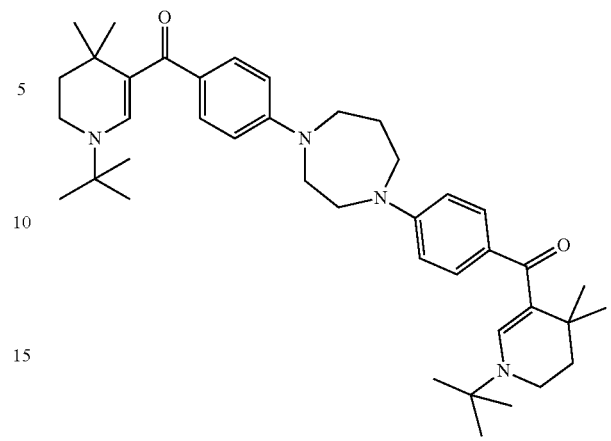
263
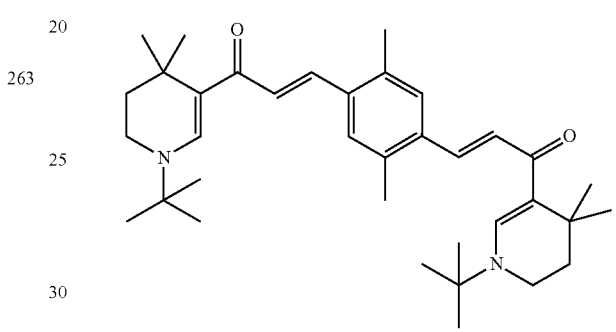
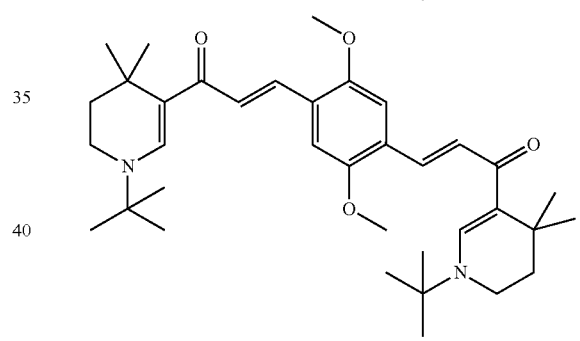
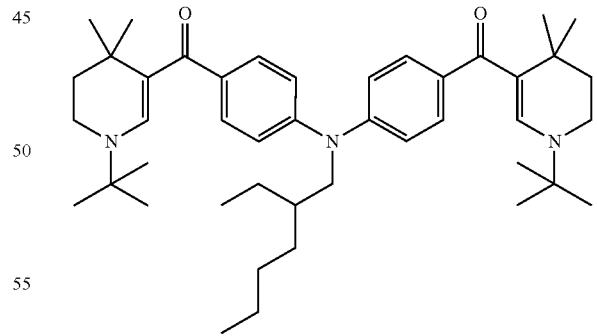
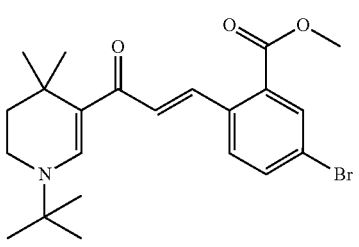

27
-continued
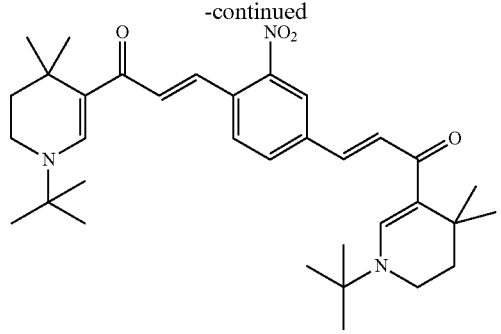
28
-continued
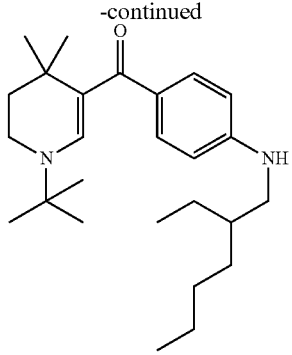
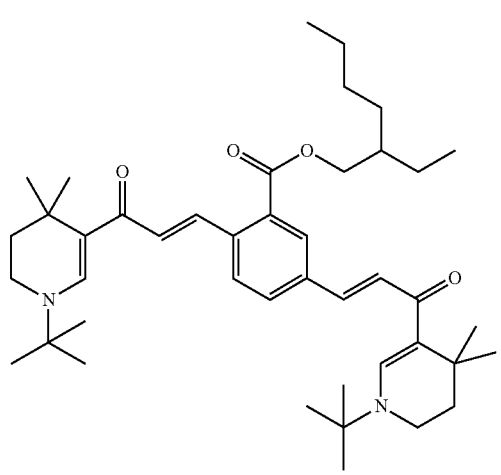
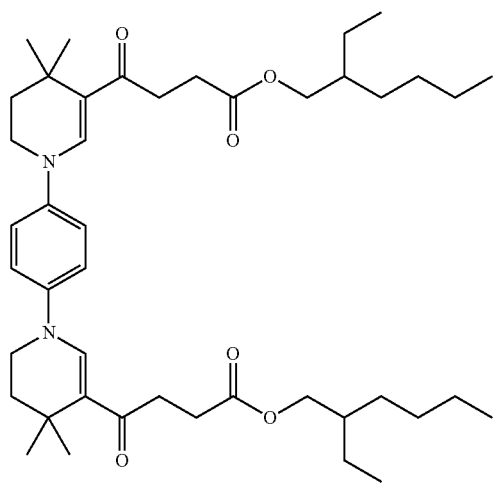
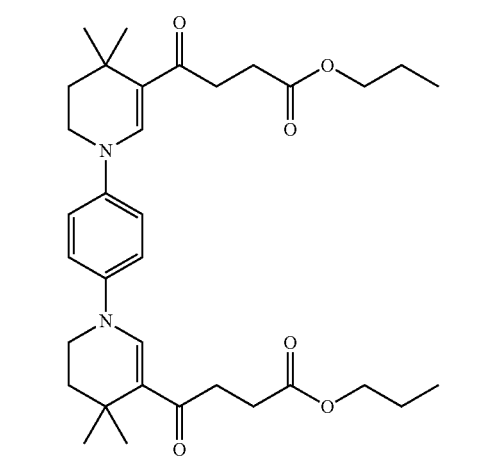
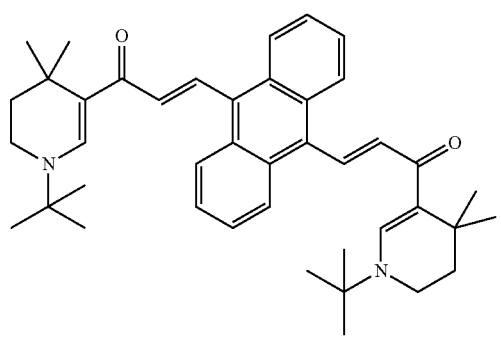
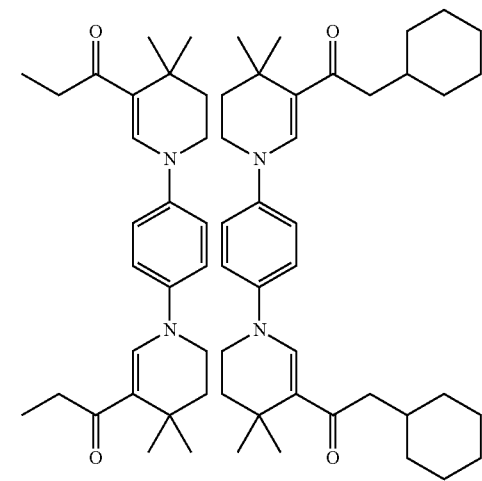

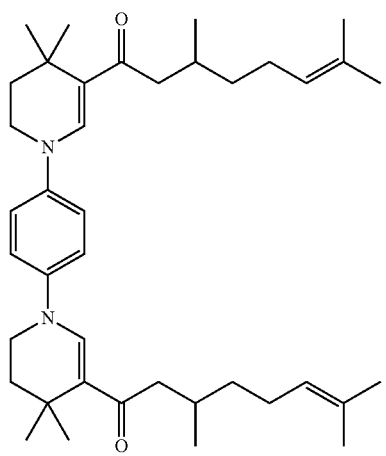
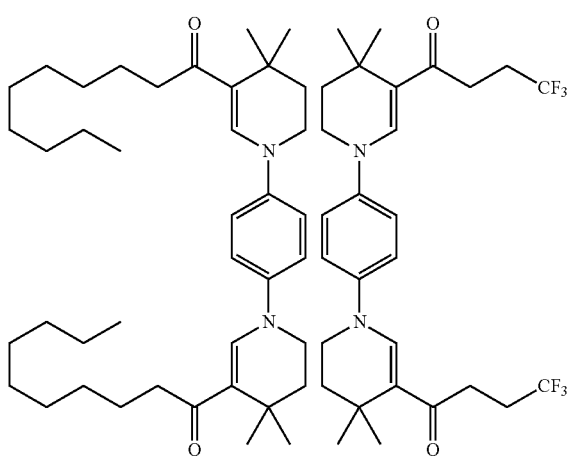
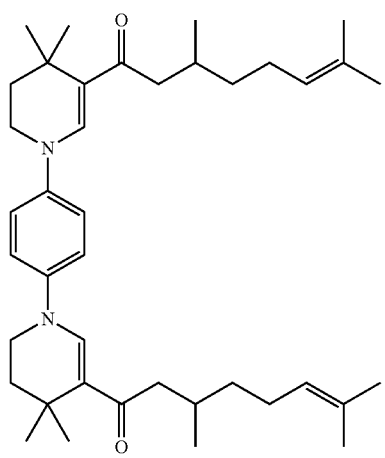
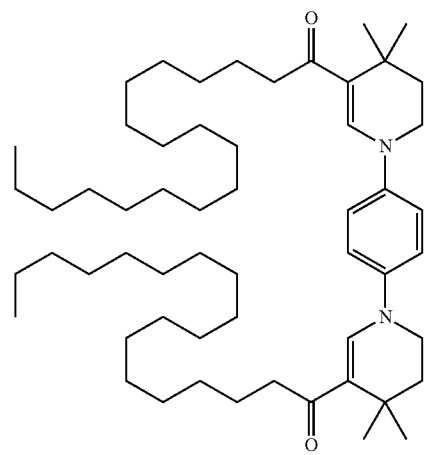
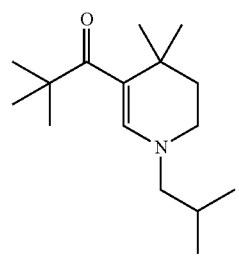
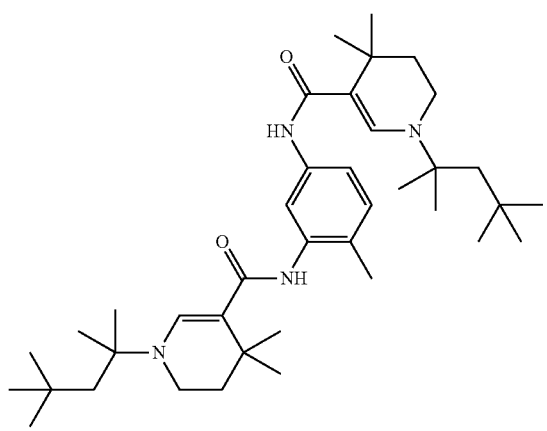
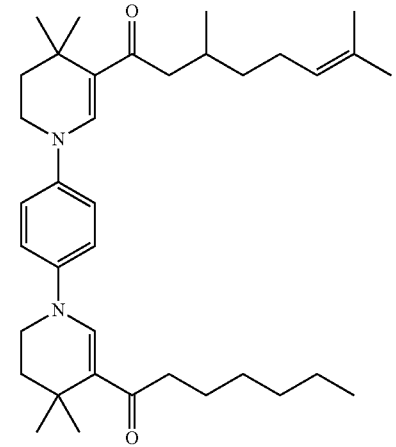

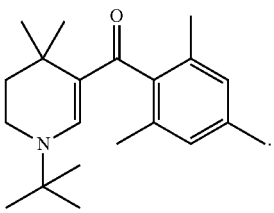

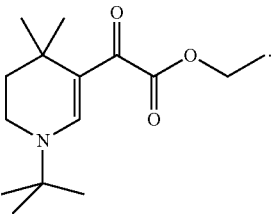

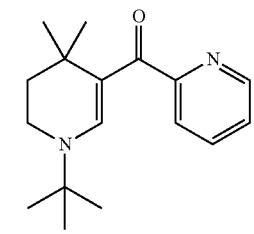

In one embodiment, the compound of formula V is not either of the below compounds:

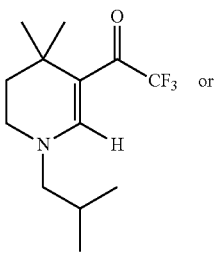

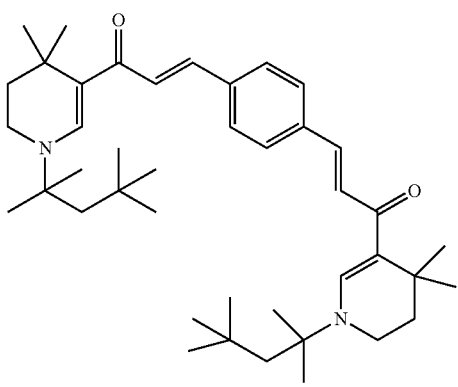

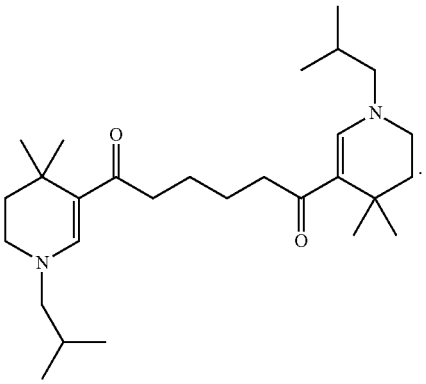

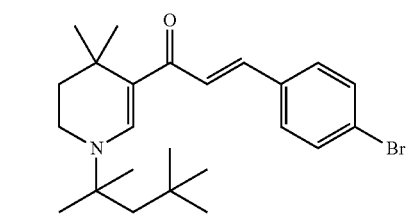

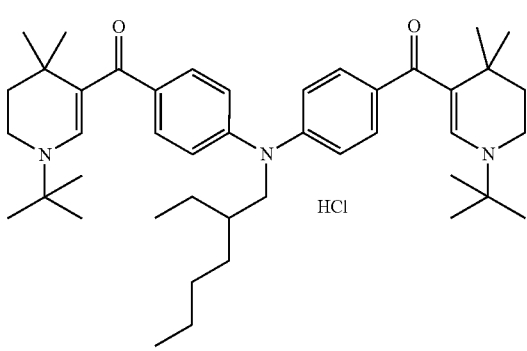

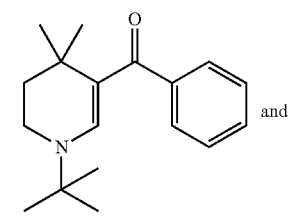

The compounds of formula V may demonstrate one or more advantages over the prior art including but not limited to improved absorbance, stability, solubility, increased molecular weight, desirable clogP, and effective absorbance in an alternate region of the electromagnetic spectrum i.e. they may provide access to a region of the spectrum not provided for by prior art compounds.

The compounds of the first aspect may be effective absorbers in the UV-A, UV-B and visible regions of the spectrum. The benefits of protection from UV light for humans and various materials are well known. The dangers of exposure to visible light have received less attention but are of potentially equally serious consequence. Visible light sensitivity, for example, is an important phenomenon in diseases such as porphyria, solar urticaria, and other idiopathic photodermatoses, such as polymorphous light eruption. Patients who undergo photodynamic therapy treatments also become sensitive to visible light for a few days because of the accompanying topical medications. Protection against visible light might also be important for darker skinned patients who have pigmentary disorders. Finally, visible light is thought to be a causative agent in age-related macular degeneration of the eye and so lenses and glasses offering protection in this range would be advantageous.

Organic sunscreen agents typically offer no protection against visible light, as their absorption spectrum is limited to UVB and UVA wavebands. Inorganic sunscreen agents, such as iron oxide, titanium dioxide, and zinc oxide can offer some visible light protection. However, the spectral protection of these agents varies according to their particle size. It is an advantage of the present invention that the variation in compound substitutions, particularly at the key R3 and R5 (R22 and R23 of formula V) ring substitution positions, provides for a range of absorptions and so a number of compounds presented herein represent effective absorbers in the visible light region. It is expected that the perceived importance of such absorbing compounds in an effective sunscreen, or otherwise light protective formulation, will only increase with realisation by the general public of the risks. Compounds of the present invention, or combinations thereof, can provide an effective solution. The results described herein indicate compounds which can be effective in absorbing in one or more of the UV-A, UV-B and visible light regions.

Referring now to terminology used generically herein, the term "alkyl" means a straight-chain or branched alkyl substituent containing from, for example, 1 to about 12 carbon atoms, preferably 1 to about 9 carbon atoms, more preferably 1 to about 6 carbon atoms, even more preferably from 1 to about 4 carbon atoms, still yet more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like. The number of carbons referred to relates to the carbon backbone and carbon branching but does not include carbon atoms belonging to any substituents, for example the carbon atoms of an alkoxy substituent branching off the main carbon chain.

The term "alkenyl," as used herein, means a linear alkenyl substituent containing at least one carbon-carbon double bond and from, for example, 2 to 6 carbon atoms (branched alkenyls are 3 to 6 carbons atoms), preferably from 2 to 5 carbon atoms (branched alkenyls are preferably from 3 to 5 carbon atoms), more preferably from 3 to 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term "alkynyl," as used herein, means a linear alkynyl substituent containing at least one carbon-carbon triple bond and from, for example, 2 to 6 carbon atoms (branched alkynyls are 3 to 6 carbons atoms), preferably from 2 to 5 carbon atoms (branched alkynyls are preferably from 3 to 5 carbon atoms), more preferably from 3 to 4 carbon atoms. Examples of such substituents include ethynyl, propynyl, isopropynyl, n-butynyl, sec-butynyl, isobutynyl, tert-butynyl, pentynyl, isopentynyl, hexynyl, and the like.

The term "alkylalkanoate" refers to an ester moiety being one that comprises up to 20 carbon atoms as a backbone and wherein the carbonyloxy component may be located anywhere along the 20 carbon backbone. The backbone may be substituted particularly with $C_1$ to $C_6$ alkyl or $C_1$ to $C_6$ alkoxy.

The term "cycloalkyl" refers to optionally substituted saturated mono-cyclic, bicyclic or tricyclic carbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

The term "aryl" refers to an unsubstituted or substituted aromatic carbocyclic substituent, as commonly understood in the art. It is understood that the term aryl applies to cyclic substituents that are planar and comprise $4n+2\pi$ electrons, according to Hückel's Rule.

The term "heteroaryl" refers to an aryl group containing from one or more (particularly one to four) non-carbon atom(s) (particularly N, O or S) or a combination thereof, which heteroaryl group is optionally substituted at one or more carbon or nitrogen atom(s). Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. "Substituted heteroaryl" means a heteroaryl having one or more non-interfering groups as substituents.

"Heterocyclic" or "heterocycle" refers to a non-aromatic ring having 5 to 7 atoms in the ring and of those atoms 1 to 4 are heteroatoms, said ring being isolated or fused to a second ring wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated. Non-limiting examples of heterocyclic include pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

"Alkanoyl" means alkanoyl groups of a straight or branched configuration and of the specified number of carbon atoms. By way of non-limiting example, alkanoyl may be selected from acetyl, propionoyl, butyryl, isobutyryl, pentanoyl and hexanoyl.

Whenever a range of the number of atoms in a structure is indicated (e.g., a $C_1$-$C_{20}$, $C_1$-$C_{12}$, $C_1$-$C_{10}$, $C_1$-$C_9$, $C_1$-$C_6$, $C_1$-$C_4$, or $C_2$-$C_{20}$, $C_2$-$C_{12}$, $C_2$-$C_{10}$, $C_2$-$C_9$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-20 carbon atoms (e.g., $C_1$-$C_{20}$), 1-12 carbon atoms (e.g., $C_1$-$C_{12}$), 1-10 carbon atoms (e.g., $C_1$-$C_{10}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkanoyl, etc.) referenced herein encompasses and specifically describes 1, 2, 3, 4, 5, 6, 7, 8, 9, 10, 11, 12, 13, 14, 15, 16, 17, 18, 19 and/or 20 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 1-18 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 2-18 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In any of the embodiments described the term "substituted' may refer to substitution with a group selected from alkyl, alkenyl, alkylalkanoate, aryl, alkylaryl, heteroaryl, heterocyclyl, alkynyl, aroyl, alkanone, cycloalkyl, cycloalkanone, cycloalkenyl, alkanoyl, alkanoyloxy, alkoxycarbonyl, carbamoyl, carboxyl, haloalkyl, N-alkyl, N-aryl and N-heterocyclyl. Each of these groups may themselves be substituted with the same or different groups.

compounds of the present invention. The isomers may be used either in pure form or in admixture with other isomers of the compounds described herein.

Compound Synthesis and Strategy

The synthesis of analogous compounds has previously been described by the applicant in PCT publications WO 2014/082124 and WO 2015/006803, the entire contents of which are hereby incorporated by reference. Similar approaches are used herein with, in the case of compounds of formula I and II, the halogenated $R_3$ position achieved, as desired, simply by selection of an appropriate acyl chloride, anhydride, or like reactant, as would be understood by a person of skill in the art. Briefly, a general approach to deliver the cyclic enaminoketones of the first aspect in large scale quantities has been developed by the applicant and is shown in Scheme 1 below:

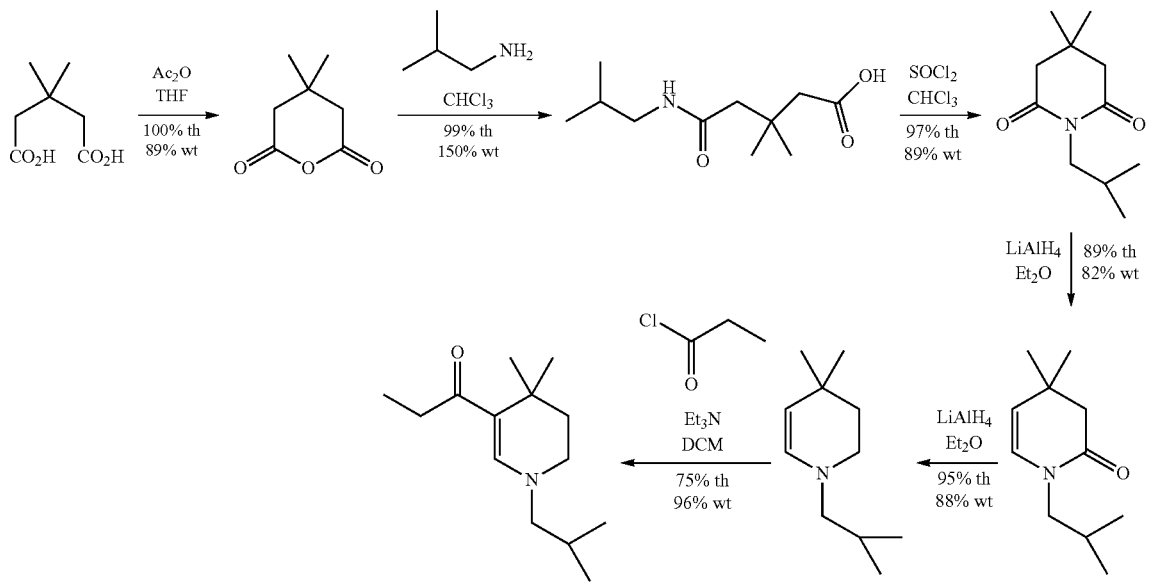

Scheme 1: Synthetic route to 1, 3, 4-substituted cyclic enaminoketones.

In particular embodiments of formula Ia, Ib or II, the substitution referred to may be any of substitution with fluorine to form a perfluoro moiety; substitution with a substituted or unsubstituted phenyl ring; and substitution with a 6-membered nitrogen heterocycle which may contain a double bond within the ring and may itself be substituted or unsubstituted.

In some embodiments of the first aspect, compounds with one or more chiral centers, or exhibiting some form of isomerism, are provided. The compounds disclosed herein as electromagnetic radiation absorbing agents may contain chiral centers, which may be either of the (R) or (S) configuration, or which may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention. Isomers may include geometric isomers. Examples of geometric isomers include, but are not limited to, cis isomers or trans isomers across a double bond. Other isomers are contemplated among the This approach allowed access to a wide range of cyclic enaminoketones with varying substituents. Modifications of the scheme and use of the intermediates to access a variety of products provides for a means to tailor the final product in terms of lipophilicity and absorbance maximum. By way of example, a wide range of amines could be employed at the second step to give a range of alkyl, alkenyl, aryl etc. groups on the ring opened compound. This means that the N-linked isobutyl group in Scheme 1 could be replaced with, for example tert-butyl, aryl, substituted aryl and the like in a convenient manner. The compounds of formula V may be synthesised in much this manner. Synthesis of select examples of compounds of formula V are provided in the experimental section.

To achieve the halogenated photostabilising group (at least one of the $R_a$, $R_b$ and the $R_3$ positions of formula Ia, Ib or II) the cyclic enamine may be reacted with the appropriate halogenated alkyl acyl chloride, anhydride or like reactant suitable for reaction with the doubly bonded carbon of the ring. This provides access to a wide range of stabilised compounds. When the desired acid chloride was not commercially available it could be prepared from the carboxylic acid as set out in the experimental section.

Surprisingly, it has been found that the use of fluorinated acyl chlorides or anhydrides, for example in trifluoroacetylation of the enamine ring results in higher synthetic yields than with the corresponding non-fluorinated acylation. In one instance, one of the compounds was obtained in 61% yield when trifluoroacetylated compared to less than 25% when acylated with a corresponding non-fluorinated acid chloride. Presumably this effect is also a result of the stabilisation of the ring discussed previously.

Further, it is an advantage of the present stabilised compounds of formula Ia, Ib or II that the increase in physical stability seen with a halogen, for example fluorine presented on at least one of the $R_a$, $R_b$ or $R_3$ positions, may be sufficient to both chemically and photochemically stabilise compounds of the invention which are provided with a primary amine substituent i.e. extending from the $R_5$ ring nitrogen position, such that they can now be more useful. Until now the use of 3° amines has generally been favoured to increase stability but, while effective for this task, this increases synthetic difficulty and production costs and limits the choice of groups which can be incorporated in this position. Stabilising the molecule sufficiently to allow the generation of a range of 1° amines at the $R_5$ ring nitrogen position allows for a greater choice of reagents, and hence groups to be tested at this position, and reduced production costs.

A number of compounds of the invention display an aryl or substituted aryl at the $R_5$ position. By way of example only, the below Scheme 2 shows one approach to obtaining such compounds. Again, such routes would be known to the skilled addressee and have been previously published by the applicant in the aforementioned PCT publications. The approach is a similar synthetic route to that shown in Scheme 1.

N-aryl enamines. One representative reaction is shown in Scheme 3 below.

Scheme 3: Trifluoroacetylation of an N-aryl enamine.

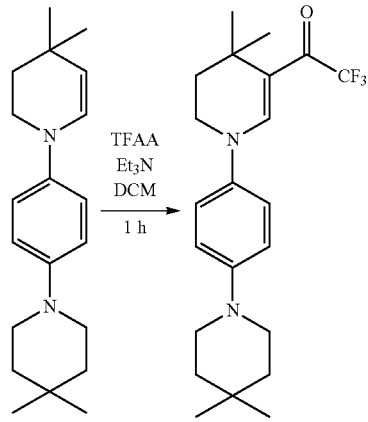

Further, a wide range of reagents similar to and including heptafluorobutyryl chloride (CAS#375-16-6) are readily available which would also increase the molecular weight of the synthesised compounds of formula I and II to be above 500, which is important for sunscreens as it is recognised that having a molecular weight greater than 500 reduces the risk of skin penetration and associated safety concerns.

Scheme 2: Synthetic route used to deliver N-phenyl derivatives.

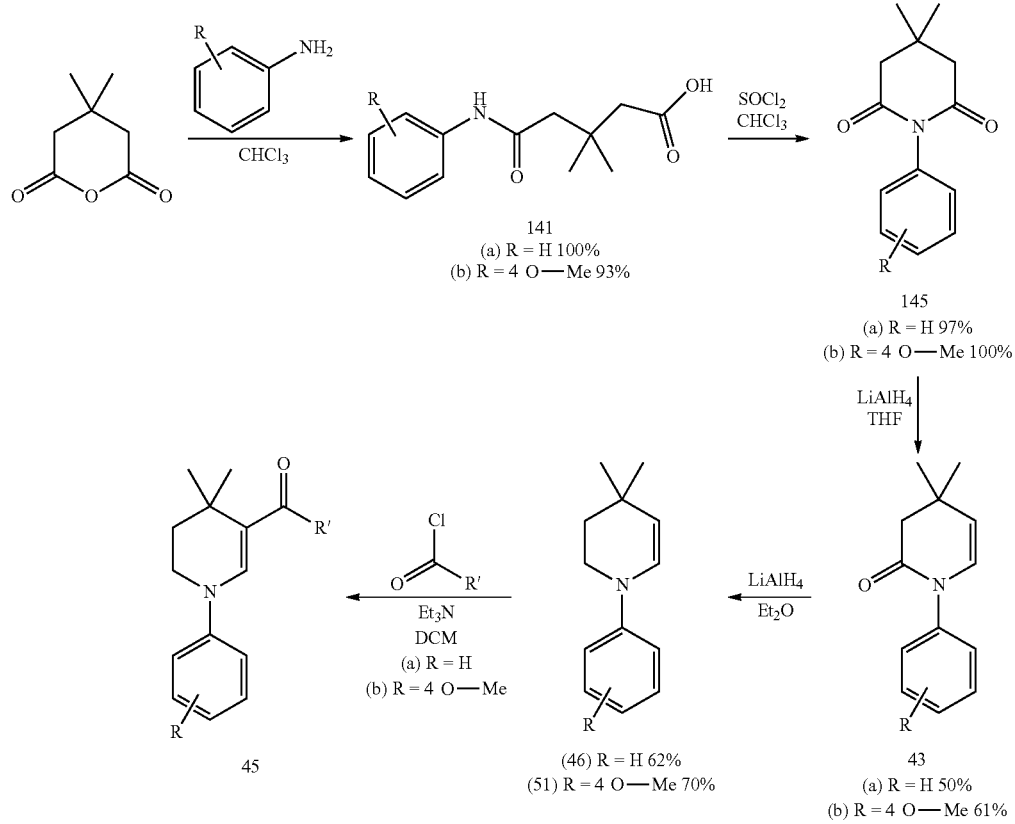

Trifluoroacetic anhydride (TFAA) was previously shown by the inventors to be effective for trifluoroacetylation of Diacid chlorides, such as hexafluoroglutaryl chloride for example, are also commercially available and could be used in the synthesis of dimeric compounds. Di-functionalised perfluoroacids are readily available or can be made to order and allow for the formation of compounds comprising two cyclic enamine structures linked by the acid backbone. The person of skill in the art would be well aware of such reagents and the guidance provided herein would leave them with a wide variety of reactants at their fingertips to synthesise further compounds not explicitly disclosed herein with undue experimentation.

As a further example of the synthesis of compounds of the first aspect, the below scheme 4 shows the synthetic pathway used to obtain fluorinated compounds 159 and 160:

Scheme 4: Synthesis of compounds 159 and 160.

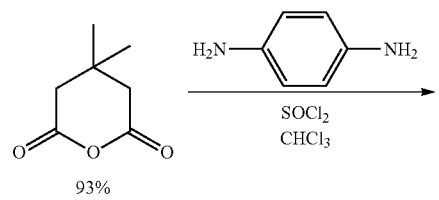

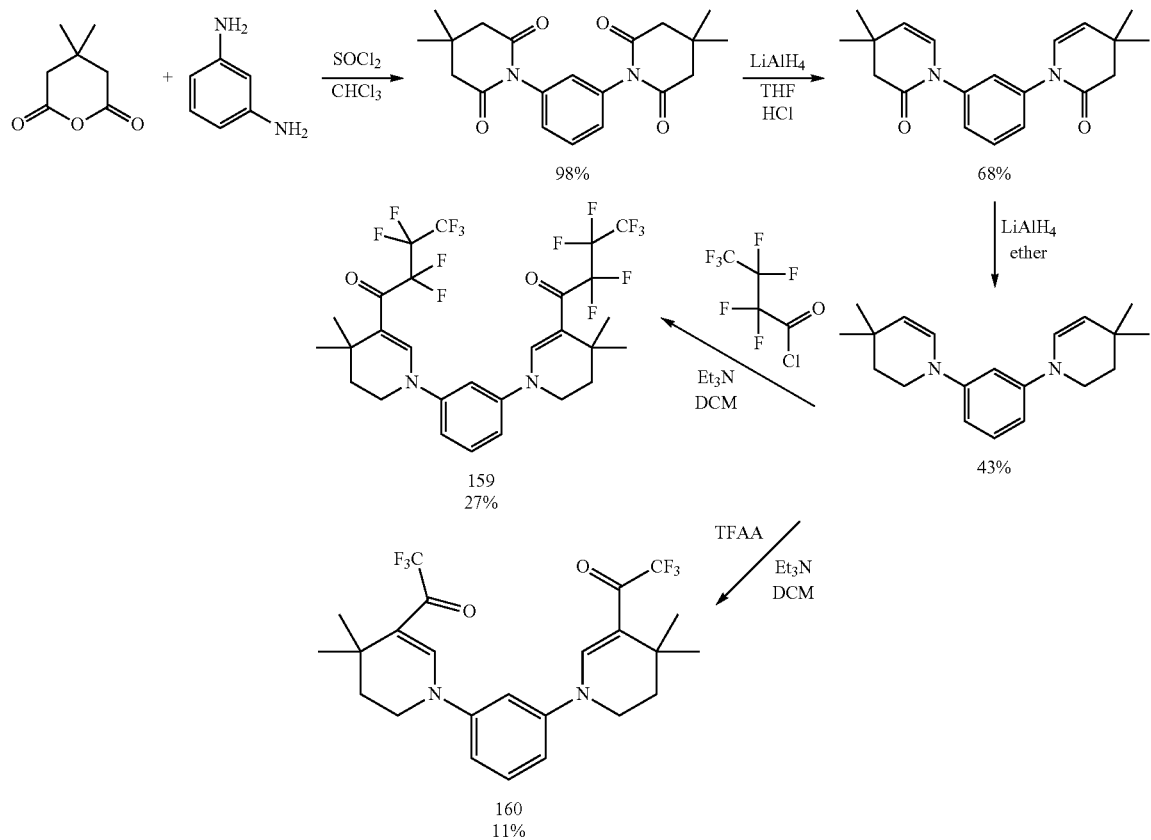

As a still further example of the synthesis of compounds of the first aspect, the below scheme 5 shows the synthetic pathway used to obtain the cyclic enamine dimer compound 129:

Scheme 5: Synthesis of compound 129

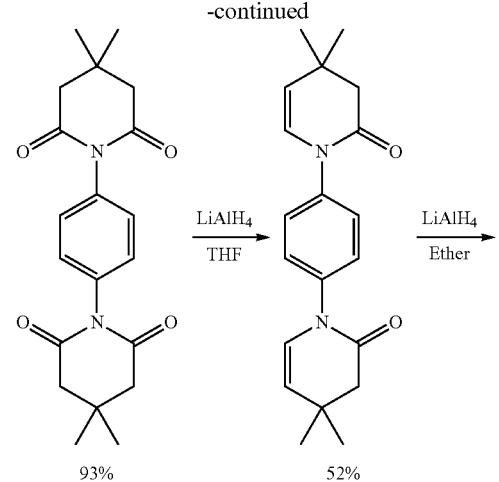

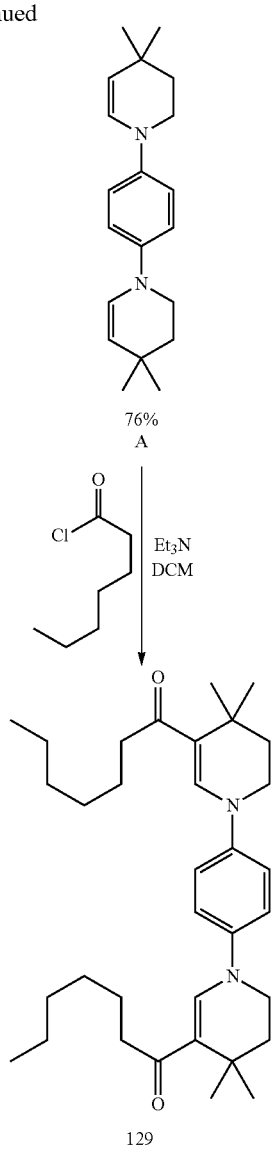

129

According to a second aspect of the present invention there is provided a composition comprising a compound of the first aspect, or a salt thereof, and a suitable carrier.

In one embodiment, the compounds may provide for improved solubility or stability in standard compositions, including sunscreen compositions. For example, compounds 152, 153, 154, 155, and 157 are readily soluble in standard commercial sunscreen formulations. Such solubility may be measured by generating, for example, a 3% solution of the relevant compound in 2:1:1 EtOH:capric/caprylic triglyceride:C12-C15 alkyl benzoate.

In one embodiment, the composition is a sunscreen composition. The sunscreen composition may be suitable for protection from one or more of UV-A, UV-B and visible light.

The sunscreen composition may contain dispersing agents, emulsifiers or thickening agents to assist in applying a uniform layer of the active compounds. Suitable dispersing agents for the sunscreen formulations include those useful for dispersing organic UV and visible light absorbing agents in a water phase, oil phase, or part of an emulsion, including, for example, chitosan.

Emulsifiers may be used in the sunscreen composition to disperse one or more of the compounds or other components of the sunscreen composition. Suitable emulsifiers include conventional agents such as, for example, ethoxylated alcohols (oleth-2, oleth-20 etc.), glycerol stearate, stearyl alcohol, cetyl alcohol, dimethicone copolyol phosphate, hexadecyl-D-glucoside, octadecyl-D-glucoside, cetearyl alcohol and dicetyl phosphate and ceteth-10-phosphate (Crodafos™ CES), one or more ethoxylated esters of natural derivatives, e.g. polyethoxylated esters of hydrogenated castor oil; or a silicone emulsifier such as silicone polyol; a free or ethoxylated fatty acid soap; an ethoxylated fatty alcohol; a free or ethoxylated sorbitan ester, an ethoxylated fatty acid; or an ethoxylated glyceride.

Emolients may be used in the sunscreen composition including cetyl esters, such as cetyl ethylhexanoate, isostearyl neopentanoate, diisopropyl sebacate, coconut oil and silicones.

Humectants may be used including glycols such as propylene glycol and butylene glycol as well as glycerine.

Rheology modifiers such as various Carbopol® acrylate polymeric compounds, alkyl acrylates as well as neutralisers and preservatives as are standard in the art.

Thickening agents may be used to increase the viscosity of the sunscreen composition. Suitable thickening agents include glyceryl stearate, carbomers, acrylate/acrylonitrile copolymers, xanthan gum and combinations of these. The amount of thickener within the sunscreen composition, on a solids basis without water, may range from about 0.001 to about 5%, preferably from 0.01 to about 1% and optimally from about 0.1 to about 0.5% by weight.

Minor optional adjunct ingredients for the sunscreen composition may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone (PVP), polyvinylpyrrolidone/vinylacetate, PVP/Eicosene copolymer and adipic acids/diethylene glycol/glycerine crosspolymer etc. Waterproofing agents may be present at levels of from about 0.01 to about 10% by weight.

There is considerable knowledge in the art in terms of sunscreen formulations and standard texts and journal articles may also provide guidance. One such text which may prove useful is *The Chemistry and Manufacture of Cosmetics*. An appropriate article to refer to may be *Cosmetics & Toiletries*, vol. 116, No. 9, September 2001 and Tanner. P. R., Dermatol. Clin. 2006 January; 24(1):53-62. These articles and textbook are incorporated herein in their entirety by way of reference.

Eusolex® UV-Pearls® (supplied commercially by Merck) may provide for the present absorbing compounds to be encapsulated in micro-capsules allowing for alternative options in formulation. Such encapsulation may provide for a reduced dermal uptake, lower allergy potential, and further improved photostability. The micro-encapsulation technology employed entraps the compounds in a sol-gel silica glass. Merck supplies such products as aqueous dispersions containing approximately 37% (w/w) of the UV absorber.

The white liquids contain Eusolex® UV-Pearls® of about 1.0 μm diameter on average which are transparent when applied to the skin.

Therefore, in one embodiment, the compounds of the first aspect are present in a composition as encapsulated compounds. The encapsulation may be by any known method of encapsulation but preferably is by a sol gel encapsulation approach. Suitably, the encapsulation is a silica-based sol gel encapsulation. For compounds with highly desirable absorption properties but less than optimal photostability, encapsulation may improve the photostability into commercially acceptable territory.

The sunscreen compositions can additionally contain one or more further UV-protective substances, e.g. triazines, 1,3-diketones, such as avobenzone, oxanilides, triazoles or amides containing vinyl groups or cinnamides. Such protective substances are described, for example, in GB-A-2,286,774 or alternatively are known from Cosmetics & Toiletries (107), 50 et seq. (1992).

The compositions may contain 0.1 to 15, preferably 0.5 to 10% by weight, based on the total weight of the composition, of a compound of the first aspect. The compositions can be prepared by physical mixing of the compounds with the auxiliary by the usual methods, such as, for example, by simply stirring the individual components together. The compositions can be formulated as a water-in-oil or oil-in-water emulsion, as an oil-in-alcohol lotion, as a vesicular dispersion of an ionic or non-ionic amphiphilic lipid, as a gel, solid stick or as an aerosol formulation. As a water-in-oil or oil-in-water emulsion, any compatible auxiliary preferably contains 5 to 50% of an oil phase, 5 to 20% of an emulsifier and 30 to 90% of water. The oil phase can in this case contain any oil suitable for cosmetic formulations, e.g. one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

In one embodiment, the sunscreen composition may comprise more than one compound of formula Ia, Ib, II and/or V or a compound of formula Ia, Ib, II and/or V and a known UV absorbing sunscreen agent or protective agent such as avobenzone, EHT, octinoxate and octocrylene.

The protective agent may be an additive, such as octocrylene and like compounds, which have protective effects on the compounds of the invention. While showing modest UV absorption itself, octocrylene is primarily used in sunscreen formulations due to the stabilising and protective effect it has on other UV absorbing actives. Current understanding suggests that the energy levels of such stabilisers need to be matched with the UV/light absorbing active to allow efficient stabilisation and so it cannot be assumed that protective agents such as octocrylene would work with any particular class of absorbing compounds. Due to the lack of understanding of the protective relationship, and hence lack of reliable prediction, it is necessary to test the compounds with the protective additive and see if the benefit is obtained. Advantageously, it has been found by such testing that the present compounds of formula Ia, Ib, II and/or V are appropriately 'matched' with octocrylene and so receive the additional protective benefit. Further protective agents which may be present in the composition include MBC, MBBT, BEMT, DHHB, Diethylhexyl 2,6 Naphthalate (DEHN, CORAPAN® TQ), Diethylhexyl Syringylidene Malonate (DESM, Oxynex® ST), and Benzotriazolyl Dodecyl p-cresol (TINOGARD® TL).

In one alternative embodiment, the composition is a coating composition, a plastics composition or a paint composition. UV protective paint or general coating compositions can be useful in external applications such as in automotive paints, masonry and timber paints and UV protective compositions for boats and other marine applications.

The paint composition may contain a diluent or solvent such as water, petroleum distillate, an esters, a glycol ether, a binder or film forming component including include synthetic or natural resins such as alkyds, acrylics, vinylacrylics, vinyl acetate/ethylene (VAE), polyurethanes, polyesters, melamine resins, epoxy, or oils, and may comprise a pigment or dye to provide colouration and/or other optional additives such as catalysts, thickeners, stabilizers, emulsifiers, texturizers, adhesion promoters, UV stabilizers, flatteners (de-glossing agents), fungicides, flow control agents, surfactants, and rheology modifiers.

In a further alternative embodiment, the composition may be a glass or plastic film-forming composition. Such compositions may be useful in forming UV and/or visible light protective glass or plastic films useful to prevent UV and/or visible light damage to the enclosed material. They may be useful in forming or coating: automotive glass, architectural glass and plastics, such as PVC, used in similar applications. The compositions may, in one embodiment, result in UV and/or visible light protective ophthalmic lenses including corrective contact lenses and eyeglasses. Such compositions are known in the art but have not comprised the compounds of the present invention to this point.

In further embodiments, the composition comprising at least one compound of formula Ia, Ib, II and/or V, or a salt thereof, may be an industrial formulation. Such formulations may form components of dishwashing liquids, gels or tablets, food packaging, coatings for signage and the like.

Such formulations may comprise a range of emulsifiers, silicates, bleaches, activators, catalysts, metal care agents, alkalinity agents, polymeric dispersants, anti-redisposition agents, sulfonated or carboxylated polymers, enzymes, ionic surfactants and non-ionic surfactants, as are known in the art.

Detergent active components which may be selected from bleach, bleach activator, bleach catalyst, surfactants, alkalinity sources, enzymes, polymeric dispersants, anti-corrosion agents (e.g. sodium silicate) and care agents. Highly preferred detergent components include a builder compound, an alkalinity source, an anti-redeposition agent, a sulfonated polymer, an enzyme and an additional bleaching agent.

The bleach is preferably selected from inorganic peroxides inclusive of perborates and percarbonates, organic peracids inclusive of preformed monoperoxy carboxylic acids, such as phthaloyl amido peroxy hexanoic acid and di-acyl peroxides Builders suitable for use in such an industrial detergent composition include builders which form water-soluble hardness ion complexes (sequestering builders) such as citrates and polyphosphates e.g. sodium tripolyphosphate and sodium tripolyphosphate hexahydrate, potassium tripolyphosphate and mixed sodium and potassium tripolyphosphate salts and builders which form hardness precipitates (precipitating builders) such as carbonates e.g. sodium carbonate.

Other suitable builders include amino acid based compounds or a succinate based compound. Examples of suitable amino acid based compounds include MGDA (methylglycine-diacetic acid), and salts and derivatives thereof and GLDA (glutamic-N,N-diacetic acid) and salts and derivatives thereof. GLDA (salts and derivatives thereof) is especially preferred according to the invention, with the tetrasodium salt thereof being especially preferred. Particular suitable builders include for example, aspartic acid-N-monoacetic acid (ASIA), aspartic acid-N,N-diacetic acid (ASDA), aspartic acid-N-monopropionic acid (ASMP), iminodisuccinic acid (IDA), N-(2-sulfornethyl) aspartic acid (SMAS), N-(2-sulfoethyl) aspartic acid (SEAS), N-(2-sulfomethyl)glutamic acid (SMOL), N-(2-sulfoethyl)glutamic acid (SEOL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfornethyl-N,N-diacetic add (SMDA) and alkali metal salts or ammonium salts thereof The detergent and cleaning compositions herein can comprise traditional detergency components and can also comprise organic solvents having a cleaning function and organic solvents having a carrier or diluent function or some other specialised function. The compositions will generally be built and comprise one or more detergent active components which may be selected from bleaching agents, surfactants, alkalinity sources, enzymes, thickeners (in the case of liquid, paste, cream or gel compositions), anti-corrosion agents (e.g. sodium silicate) and disrupting and binding agents (in the case of powder, granules or tablets).

In yet a further embodiment, the composition may be a treatment for hair of a mammal, such as a human or companion animal. The hair care composition may be a colouring or other cosmetic composition or may be a UV protective composition specifically designed for hair application. The composition may directly protect the hair from UV damage or the compound(s) of the first aspect contained therein may also provide UV protection to dyes or other components of the hair treatment composition. Dyes and other components which may be included in the composition include anionic and/or cationic surfactants, fragrances, pest repellents, vitamins, sunscreens and cooling agents are well known in the art and it is envisaged that the composition would comprise one or more compounds of the first aspect along with one or more such components and a suitable carrier.

A third aspect of the present invention resides in the use of a compound of the first aspect, or a salt thereof, as an electromagnetic radiation absorbing compound.

A fourth aspect of the present invention resides in a method of protecting a surface or tissue from electromagnetic radiation including the step of applying a compound of the first aspect to the surface or tissue.

Preferably, the use of the third embodiment or the method of the fourth aspect has the compound as a component of a sunscreen composition. The compound of formula Ia, Ib, II and/or V may be present in the sunscreen composition with a range of standard formulation agents including water, various emulsifiers, stabilisers and surfactants.

Alternatively, the use of the third embodiment or the method of the fourth aspect has the compound as a component of a coating composition. The compound of formula Ia, Ib, II and/or V may be present in the coating composition with a range of standard formulation agents including, one or more the agents described above. The coating composition may be a paint, staining, UV and/or visible light protective, tinting, marine protection or polymeric matrix formulation wherein the compound of formula Ia, Ib, II and/or V provides UV and/or visible light protective or additional UV and/or visible light protective properties to the formulation.

For example, the coating composition may be a paint formulation for the exterior of a building, marine vessel or for exposed timber structures. The coating composition may also be a matrix coating for signage and the like which are exposed to the suns rays for extended periods of time and which display information which it is desirable to protect from fading.

Further, the use of the third embodiment or the method of the fourth aspect may employ the compound of formula Ia, Ib, II and/or V as a component of a UV and/or visible light protective glass and/or UV and/or visible light protective polymeric film. The glass may be prepared in a manner standard in the industry. The polymeric film may be chosen from a range of standard film materials such as polyolefin-based films. The compounds of the present invention may be incorporated by cross-liking during film formation or may be associated with the film forming compounds, such as loosely held within the polymeric matrix.

In one embodiment, the use of the third embodiment or the method of the fourth aspect may employ the compound of formula Ia, Ib, II and/or V as a component of a packaging and/or photobleachable and/or light exposure indicating material. The compounds of the invention may have their colour altered by exposure to UV and/or visible light. They may change from colourless to exhibit a colour or vice versa. One such non-limiting example is compound 94 disclosed herein which goes from bright yellow to colourless when exposed to irradiation. Prior art compounds typically become more coloured on UV exposure, not less, and so this photobleaching phenomenon could be exploited for indication/detection purposes.

In one embodiment, the use of the third embodiment or the method of the fourth aspect may have the compound in or on an ophthalmic lens. This may be in terms of the UV and/or visible light absorbing compounds being cast in a lens formulation where the absorber is added to the bulk lens monomer prior to casting. Alternatively, the UV and/or visible light absorbing compound may be included as part of a coating layer or via imbibition. The lens may be a glass or plastic lens.

Plastic lenses may be tinted by dipping them in a heated soluble dye comprising the UV and/or visible light absorbing compounds. This dye penetrates a uniform distance into the lens surfaces, providing a tint of uniform colour and transmittance and incorporating the UV and/or visible light absorbing compound. Glass lenses may be tinted by the addition of a chemical compound to the molten glass. The UV and/or visible light absorbing compound, if stable under those conditions, may be added in this process.

Some glass lenses are tinted by the application of a coating to one or both lens surfaces. These coatings consist of a thin layer of a coloured glass compound or a metal oxide that is applied using a vacuum deposition process. The UV and/or visible light absorbing compounds of the invention may be incorporated during this standard process.

In embodiments wherein the UV and/or visible light absorbing compound is included in the lens during formation of same it may be co-polymerised with a lens forming monomer. Many lens-forming monomers are known in the art and include both acrylic and silicone-containing monomers, among others. Non-limiting examples of preferred lens-forming monomers are 2-phenylethyl methacrylate; 4-phenylbutyl methacrylate; 5-phenylpentyl methacrylate;

2-benzyloxyethyl methacrylate; and 3-benzyloxypropyl methacrylate; and corresponding acrylates thereof.

The present compounds may also be used in the formation of plastic materials whereby their presence within the plastics matrix, either in the sense of being captured therein or being chemically bonded to the plastics backbone, imparts UV and/or visible light protective properties.

Therefore, it will be appreciated that the present compounds may be electromagnetic radiation absorbing molecules for human and material photo protection applications, including as components of coating compositions, glass compositions, plastics compositions, film-forming compositions, paint compositions; components of or coatings for lenses and eyeglasses; surface coatings for automobiles, timber, masonry, metals, plastics and glass; and components of compositions for marine applications.

A fifth aspect of the present invention resides in a method of improving the stability of a compound to electromagnetic radiation comprising the step of providing the compound with a photostability tag comprising a halogen or halogen-containing substituent.

The halogen or halogen-containing substituent may be any substituent as previously defined for $R_3$ of formula Ia, Ib or II.

The compound being stabilised may be any compound known to absorb in the visible light and UV regions of the electromagnetic spectrum.

One embodiment of the fifth aspect resides in a method of improving the stability of a compound selected from the group consisting of $C_2$ to $C_{20}$ alkenyl, $C_2$ to $C_{20}$ alkynyl, aryl, heteroaryl, aroyl, $C_2$ to $C_{12}$ alkenone, $C_5$ to $C_7$ cycloalkenyl, $C_4$ to $C_7$ cycloalkenone, N-aryl, N-heterocyclyl and heterocyclic all of which groups may be substituted or unsubstituted, or a salt thereof, comprising the step of providing the compound with the below group:

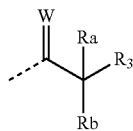

wherein, the dashed line represents the bond to the compound;

W is selected from O, S, N and C; and $R_a$, $R_b$ and $R_3$, when present, are independently selected from the group consisting of hydrogen, halo, $C_1$ to $C_{20}$ alkyl, $C_2$ to $C_{20}$ alkenyl, $C_2$ to $C_{20}$ alkynyl, aryl, heteroaryl, aroyl, $C_2$ to $C_{12}$ alkanone, $C_5$ to $C_7$ cycloalkyl, $C_4$ to $C_7$ cycloalkanone, $C_5$ to $C_7$ cycloalkenyl, $C_2$ to $C_{12}$ alkanoyl, $C_2$ to $C_{12}$ alkanoyloxy, $C_2$ to $C_{12}$ alkoxycarbonyl, $C_2$ to $C_{12}$ carbamoyl, $C_2$ to $C_{12}$ carboxyl, haloalkyl, N-alkyl, N-aryl, N-heterocyclyl and heterocyclic, all of which groups may be substituted or unsubstituted, or $R_b$ and $R_3$ may together form a phenyl ring or heteroaryl ring each of which is optionally substituted with at least one halogen or halogen-containing group.

In one embodiment at least one of $R_a$, $R_b$ and $R_3$ is a halogen.

In one embodiment, the compound is a compound corresponding to A of formula Ib.

In one embodiment of the fifth aspect the invention resides in a method of improving the stability of a compound, or a salt thereof, comprising the step of providing that the compound is converted from one of formula IIIa to one of formula II:

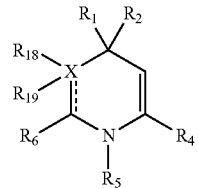

formula IIIa wherein the dotted line may be a bond and X, W, $R_1$, $R_2$, $R_3$, $R_4$, $R_5$, $R_6$, $R_{18}$ and $R_{19}$ are all as previously defined for formula II.

The conversion will ensure that at least, preferably two of the bonds on the non-ring carbon alpha to the carbon bonded to W will be a halogen, preferably fluorine.

The conversion may not be a direct conversion of the compound of formula III but rather may be a step in the synthesis of the compound of formula II whereby the formation of the compound of formula III is effectively avoided.

In any of the embodiments of the fifth aspect, X, W, $R_a$, $R_b$, $R_1$, $R_2$, $R_3$, $R_4$, $R_5$, $R_6$, $R_{18}$ and $R_{19}$ are all as previously defined for any embodiment of the first aspect.

The invention will now be described but it is in no way limited to the following Examples.

EXPERIMENTAL

Example 1

General Procedures for Fluorinated Acid Chloride Preparation

Fluorinated (or otherwise halogenated) acid chlorides could be prepared using one of two alternative methods.

Method 1

A solution of the fluorinated carboxylic acid (250 mg, 2.5 mmol) in DCM (5 mL) was treated with DMF (1 drop) followed by a solution of oxalyl chloride (209 µL, 2.4 mmol) in DCM (2.5 mL). The solution was then stirred at room temperature for 1 hour and used directly with no further purification.

Method 2

A solution of the fluorinated carboxylic acid (502 mg, 2.53 mmol) in thionyl chloride (10 mL) was treated with DMF (1 drop) and heated at reflux for 18 hours. The reaction mixture was then evaporated in-vacuo and the crude material dissolved in DCM and evaporated in-vacuo; this was repeated once more to afford the crude compound which could be used without further purification.

General Synthetic Approaches and Compound Characteristics

The following, table 1, provides a general synthetic guide for a number of specific compounds of the first aspect, both of formula I/II and formula V. The general guide refers to synthetic approaches discussed previously and other functional group transformation reaction which are well known to persons skilled in the art of synthetic organic chemistry.

TABLE 1

Compound data and synthetic approach for compounds.

| Structure and compound number | Clog P | λmax nm | λcrit nm | ε | E (1%, 1 cm) | General Synthetic Approach |
|---|---|---|---|---|---|---|
| 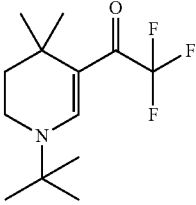 [SMILES: CC1(C)CCN(C(C)(C)C)C=C1C(=O)C(F)(F)F] 98 | 3.97 | 315 | 331 | 36298 | 1380 | Enamine formation followed by acylation |
| 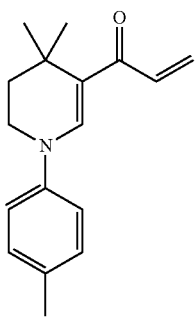 [SMILES: C=CC(=O)C1=CN(c2ccc(C)cc2)CCC1(C)C] 100 | 5.16 | 348 | 377 | 26657 | 1045 | Enamine formation followed by acylation |
| 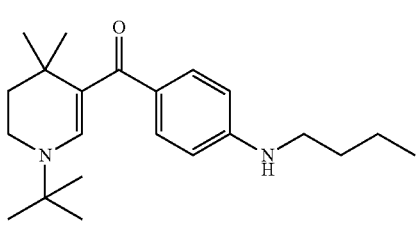 [SMILES: CCCCNc1ccc(C(=O)C2=CN(C(C)(C)C)CCC2(C)C)cc1] 102 | 6.71 | 316 | 360 | 21545 | 628 | Enamine formation followed by acylation then Pd catalysed amination |
| 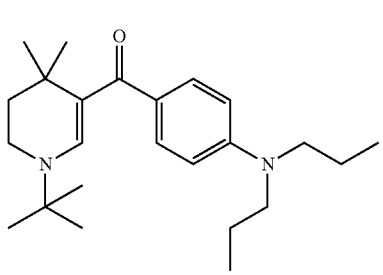 [SMILES: CCCN(CCC)c1ccc(C(=O)C2=CN(C(C)(C)C)CCC2(C)C)cc1] 103 | 7.66 | 315<br>342 | 365 | 19443<br>18994 | 525<br>513 | Enamine formation followed by acylation then Pd catalysed amination |
| 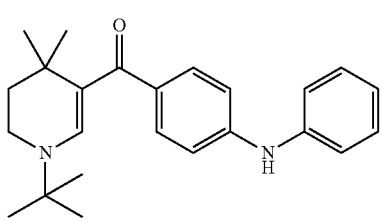 [SMILES: CC1(C)CCN(C(C)(C)C)C=C1C(=O)c1ccc(Nc2ccccc2)cc1] 104 | 7.26 | 315 | 361 | 26695 | 737 | Enamine formation followed by acylation then Pd catalysed amination |

TABLE 1-continued
Compound data and synthetic approach for compounds.
| Structure and compound number | Clog P | λmax nm | λcrit nm | ε | E (1%, 1 cm) | General Synthetic Approach |
|---|---|---|---|---|---|---|
| 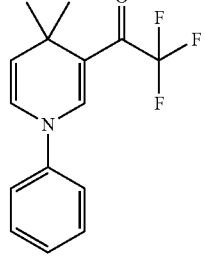 105 | 3.86 | 384 | 391 | 7393 | 263 | Enamine formation followed by acylation. |
| 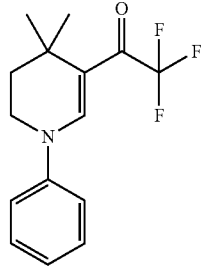 [SMILES: CC1(C)CCN(c2ccccc2)C=C1C(=O)C(F)(F)F] 106 | 4.24 | 335 | 357 | 29040 | 1033 | Enamine formation followed by acylation |
| 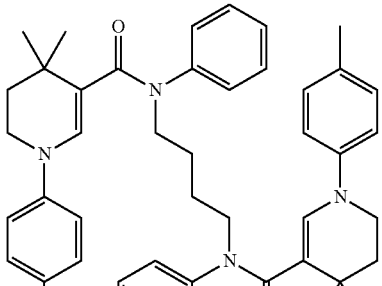 107 | 13.07 | 325 | 346 | 42215 | 608 | Enamine formation followed by reaction with isocyanate. Final step alkylation of 1° amide |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 108 | 8.41 | 341 | 363 | 60770 | 1051 | Enamine formation followed by acylation |
| 109 | ND | 317<br>340 | 364 | 43630<br>45584 | 638<br>667 | Enamine formation followed by acylation then Pd catalysed amination |
| 110 | 7.88 | 386 | 390 | 36404 | 705 | Enamine formation followed by acylation then Heck reaction |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 111 | 8.44 | 343 | 365 | 53548 | 923 | Enamine formation followed by acylation |
| 112 | 7.88 | 360 | 386 | 20388 | 395 | Enamine formation followed by acylation then Heck reaction |
| 113 | 16.70 | 326 | 352 | 46937 | 567 | Enamine formation followed by reaction with isocyanate. Final step alkylation of 1° amide |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 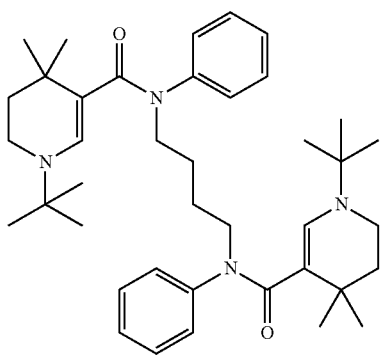 [SMILES: CC1(C)CCN(C(C)(C)C)C=C1C(=O)N(CCCCN(C(=O)C1=CN(C(C)(C)C)CCC1(C)C)c1ccccc1)c1ccccc1] 114 | 11.24 | 312 | 357 | 22166 | 354 | Enamine formation followed by reaction with isocyanate. Final step alkylation of 1° amide |
| 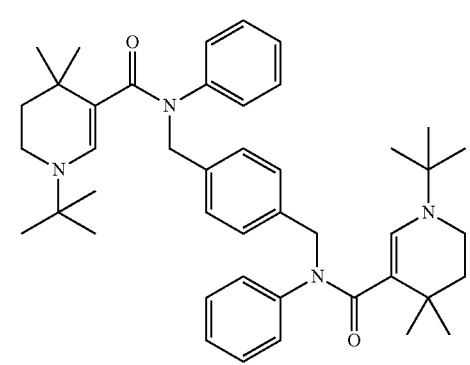 [SMILES: CC1(C)CCN(C(C)(C)C)C=C1C(=O)N(Cc1ccc(CN(C(=O)C2=CN(C(C)(C)C)CCC2(C)C)c2ccccc2)cc1)c1ccccc1] 115 | 12.17 | 314 | 365 | 26421 | 391 | Enamine formation followed by reaction with isocyanate. Final step alkylation of 1° amide |
| 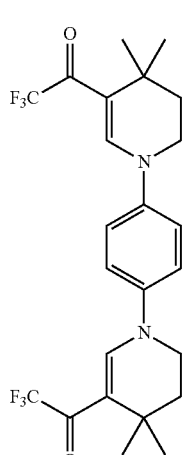 116 | 6.34 | 367 | 386 | 54658 | 1120 | Enamine formation followed by acylation |

TABLE 1-continued
Compound data and synthetic approach for compounds.
| Structure and compound number | Clog P | λmax nm | λcrit nm | ε | E (1%, 1 cm) | General Synthetic Approach |
|---|---|---|---|---|---|---|
| 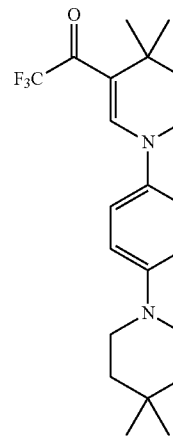 117 | 6.12 | 349 | 382 | 25890 | 657 | Enamine formation followed by acylation. By-product |
| 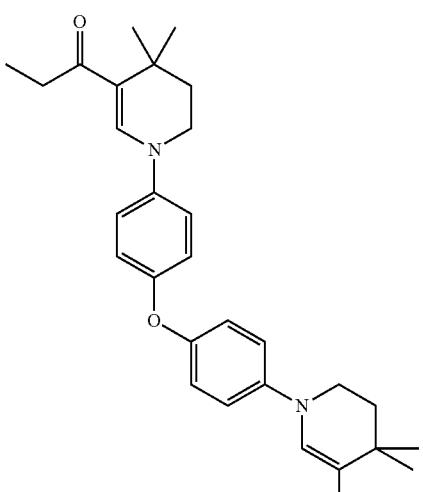 118 | 8.38 | 334 | 353 | 56063 | 1121 | Enamine formation followed by acylation |
| 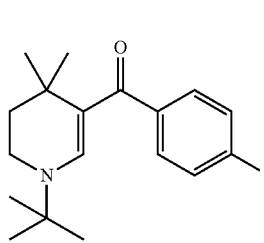 119 | 5.60 | 316 | 346 | 20919 | 655 | Enamine formation followed by acylation |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 120 | 9.22 | 331 | 354 | 71432 | 1207 | Enamine formation followed by acylation |
| 121 | 8.84 | 326 | 378 | 50670 | 859 | Enamine formation followed by acylation |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 122 | 8.72 | 303 391 | 390 | 32975 32139 | 593 578 | Enamine formation followed by acylation and then Heck reaction. |
| 123 | 9.16 | 328 | 349 | 63191 | 1234 | Enamine formation followed by acylation |
| 124 | 8.17 | 360 | 385 | 27646 | 564 | Enamine formation followed by acylation and then Heck reaction. Intermediate. |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 125 | 6.79 | 360 | 386 | 21473 | 532 | Enamine formation followed by acylation and then Heck reaction. |
| 126 | 8.57 | 385 | 390 | 32159 | 591 | Enamine formation followed by acylation and then Heck reaction. Intermediate. |
| 127 | 5.77 | 362 | 386 | 13489 | 411 | Enamine formation followed by acylation and then Heck reaction. |
| 128 | 7.54 | 383 | 389 | 30128 | 525 | Enamine formation followed by acylation and then Heck reaction. |

TABLE 1-continued
Compound data and synthetic approach for compounds.
| Structure and compound number | Clog P | λmax nm | λcrit nm | ε | E (1%, 1 cm) | General Synthetic Approach |
|---|---|---|---|---|---|---|
| 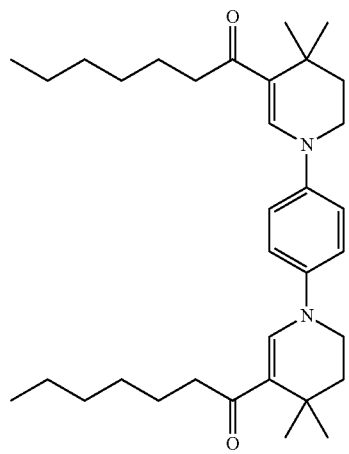 [SMILES: CCCCCCC(=O)C1=CN(c2ccc(N3C=C(C(=O)CCCCCC)C(C)(C)CC3)cc2)CCC1(C)C] 129 | 10.51 | 359<br>359 | 378<br>378 | 60809<br>70222 | 1169<br>1350 | Enamine formation followed by acylation |
| 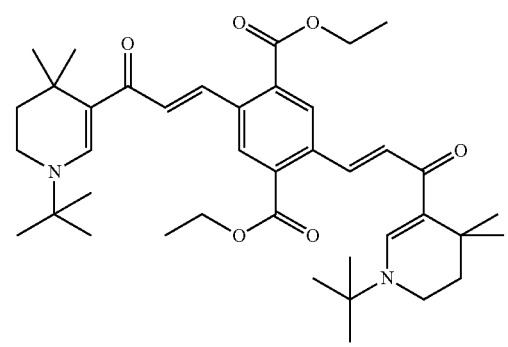 [SMILES: CCOC(=O)c1cc(/C=C/C(=O)C2=CN(C(C)(C)C)CCC2(C)C)c(C(=O)OCC)cc1/C=C/C(=O)C1=CN(C(C)(C)C)CCC1(C)C] 130 | 8.57 | 383 | 388 | 23457 | 355 | Enamine formation followed by acylation and then Heck reaction. |
| 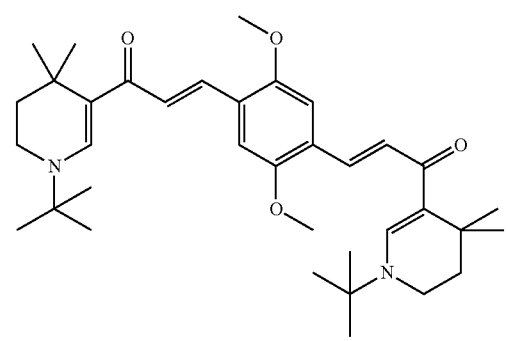 [SMILES: COc1cc(/C=C/C(=O)C2=CN(C(C)(C)C)CCC2(C)C)c(OC)cc1/C=C/C(=O)C1=CN(C(C)(C)C)CCC1(C)C] 131 | 7.58 | 402 | 391 | 32220 | 559 | Enamine formation followed by acylation and then Heck reaction. |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 132 | 7.63 | 391 | 388 | 24359 | 369 | Enamine formation followed by acylation and then Heck reaction. |
| 133 | 10.23 | 344<br>413 | 389 | 28080<br>25630 | 455<br>416 | Enamine formation followed by acylation and then Heck reaction. |
| 134 | 10.38 | 323 | 356 | 51851 | 830 | Enamine formation followed by acylation then Pd catalysed amination |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 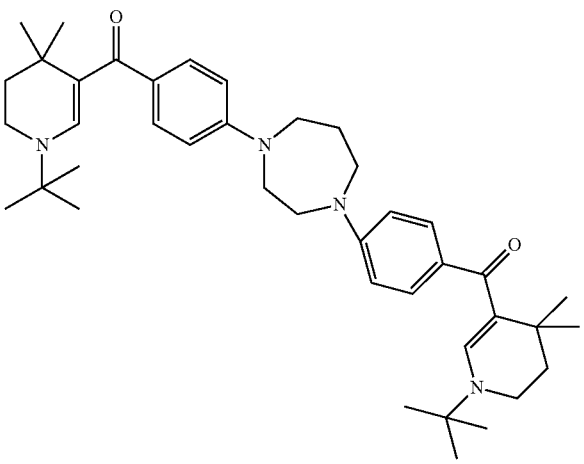 [SMILES: CC1(C)CCN(C(C)(C)C)C=C1C(=O)c1ccc(N2CCCN(c3ccc(C(=O)C4=CN(C(C)(C)C)CCC4(C)C)cc3)CC2)cc1] 135 | 10.45 | 318 342 | 365 | 37800 40535 | 592 635 | Enamine formation followed by acylation then Pd catalysed amination |
| 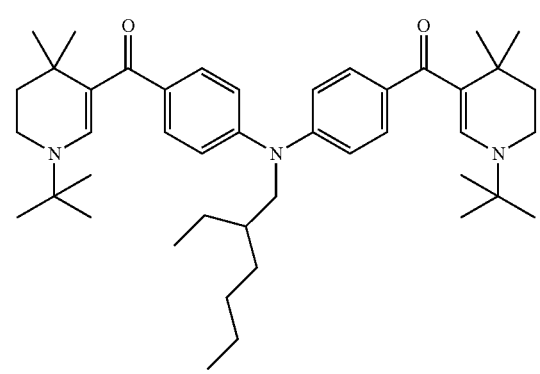 [SMILES: CCCCC(CC)CN(c1ccc(C(=O)C2=CN(C(C)(C)C)CCC2(C)C)cc1)c1ccc(C(=O)C2=CN(C(C)(C)C)CCC2(C)C)cc1] 136 | 13.93 | 316 Shoulder ca. 340 nm | 369 | 41598 | 624 | Enamine formation followed by acylation then Pd catalysed amination |
| 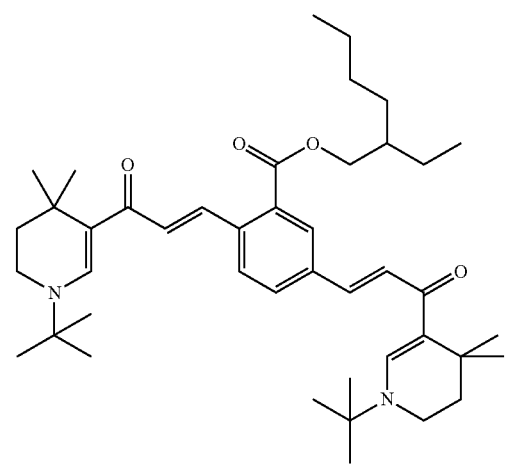 [SMILES: CCCCC(CC)COC(=O)c1cc(/C=C/C(=O)C2=CN(C(C)(C)C)CCC2(C)C)ccc1/C=C/C(=O)C1=CN(C(C)(C)C)CCC1(C)C] 137 | 11.12 | 378 | 388 | 30963 | 460 | Enamine formation followed by acylation and then Heck reaction. |

TABLE 1-continued
Compound data and synthetic approach for compounds.
| Structure and compound number | Clog P | λmax nm | λcrit nm | ε | E (1%, 1 cm) | General Synthetic Approach |
|---|---|---|---|---|---|---|
| 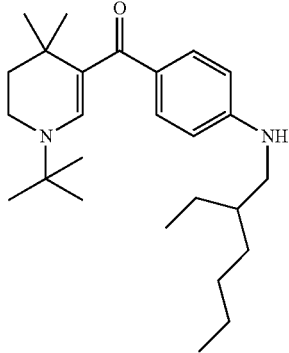 [SMILES: CCCCC(CC)CNc1ccc(C(=O)C2=CN(C(C)(C)C)CCC2(C)C)cc1] 138 | 8.70 | 318 | 362 | 21936 | 551 | Enamine formation followed by acylation then Pd catalysed amination. Intermediate. |
| 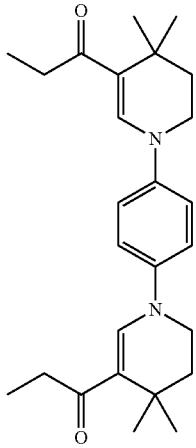 [SMILES: CCC(=O)C1=CN(c2ccc(N3C=C(C(=O)CC)C(C)(C)CC3)cc2)CCC1(C)C] 139 | 6.28 | 357 | 377 | 52638 | 1290 | Enamine formation followed by acylation |
| 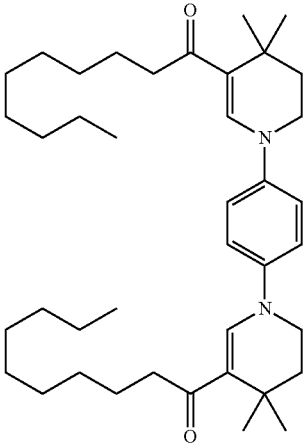 [SMILES: CCCCCCCCCC(=O)C1=CN(c2ccc(N3C=C(C(=O)CCCCCCCCC)C(C)(C)CC3)cc2)CCC1(C)C] 140 | 13.68 | 359 | 378 | 54278 | 898 | Enamine formation followed by acylation |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 141 | 22.15 | 359 | 379 | 37068 | 447 | Enamine formation followed by acylation |
| 145 | 4.9 | 309 | 327 | 28554 | 1137 | Enamine formation followed by acylation |
| 152 | 8.0 | 358 | 377 | 47560 | 820 | Enamine formation followed by acylation |

TABLE 1-continued
Compound data and synthetic approach for compounds.
| Structure and compound number | Clog P | λmax nm | λcrit nm | ε | E (1%, 1 cm) | General Synthetic Approach |
|---|---|---|---|---|---|---|
| 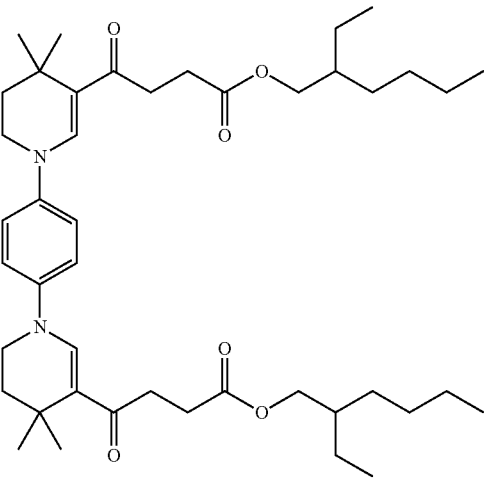 [SMILES: CCCCC(CC)COC(=O)CCC(=O)C1=CN(c2ccc(N3C=C(C(=O)CCC(=O)OCC(CC)CCCC)C(C)(C)CC3)cc2)CCC1(C)C] 153 | 13.0 | 359 | 379 | 45301 | 628 | Enamine formation followed by acylation |
| 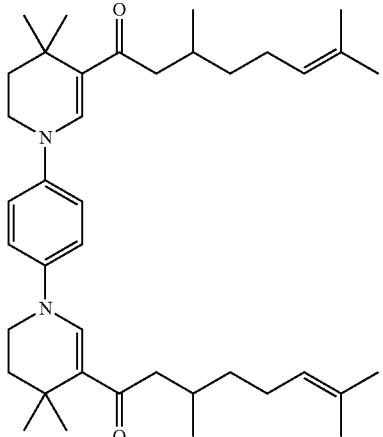 154 | 12.2 | 359 | 379 | 41400 | 690 | Enamine formation followed by acylation |
| 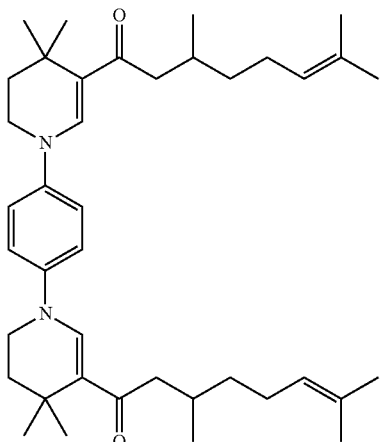 155 | 12.2 | 358 | 378 | 33000 | 550 | Enamine formation followed by acylation. Alternate isomer. |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 156 | 8.4 | 360 | 379 | 56032 | 1030 | Enamine formation followed by acylation |
| 157 | 6.8 | 358 | 379 | 59296 | 1090 | Enamine formation followed by acylation |
| 158 | 12.0 | 369 | 388 | 51600 | 750 | Enamine formation followed by acylation |

TABLE 1-continued

Compound data and synthetic approach for compounds.

| Structure and compound number | Clog P | λmax nm | λcrit nm | ε | E (1%, 1 cm) | General Synthetic Approach |
|---|---|---|---|---|---|---|
| 159 | 8.8 | 348 | 366 | 60200 | 875 | Enamine formation followed by acylation |
| 160 | 6.4 | 346 | 364 | 67344 | 1380 | Enamine formation followed by acylation |

Synthesis Approach and Data for Select Non-Fluorinated Compounds

The following indicates synthetic approaches for certain compounds of the first aspect. The header preceding the compound indicates the particular region of the electromagnetic spectrum in which the compound has been demonstrated to be a particularly effective absorber.

UV-A

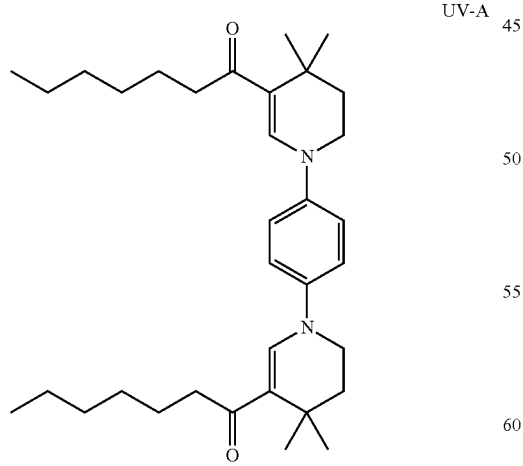

Analogues of the above compound explicitly considered are those with longer chain (such as 7 to 12 carbon atoms) alkyl and branched alkanoyl groups and alkoxy groups (such as $C_2$ to $C_{12}$) extending from the carbonyl carbons.

Synthesis

Preparation of 1,1'-(1,4-phenylene)bis(4,4-dimethyl-piperidine-2,6-dione)

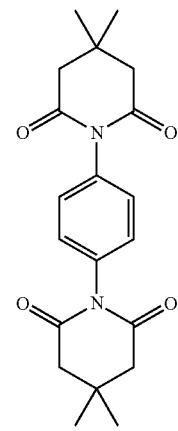 [SMILES: CC1(C)CC(=O)N(c2ccc(N3C(=O)CC(C)(C)CC3=O)cc2)C(=O)C1]

A solution of 3,3-dimethylglutaric anhydride, (5.0 g, 35.30 mmol) in $CHCl_3$ (30 mL) was treated with benzene-1,4-diamine (1.9 g, 17.57 mmol) and the mixture sonicated for 15 minutes before heating to reflux for 1.5 hours, after which time a thick suspension was obtained. This was cooled to room temperature and diluted with a further portion of $CHCl_3$ (15 mL). The mixture was then treated with thionyl chloride (3.85 mL, 52.70 mmol) and stirred for 15 minutes before heating to 100° C. for 10 minutes under microwave irradiation. The mixture was then evaporated in-vacuo and the residue washed with ether (75 mL) to afford the title compound as a white solid (5.85 g, 93%).

Preparation of 1,1'-(1,4-phenylene)bis(4,4-dimethyl-3,4-dihydropyridin-2(1H)-one)

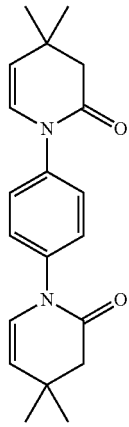 [SMILES: CC1(C)C=CN(c2ccc(N3C=CC(C)(C)CC3=O)cc2)C(=O)C1]

A suspension of 1,1'-(1,4-phenylene)bis(4,4-dimethyl-3,4-dihydropyridin-2(1H)-one), (2.5 g, 7.01 mmol) in THF (150 mL) was cooled on an ice bath and treated drop wise with lithium aluminium hydride (1 M solution in diethyl ether, 9.12 mL, 9.12 mmol) and the mixture stirred for 30 minutes. The reaction was then quenched by addition of 2 M hydrochloric acid solution until effervescence ceased followed by 4 M hydrochloric acid solution until a clear aqueous phase of pH <2 was formed. The biphasic mixture was then stirred for 15 minutes, diluted with diethyl ether (100 mL) and water (50 mL) and the organic phase separated and combined with further EtOAc (2×75 mL) and DCM (2×75 mL) extracts. The organic extracts were then dried with magnesium sulfate and evaporated in-vacuo to give the crude material as a brown gum which was dried under vacuo at 60° C. for 18 h. The residue was then stirred with EtOAc (50 mL) for 30 minutes, the precipitate discarded and the liquors evaporated in-vacuo to give the title compound as cream solid (1.19 g, 52%). $\delta_H$ (400 MHz) 7.31 (s, 4H), 6.17 (d, J7.7, 2H), 5.17 (d, J7.7, 4H), 2.56 (s, 4H), 1.17 (s, 12H).

Preparation of 1,4-bis(4,4-dimethyl-3,4-dihydropyridin-1(2H)-yl)benzene

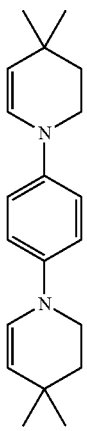 [SMILES: CC1(C)C=CN(c2ccc(N3C=CC(C)(C)CC3)cc2)CC1]

A suspension of 1,1'-(1,4-phenylene)bis(4,4-dimethyl-3,4-dihydropyridin-2(1H)-one) (1.1 g, 3.39 mmol) in diethyl ether (60 mL) was treated drop wise with lithium aluminium hydride (1 M solution in ether, 6.78 mL, 6.78 mmol). The resulting milky suspension was then refluxed for 2 hours, heating discontinued and the mixture allowed to cool in the oil bath for 10 minutes before being quenched by addition of sodium sulfate decahydrate (0.48 g, 14.92 mmol). Once addition was complete the mixture was stirred for 20 minutes and treated with anhydrous sodium sulfate (0.6 g), stirred for a further 10 minutes and filtered into a receiving flask was preloaded with BHT (10 mg). The filter pad was then washed with ether and the combined organics evaporated to a cream solid (0.76 g, 76%). $\delta_H$ (400 MHz) 6.85 (s, 4H), 6.38 (d, J 8.1, 2H), 4.47 (d, J8.1, 2H), 3.45 (t, J5.8, 4H), 1.72 (t, J5.8, 4H), 1.08 (s, 12H).

Preparation of 1,1'-(1,4-phenylenebis(4,4-dimethyl-1,4,5,6-tetrahydropyridine-1,3-diyl))bis(heptan-1-one)

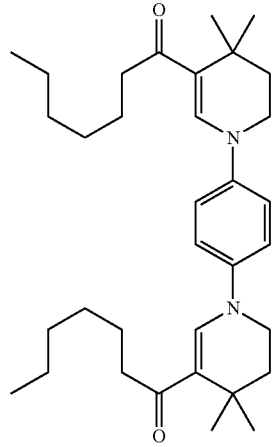 [SMILES: CCCCCCC(=O)C1=CN(c2ccc(N3C=C(C(=O)CCCCCC)C(C)(C)CC3)cc2)CCC1(C)C]

A solution of 1,4-bis(4,4-dimethyl-3,4-dihydropyridin-1(2H)-yl)benzene (200 mg, 0.68 mmol) and triethylamine (282 μL, 2.02 mmol) in DCM (20 mL) was cooled on an ice bath and treated drop wise with heptanoyl chloride (261 μL, 1.69 mmol). The mixture was then allowed to warm to RT O/N with stirring and treated with further portions of triethylamine (94 μL) and heptanoyl chloride (104 μL) before stirring for a further 15 minutes. After 1 h further portions of the reagents were added as above and this process repeated after a further 1 h. The mixture was then stirred for 1 h, diluted with water (30 mL) and DCM (20 mL) and the organic phase separated, washed with water (30 mL) and dried with magnesium sulfate. Evaporation in-vacuo gave the crude material as a brown oil which was purified by column chromatography over silica gel, eluting with 0-10% ethyl acetate: petroleum ether. Evaporation of the eluents gave the title compound as a pale yellow solid (99 mg, 27%), m.pt. 130-131° C. $\delta_H$ (400 MHz) 7.57 (s, 2H), 7.07 (s, 4H), 3.56 (t, J5.8, 4H), 2.50 (t, J7.7, 4H), 1.75 (t, J 5.8, 4H), 1.61 (t, J 7.8, 4H), 1.35-1.25 (m, 24H), 0.86 (t, J 8.0, 6H). $\delta_C$ (100 MHz) 197.7, 141.7, 121.4, 118.9, 43.7, 39.6, 37.6, 31.9, 30.7, 29.4, 28.1, 26.2, 22.7, 14.2. HRMS (ES): calc. for $C_{34}H_{52}N_2O_2F_6$ [M+], 488.1893. Found, 488.1902 [M+]. UV $\lambda_{max}$ 359 nm, ε 70222 M$^{-1}$ cm$^{-1}$.
Broad Spectrum:

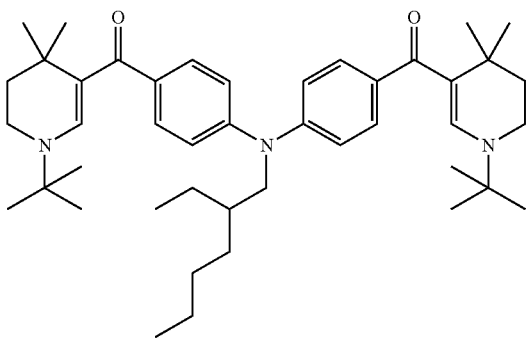 [SMILES: CCCCC(CC)CN(c1ccc(C(=O)C2=CN(C(C)(C)C)CCC2(C)C)cc1)c1ccc(C(=O)C2=CN(C(C)(C)C)CCC2(C)C)cc1]

Variations at the length and nature of the chain extending from the central nitrogen linking the phenyl rings may be straight chain or branched C-7 to C-12 alkyl, acyl and alkoxy. Variation at the group attached to the ring nitrogen is also explicitly considered, as set out for such ring position earlier.

Preparation of (((2-ethylhexyl)azanediyl)bis(4,1-phenylene))bis((1-(tert-butyl)-4,4-dimethyl-1,4,5,6-tetrahydropyridin-3-yl)methanone)

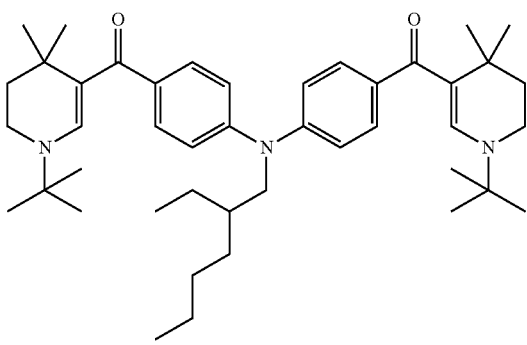 [SMILES: CCCCC(CC)CN(c1ccc(C(=O)C2=CN(C(C)(C)C)CCC2(C)C)cc1)c1ccc(C(=O)C2=CN(C(C)(C)C)CCC2(C)C)cc1]

A mixture of (4-bromophenyl)(1-(tert-butyl)-4,4-dimethyl-1,4,5,6-tetrahydropyridin-3-yl)methanone, (208 mg, 0.59 mmol), homopiperazine (27 mg, 0.27 mmol) and cesium carbonate (263 mg, 0.81 mmol) in THF (5 mL) was purged with nitrogen and treated with DavePhos (21 mg, 0.054 mmol) and bis(dibenzylideneacetone)palladium(0) (16 mg, 0.027 mmol). Once addition was complete the mixture was purged with nitrogen again, the vessel sealed and heated to 80° C. for 72 hours. The mixture was then cooled to room temperature, filtered through Celite and the filter cake washed with DCM. Evaporation of the filtrates in-vacuo gave the crude material as an orange gum which was purified by column chromatography over silica gel eluting with 0-30% ethyl acetate:petroleum ether. Evaporation of the eluents title compound as a pale yellow foam (117 mg, 65%). $\delta_H$ (CDCl$_3$, 400 MHz) 7.38 (d, J8.7, 4H), 7.24 (s, 2H), 6.92 (d, J8.8, 4H), 3.64 (d, J7.3, 2H), 3.20 (t, J5.8, 4H), 1.70-1.63 (m, 5H), 1.33 (s, 12H), 1.24-1.18 (m, 24H), 0.86-0.78 (m, 6H). $\delta_C$ (CDCl$_3$, 100 MHz) 193.1, 149.5, 147.9, 135.4, 130.4, 120.2, 115.7, 57.0, 56.3, 39.8, 38.8, 37.8, 30.9, 30.5160, 28.9, 28.2, 28.0, 24.2, 23.2, 14.2, 10.9. HRMS (ES): calc. for C$_{44}$H$_{65}$N$_3$O$_2$ [M$^+$], 667.5071. Found, 667.5075 [M+]. UV $\lambda_{max}$ 316 nm, $\varepsilon$ 41598 M$^{-1}$ cm$^{-1}$. UVA/Vis

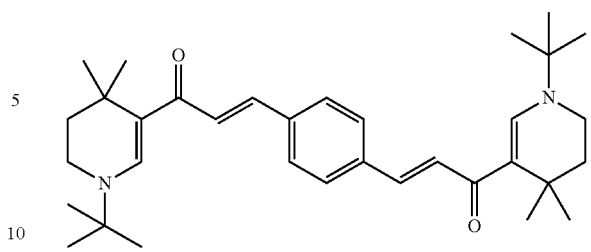

Variation may be considered on the central phenyl ring, including C1 to C6 alkyl, acyl and alkoxy groups, as well as the group attached to the ring nitrogen (as per R5 groups described earlier) to improve solubility. Preferred substituents may lack an α hydrogen to maintain increased stability and may comprise substituted aryl and substituted alkyl. One particular substituent explicitly considered to be disclosed with the above compound is tert-octyl as shown below:

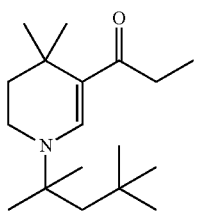 [SMILES: CCC(=O)C1=CN(C(C)(C)CC(C)(C)C)CCC1(C)C]

Synthesis

Preparation of (2E,2'E)-3,3'-(1,4-phenylene)bis(1-(1-(tert-butyl)-4,4-dimethyl-1,4,5,6-tetrahydropyridin-3-yl)prop-2-en-1-one)

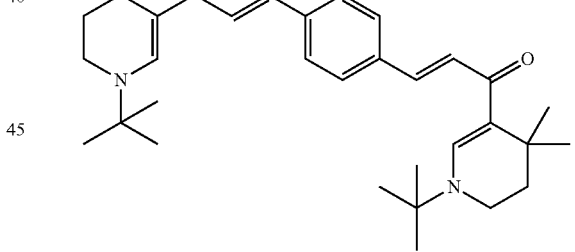

A mixture 1-(1-(tert-butyl)-4,4-dimethyl-1,4,5,6-tetrahydropyridin-3-yl)prop-2-en-1-one, (100 mg, 0.45 mmol) and 1,4-dibromobenzene (51 mg, 0.22 mmol) in acetonitrile (3 mL) was treated with triethylamine (150 μL, 1.08 mmol) and a mixture of palladium(II)acetate (10 mg, 0.043 mmol) and tris(o-tolyl)phosphine (26 mg, 0.086 mmol) in acetonitrile (1 mL) which had been previously sonicated for 1 minute. The mixture was then heated to reflux for 4 hours under an inert atmosphere. The reaction mixture was evaporated in-vacuo to give the crude material which was purified by column chromatography over silica gel eluting with 40% ethyl acetate:DCM, followed by radial chromatography eluting with 0-40% ethyl acetate:DCM. Evaporation of the eluent gave the title compound as a yellow solid (96 mg, 86%), m.pt. 265° C. (decomp). $\delta_H$ (CDCl$_3$, 400 MHz) 7.74 (s, 2H), 7.49 (s, 4H), 7.46 (d, J 15.5, 2H), 7.13 (d, J 15.5, 2H), 3.24 (m, 4H), 1.64 (m, 4H), 1.36 (s, 18H), 1.34 (s, 12H). $\delta_C$ (CDCl$_3$, 100 MHz) 185.6, 144.5, 137.7, 137.1, 128.0, 124.7, 118.0, 57.5, 40.1, 39.0, 30.8, 28.4, 28.0. HRMS (APCI): calc. for $C_{34}H_{48}N_2O_2$ [M$^+$], 516.3710. Found, 516.3712 [M$^+$]. UV $\lambda_{max}$ 386 nm, ε 36404 M$^{-1}$ cm$^{-1}$.

Photostability Protocol

The compounds of formula I or II demonstrate an improved stability upon exposure to electromagnetic radiation. The below approach was used to demonstrate this.

1 mL of a 3% solution of the test compound (30 mg of test compound in 1 mL solvent) was prepared in a solvent mix made up of 50% EtOH and 25% capric/caprylic triglyceride and 25% $C_{12}$-$C_{15}$ alkyl benzoate. 50 µL of this solution (containing 1.5 mg of test compound) was added carefully to the centre of a glass microscope slide and the volatile components left to evaporate in the dark for at least 3 hours to give a liquid film. The prepared films were then exposed for 1 hour to an Eimac 150 W xenon arc lamp filtered through Pyrex (15 Amp supply current, samples 19 cm from the lamp) previously allowed to warm up for 15 minutes prior to sample exposure. The irradiation was performed in a fume cupboard where the air flow was sufficient to keep sample T<30° C. One hour's exposure represented a calculated radiation dose (using meter) of approximately 100 MED.

In order to calculate the photostability of the test compounds, the exposed slides were placed in a beaker and rinsed with 2×5 mL EtOH, 1×5 mL MeOH. The combined washings were then added to a 100 mL volumetric flask and made up to 100 mL total volume with methanol. The UV absorbance was then measured in a 10 mm cuvette. The percent stability is measured as the ratio of absorbance at $\lambda_{max}$ for the irradiated sample compared to the unirradiated sample. As a further measure, a comparison of the sum of the absorbance in the 290-400 nm range was calculated.

The thin films are a good surrogate for testing the stability of a candidate in a sunscreen formulation as they use cosmetic emollients as solvent and are formed at cosmetically relevant concentrations.

A range of electromagnetic energy absorbing compounds were tested, some with fluorinated photostability tags, as per the compounds of formula I and II, and some without such electron withdrawing moieties to provide a suitable comparison of stabilising effects. The results are shown in table 3.

It can be seen from table 3 that t-Butyl compound 319, 2 was significantly more photostable than 1, with over 40% remaining. This is in line with observations on the stability of these compounds to autoxidation which have confirmed that 3° alkyl compounds show enhanced stability compared to 1° alkyl compounds such as the iso-butyl of 1. However, fluorinated t-Butyl compound 98 appeared significantly more photostable again with 88% remaining after exposure to the lamp for 1 h. The stability here also appears due to the presence of the trifluoroacetyl group. This is extremely electron withdrawing and the extra stabilisation observed is postulated, at least in part, to be due to this group pulling electron density from the ring nitrogen and decreasing reactivity in the ground state. Also significant may be the effect of the trifluoroacetyl group in stabilisation of the excited state (triplet) of the compound or in increasing the rate at which the excited state relaxes back to the ground state. Thus, in addition to or instead of the ring electron density withdrawing effect discussed above, it may be that the CF3 group stabilises one radical end of the triplet diradical of the excited state. It will be appreciated that the scope of the present invention is not limited by the mechanisms by which photostabilisation occurs or is achieved. This stabilisation is further seen with trifluoroacetyl compound 106 which is less than 5% decomposed.

The use of a N-phenyl substituent in compound 23 did not impart any substantial increase in photostability compared to parent compound 1 and this, with the rest of the results in table 3, strongly indicates that the fluorination in the $R_a$ and $R_b$ positions of formula II as well as fluorination within the $R_3$ group has a strong photostabilisation effect on the enamine ring thereby providing for improved operational lifetime of the compounds demonstrating this structure when exposed to electromagnetic radiation. The photostability results can be seen in Table 3 and the results for select compounds are also represented in graphical form in the figures.

Figure 2:
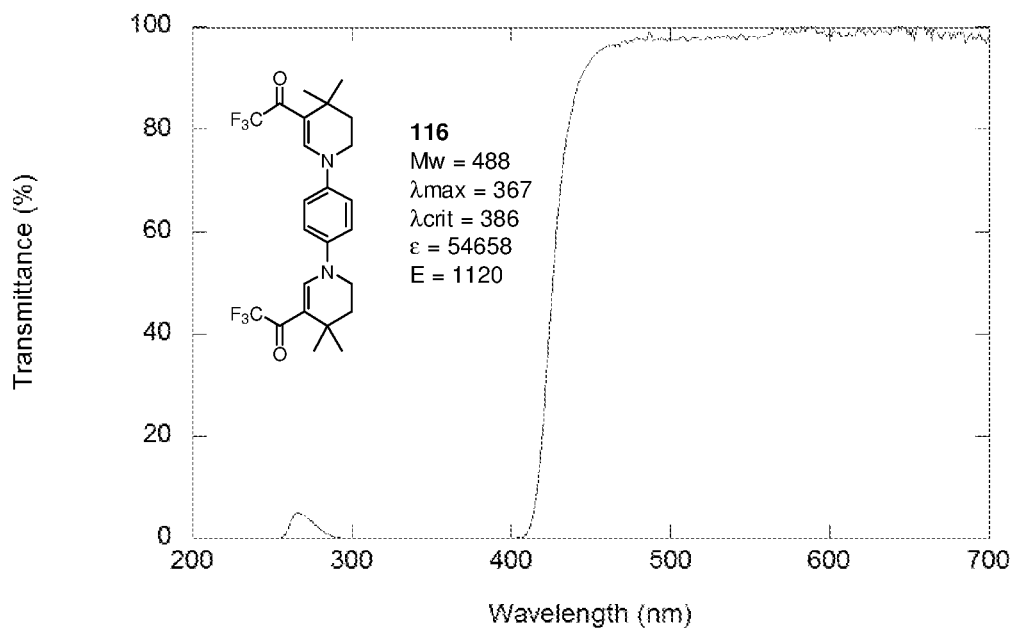
FIG. 2 is a is a graphical representation of the % transmission of compound 116.

FIG. 1 and FIG. 2 show the useful level and range of absorbance (FIG. 1) and transmission (FIG. 2) for compound 116 which, as seen from the structure provided on both graphs, has three fluorine atoms directly bonded to the carbonyl carbon attached to the ring. Data for this and compound 158 is also presented in table 2, below.

TABLE 2

Data for compounds 116 and 158.

| Structure | Mw | ClogP | $\lambda_{max}$ (nm) | $\lambda_{crit}$ (nm) | ε | E (1%, 1 cm) |
|---|---|---|---|---|---|---|
| 116 | 488 | 6.3 | 367 | 387 | 54658 | 1120 |
| 158 | 688 | 12.0 | 369 | 388 | 51600 | 750 |

Figure 3:
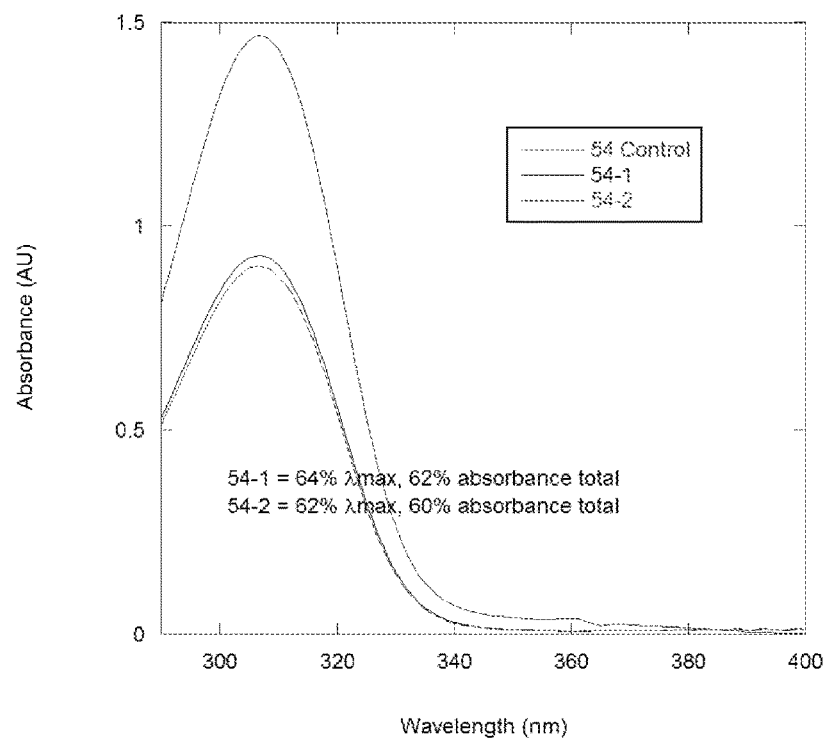
FIG. 3 is a graphical representation of the loss in absorbance of compound 54 upon exposure to irradiation with a xenon arc lamp (54 Control is uppermost line at peak point of approximately 310 nm, 54-1 is second uppermost line at peak point and 54-2 is lowermost line at peak point)
Figure 4:
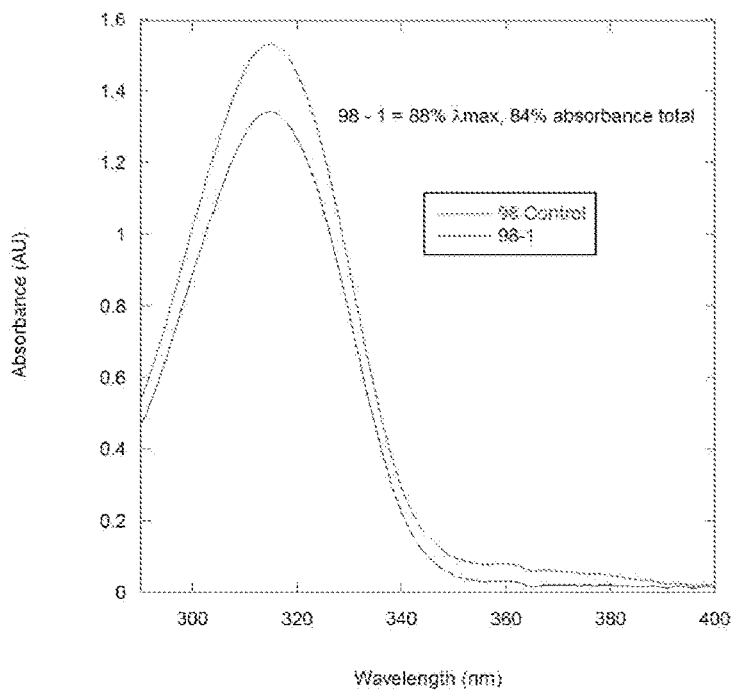
FIG. 4 is a graphical representation of the loss in absorbance of compound 98 upon exposure to irradiation with a xenon arc lamp (98 Control is uppermost line at peak point of approximately 320 nm and 98-1 is lowermost line at peak point)
Figure 5:
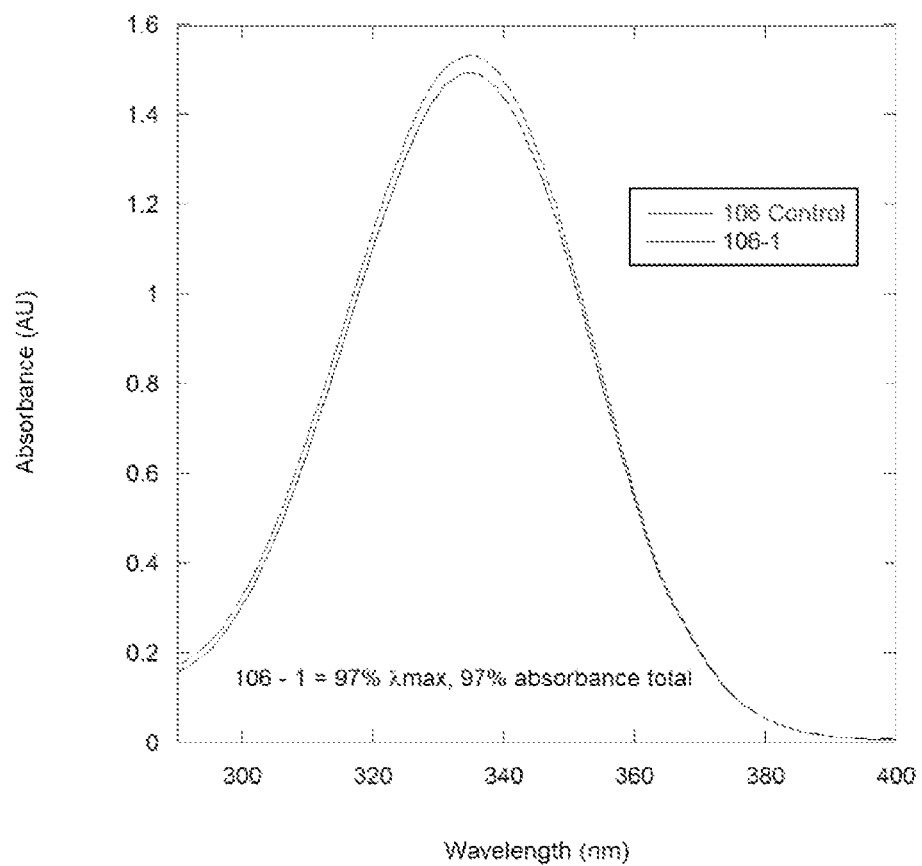
FIG. 5 is a graphical representation of the loss in absorbance of compound 106 upon exposure to irradiation with a xenon arc lamp (106 Control is uppermost line at peak point of approximately 335 nm and 106-1 is lowermost line at peak point).

FIGS. 3 to 5 are graphical representations of the loss in absorbance of compounds 54, 98 and 106, respectively, upon exposure to irradiation with a xenon arc lamp for one hour. Compound 54 is included as a non-fluorinated comparator compound, and one which demonstrates reasonable levels of stability. However, the advantages demonstrated by fluorinated compounds 98 and 106 can be clearly seen from the graph in terms of the minimal losses observed subsequent to irradiation. This reinforces the advantages provided by the compounds of formula I and II in terms of operational lifetime and improved protective capacity. In FIG. 3 the two lower lines are the results of two identical experiments.

TABLE 3

Summary of photostability results. Values denote % of original

| Structure | Number | % $\lambda_{max}$ | % abs total |
|---|---|---|---|
| 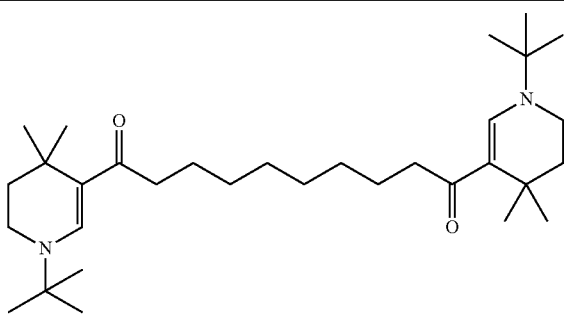 | 54 | 63 | 61 |
| 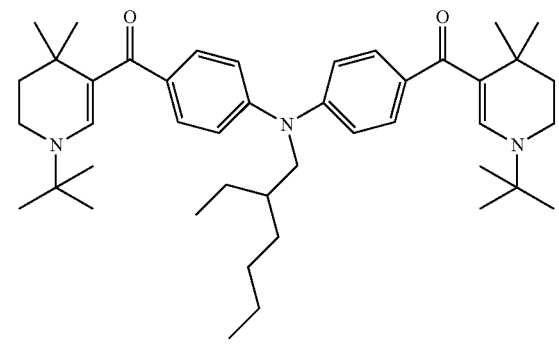 [SMILES: CCCCC(CC)CN(c1ccc(C(=O)C2=CN(C(C)(C)C)CCC2(C)C)cc1)c1ccc(C(=O)C2=CN(C(C)(C)C)CCC2(C)C)cc1] | 136 | 49 | 56 |
| 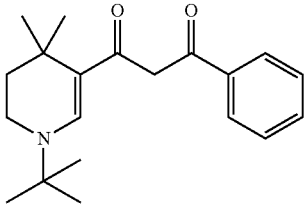 [SMILES: CC1(C)CCN(C(C)(C)C)C=C1C(=O)CC(=O)c1ccccc1] | 94 | 11 | 21 |
| 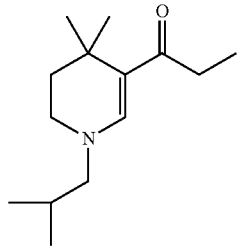 [SMILES: CCC(=O)C1=CN(CC(C)C)CCC1(C)C] | 1 | 21 | 24 |
| 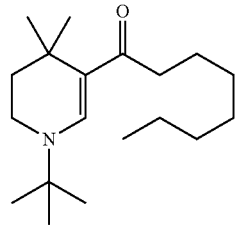 [SMILES: CCCCCCCC(=O)C1=CN(C(C)(C)C)CCC1(C)C] | 319, 2 | 45 | 47 |

TABLE 3-continued

Summary of photostability results. Values denote % of original

| Structure | Number | % λ$_{max}$ | % abs total |
|---|---|---|---|
| 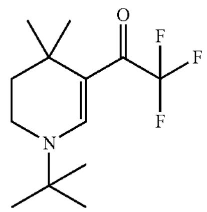 [SMILES: CC1(C)CCN(C(C)(C)C)C=C1C(=O)C(F)(F)F] | 98 | 88 | 84 |
| 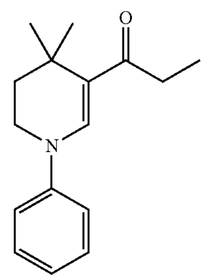 [SMILES: CCC(=O)C1=CN(c2ccccc2)CCC1(C)C] | 23 | 30 | 31 |
| 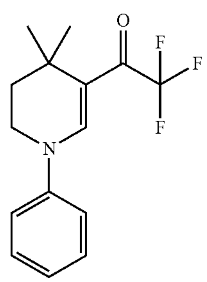 [SMILES: CC1(C)CCN(c2ccccc2)C=C1C(=O)C(F)(F)F] | 106 | 97 | 97 |
| 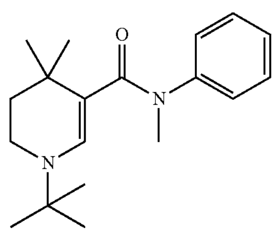 [SMILES: CN(C(=O)C1=CN(C(C)(C)C)CCC1(C)C)c1ccccc1] | 70 | 9 | 14 |
| 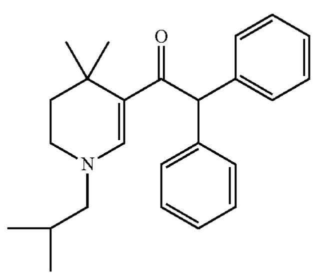 [SMILES: CC(C)CN1C=C(C(=O)C(c2ccccc2)c2ccccc2)C(C)(C)CC1] | 16 | 35 | 37 |
| 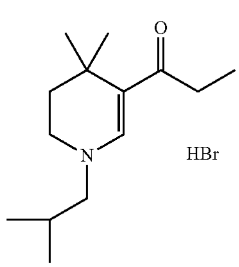 [SMILES: CCC(=O)C1=CN(CC(C)C)CCC1(C)C ; Br] | 44 | 56 | 56 |

TABLE 3-continued

Summary of photostability results. Values denote % of original

| Structure | Number | % λ$_{max}$ | % abs total |
|---|---|---|---|
| 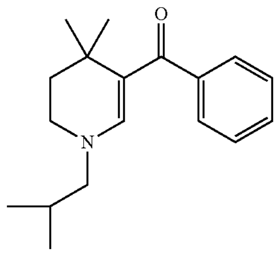 [SMILES: CC(C)CN1C=C(C(=O)c2ccccc2)C(C)(C)CC1] | 11 | 59 | 63 |
| 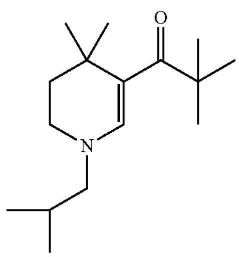 [SMILES: CC(C)CN1C=C(C(=O)C(C)(C)C)C(C)(C)CC1] | 145 | 60 | 60 |
| 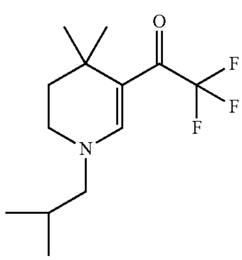 [SMILES: CC(C)CN1C=C(C(=O)C(F)(F)F)C(C)(C)CC1] | 146 | 89 | 88 |
| 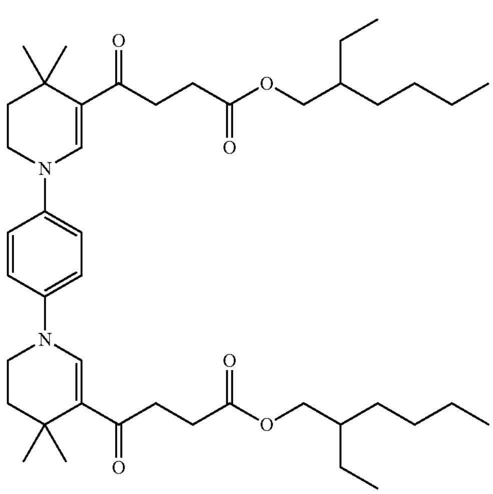 [SMILES: CCCCC(CC)COC(=O)CCC(=O)C1=CN(c2ccc(N3C=C(C(=O)CCC(=O)OCC(CC)CCCC)C(C)(C)CC3)cc2)CCC1(C)C] | 153 | 52 | |

TABLE 3-continued
Summary of photostability results. Values denote % of original
| Structure | Number | % λ$_{max}$ | % abs total |
|---|---|---|---|
| 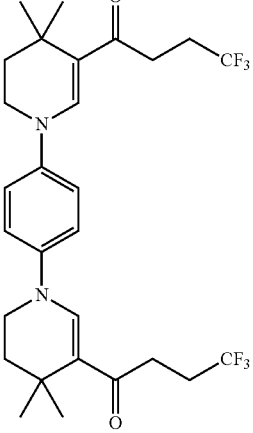 | 157 | 54 | |
| 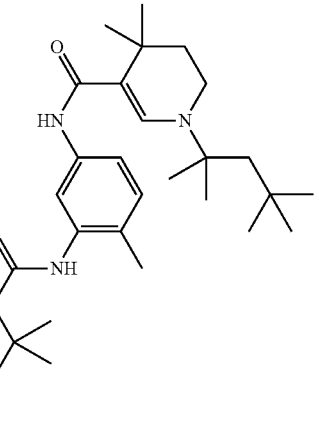 | 161 | 55 | |
absorbance remaining.
Further data is presented in table 4, below, for compounds 159 and 160.
TABLE 4
Summary of photostability results for compounds 159 and 160.
| Structure & number | Mw | ClogP | ε | E (1%, 1 cm) | Photostability (% remains) |
|---|---|---|---|---|---|
| 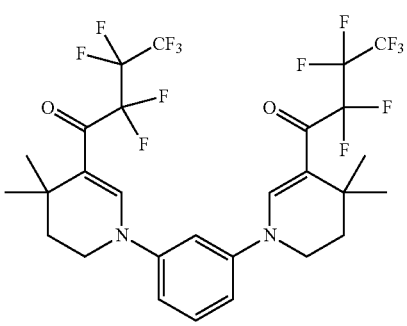<br>159 | 688 | 8.8 | 60200 | 875 | 91 |

TABLE 4-continued
Summary of photostability results for compounds 159 and 160.
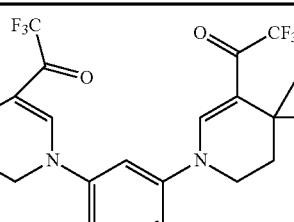
| Structure & number | Mw | ClogP | ε | E (1%, 1 cm) | Photostability (% remains) |
|---|---|---|---|---|---|
| 160 | 488 | 6.4 | 67344 | 1380 | 99 (after 1.5 h, others = 1 h) |
The increase in photostability which is provided by fluorination on going from alkyl to trifluoro can be seen in the representative examples below:
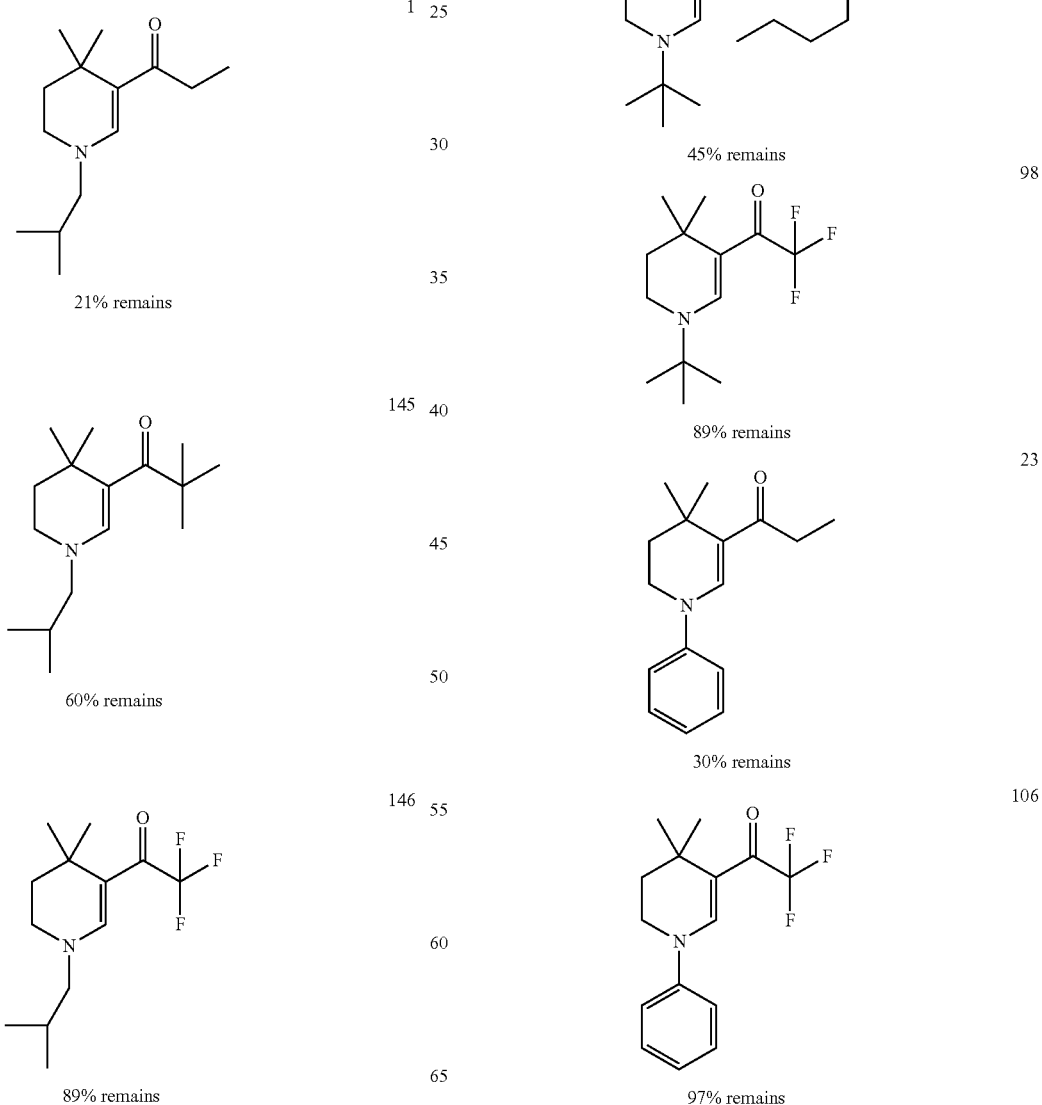

A number of conclusions can be drawn from the results. The use of 3° alkyl nitrogen substituents compared to 1° alkyl appears to confer an approximately 25% increase in photostability to the compounds under these conditions. The use of aryl nitrogen substituents causes a marginal improvement to stability (<10%) compared to 1° alkyl. The overwhelming observation is that the introduction of the trifluoroacetyl group gives the largest increase in stability (≥50%). This may be caused by one or more of a variety of mechanisms, as discussed above. The extent of the effect is surprising and the absence of protons α to the carbonyl group may also contribute.

Interestingly, the benzoyl group also imparts some added photostability (similar to the COtBu group) to the molecule but not to the same degree. It is postulated that the effect here is predominantly due to the lack of protons α to the carbonyl group. Further, the use of a salt of compound 1 (compound 44 in the table) gave some degree of stabilisation with over twice the amount of compound remaining compared to the free base (56% vs. 21%). This could potentially provide more photostable versions of the lead compound of the first aspect. Such salt forms may therefore be useful to enhance photostability in addition to the effect of the halogen tag described herein as well as to stabilise the ground state of compounds of formula V.

Salt forms, such as those described above, can be prepared by reaction of the compound of the first aspect with an organic or inorganic acid, using standard methods detailed in the literature.

Examples of acceptable salt forms of the compounds useful according to the invention include acid addition salts. Suitable acid addition salts according to the present invention include organic and inorganic acids and may include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular examples of salt forms include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenyl propionates, phenyl butyrates, citrates, lactates, γ-hydroxybutyrates, glycolates, tartrates, methanesulfonates, propanesulfonates, naphthalene-sulfonates, and mandelates.

Further, exposure of compound 94, a potential visible light absorbing candidate for use in lenses, sunscreen formulations etc. resulted in less than 20% of the material remaining. However, the bright yellow film initially seen by film formation with compound 94 became perfectly colourless during the course of the irradiation, an observation which could potentially be exploited in monitoring UV exposure for a range of applications including chemicals and food packaging where an indication of exposure is important for prediction of likely quality of the packaged material.

Further representative compounds of the invention and their associated absorption and photostability data (when available) are presented in table 5.

TABLE 5

| Absorption, physical characteristics and photostability results for select compounds. | | | | | |
|---|---|---|---|---|---|
| Photostability (%) | Structure and compound number | ClogP | λmax nm | λcrit nm | ε | E (1%, 1 cm) |
| | 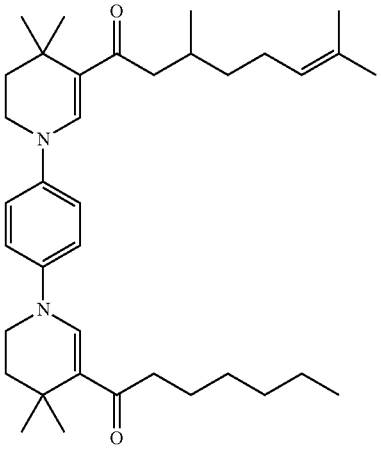 | 11.4 | 358 | 378 | 52353 | 934 |

167

TABLE 5-continued

Absorption, physical characteristics and photostability results for select compounds.

| Photo-stability (%) | Structure and compound number | ClogP | λmax nm | λcrit nm | ε | E (1%, 1 cm) |
|---|---|---|---|---|---|---|
| | 168 | 10.0 | 317 | 337 | 63346 | 1177 |
| 5 | 169 | 5.3 | 334 | 361 | 16618 | 497 |
| 13 | 170 | 5.7 | 330 | 361 | 14203 | 321 |
| <5 | 173 | 11.6 | 386 | 390 | 31937 | 486 |
| | 174 | 8.0 | 360 | 386 | 18987 | 437 |

TABLE 5-continued

Absorption, physical characteristics and photostability results for select compounds.

| Photo-stability (%) | Structure and compound number | ClogP | λmax nm | λcrit nm | ε | E (1%, 1 cm) |
|---|---|---|---|---|---|---|
| | 176 | 6.8 | 347 | 369 | 58853 | 1170 |
| 39 | 178 | 13.9 | 316 | 370 | 45910 | 653 |
| 76 | 179 | 5.4 | 315 | 342 | 25447 | 939 |
| | 180 | 6.8 | 326 | 346 | 75074 | 1495 |

TABLE 5-continued

*Absorption, physical characteristics and photostability results for select compounds.*

| Photo-stability (%) | Structure and compound number | ClogP | λmax nm | λcrit nm | ε | E (1%, 1 cm) |
|---|---|---|---|---|---|---|
|  | 181 | 6.8 | 339 | 358 | 66020 | 1315 |
| 100 | 182 | 6.4 | 340 | 364 | 56720 | 1094 |
| 85 | 184 | 4.9 | 312 | 331 | 35700 | 1162 |
| 100 | 185 | 5.2 | 314 | 333 | 34340 | 951 |

TABLE 5-continued

Absorption, physical characteristics and photostability results for select compounds.

| Photo-stability (%) | Structure and compound number | ClogP | λmax nm | λcrit nm | ε | E (1%, 1 cm) |
|---|---|---|---|---|---|---|
| 43 | 187 | 3.7 | 313 | 331 | 30868 | 1371 |
| 49 | 188 | 4.2 | 314 | 331 | 33288 | 1285 |
| 30 | 207 | 3.1 | 310 | 326 | 37586 | 1655 |
| 76 | 208 | 6.4 | 315 | 349 | 26531 | 782 |
| 50 | 262 | 3.6 | 311 | 344 | 26668 | 998 |

TABLE 5-continued

Absorption, physical characteristics and photostability results for select compounds.

| Photo-stability (%) | Structure and compound number | ClogP | λmax nm | λcrit nm | ε | E (1%, 1 cm) |
|---|---|---|---|---|---|---|
| 68 | 263 | 4.2 | 332 | 362 | 34743 | 1210 |
| 22 | 291 | 4.7 | 317 | 360 | 17272 | 635 |
| 33 | 297 | 6.6 | 311 | 326 | 33953 | 1084 |

In terms of the general synthetic approach taken to achieve the compounds in table 5, all compounds were synthetically accessed through enamine formation followed by acylation, as described in further detail above.

Table 6 provides a convenient comparison of compounds 54, 168, 98 and 169-170. Compound 168 was designed as a photostable analogue of previously identified lead compound 54. It absorbs efficiently with a higher molar extinction coefficient than the parent compound but was not sufficiently soluble for determination of photostability by the methods employed. This may not preclude use in lenses or other applications where solubility is not at issue. Compounds 169 and 170 are chloro and bromo analogues of trifluoroacetyl derivative 98. These were synthesised to probe if the photostabilising effect of the trifluoroacetyl group was also observed with other halogens. These compounds both possessed an approximately 15-20 nm increase in $\lambda_{max}$ relative to the parent absorber 98 with a concomitant drop in molar extinction coefficient. As can be seen from the data presented in Table 7, both compounds were effectively destroyed under irradiation. It can be seen then, that of the halogens, fluorine provides for unexpected benefits relative to chlorine and bromine.

TABLE 6

Comparison of compounds 54, 168, 98 and 169-170. All soluble compounds formed a colourless solution at 0.1% MeOH apart from 170 which formed a pale yellow solution.

| No. | Structure | ClogP | $\lambda_{max}$ (nm) | $\lambda_{crit}$ (nm) | ε | E (1%, 1 cm) | Appearance | Photostability (%) |
|---|---|---|---|---|---|---|---|---|
| 54 | (structure) | 9.01 | 307 | 322 | 59850 | 1197 | Cream solid | 63 |
| 168 | (structure) | 10.0 | 317 | 337 | 63346 | 1177 | Cream solid | Not soluble |
| 98 | (structure) | 3.97 | 315 | 331 | 36298 | 1380 | Yellow solid | 89 |
| 169 | (structure) | 5.3 | 334 | 361 | 16618 | 497 | Cream solid | 5 |
| 170 | (structure) | 5.7 | 330 | 361 | 14203 | 321 | Fawn solid | 13 |

The effect of substitution on the photostability of benzoyl derivatives was also investigated. This study made use of a number of previously synthesised t-butyl compounds whilst also requiring the synthesis of probe compounds 179, 184 and 185.

As can be seen, with the exception of the strongly electron donating dimethylamine group of 86 substitution has little effect on the position of absorbance but does significantly impact photostability with electron donating groups lowering photostability and a slight increase seen with the electron withdrawing bromine substituent (Table 7).

Replacement of the phenyl ring with a 4-pyridyl had little effect on photostability. The t-butyl benzoyl compound 179 was more stable than the isobutyl analogue (11) with 76% remaining after irradiation compared to 59%. A single fluorine atom did not appear to have a large effect on stability but the presence of 2 or more fluorine atoms progressively increases stability (184 and 185). These results allow for the tuning of the photostability of benzoyl substituted compounds without impacting on the position of absorbance maxima which provides for significant advantages in applying compounds of the invention to different applications. The negative impact of electron donation on photostability can also be seen with higher molecular weight amino functionalised analogues 109 and 136 (Table 1). 109, which could be considered as possessing more highly electron donating nitrogen atoms due to the long alkyl chain, had a photostability of 22% compared to parent dimethylamine compound 86 which was 30% photostable. Conversely aniline functionalised compound 136, which could be considered as possessing a less electron donating nitrogen moiety, had a photostability of 49%.

TABLE 7

Photostability of benzoyl derivatives.

| Structure | No. | $\lambda_{max}$ (nm) | Photo-stability (%) | Comments |
|---|---|---|---|---|
| 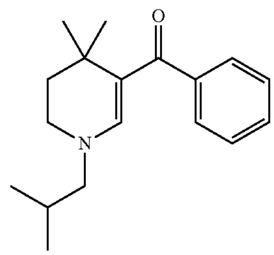 [SMILES: CC(C)CN1C=C(C(=O)c2ccccc2)C(C)(C)CC1] | 11 | 316 | 59 | |
| 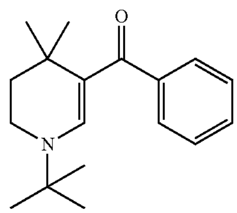 [SMILES: CC1(C)CCN(C(C)(C)C)C=C1C(=O)c1ccccc1] | 179 | 315 | 76 | N-isobutyl = 59% left |
| 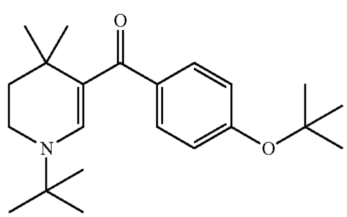 [SMILES: CC(C)(C)Oc1ccc(C(=O)C2=CN(C(C)(C)C)CCC2(C)C)cc1] | 88 | 317 | 38 | Electron donating |
| 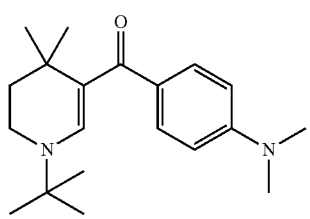 [SMILES: CN(C)c1ccc(C(=O)C2=CN(C(C)(C)C)CCC2(C)C)cc1] | 86 | 333 | 30 | Strongly electron donating |
| 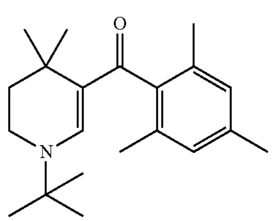 [SMILES: Cc1cc(C)c(C(=O)C2=CN(C(C)(C)C)CCC2(C)C)c(C)c1] | 297 | 311 | 33 | Electron donating |
| 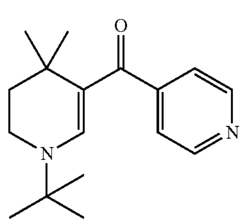 [SMILES: CC1(C)CCN(C(C)(C)C)C=C1C(=O)c1ccncc1] | 58 | 316 | 78 | |

TABLE 7-continued

Photostability of benzoyl derivatives.

| Structure | No. | $\lambda_{max}$ (nm) | Photo-stability (%) | Comments |
|---|---|---|---|---|
| 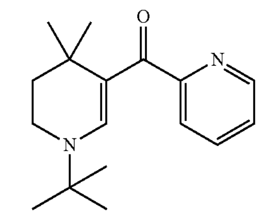 [SMILES: CC1(C)CCN(C(C)(C)C)C=C1C(=O)c1ccccn1] | 291 | 317 | 22 | |
| 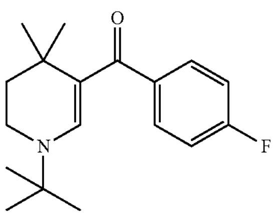 [SMILES: CC1(C)CCN(C(C)(C)C)C=C1C(=O)c1ccc(F)cc1] | 119 | 316 | 75 | Electron withdrawing |
| 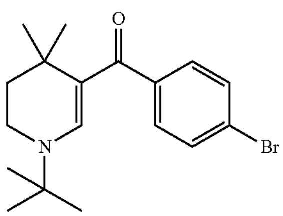 [SMILES: CC1(C)CCN(C(C)(C)C)C=C1C(=O)c1ccc(Br)cc1] | 76 | 317 | 85 | Electron withdrawing |
| 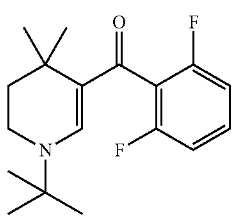 [SMILES: CC1(C)CCN(C(C)(C)C)C=C1C(=O)c1c(F)cccc1F] | 184 | 312 | 90 | Electron withdrawing |
| 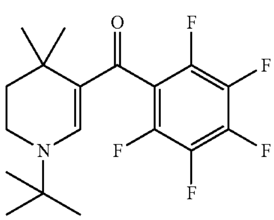 [SMILES: CC1(C)CCN(C(C)(C)C)C=C1C(=O)c1c(F)c(F)c(F)c(F)c1F] | 185 | 315 | 100 | Electron withdrawing |
| 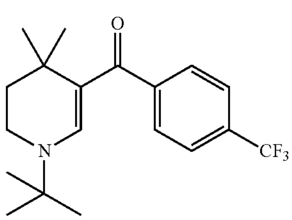 [SMILES: CC1(C)CCN(C(C)(C)C)C=C1C(=O)c1ccc(C(F)(F)F)cc1] | 208 | 315 | 76 | Electron withdrawing |

In general terms, the largest increase in photostability seen in the current tests was therefore with the introduction of the trifluoroacetyl group. This represents an advantageous result as the introduction of the trifluoroacetyl, and like substituents, is readily performed (yields are typically higher than with simple acid chlorides) and tends to give physically stable products. The increase in stability (both photo and physical) may allow the incorporation of 1° nitrogen substituents at the $R_5$ position thereby providing for a large gain in ease of synthesis and the potential to introduce solubilising groups to more readily address physical considerations. The use of trifluoroacetyl, or higher perfluoroalkyl acids, would also tend to increase solubility in oil based matrices. Benzoyl groups have also been seen to provide for certain advantages in use.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Unless defined otherwise, all technical and scientific terms used herein have the same meaning as would be commonly understood by those of ordinary skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. It is expected that skilled artisans will employ such variations as appropriate and it is considered within the scope and spirit of the present invention for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula II, or a salt thereof:

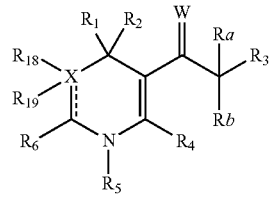

formula II wherein, the dotted line may be a bond;
X is one or two carbon atoms forming part of the ring structure;
$R_1$ and $R_2$ are independently selected from hydrogen, substituted $C_1$ to $C_6$ alkyl, or unsubstituted $C_1$ to $C_6$ alkyl;
W is O;
$R_a$, $R_b$, and $R_3$, when present, are independently selected from hydrogen, halo, $C_1$ to $C_{20}$ alkyl, $C_2$ to $C_{20}$ alkenyl, $C_2$ to $C_{20}$ alkynyl, aryl, heteroaryl, aroyl, $C_2$ to $C_{12}$ alkanone, $C_5$ to $C_7$ cycloalkyl, $C_4$ to $C_7$ cycloalkanone, $C_5$ to $C_7$ cycloalkenyl, $C_2$ to $C_{12}$ alkanoyl, $C_2$ to $C_{12}$ alkacanoyloxy, $C_2$ to $C_{12}$ alkoxycarbonyl, $C_2$ to $C_{12}$ carbamoyl, $C_2$ to $C_{12}$ carboxyl, haloalkyl, N-alkyl, N-aryl, N-heterocyclyl or heterocyclic, all of which groups may be substituted or unsubstituted, or $R_b$ and $R_3$ may together form an alkene, an alkyne, a phenyl ring or a heteroaryl ring each of which is optionally substituted with at least one halogen or halogen-containing group, and wherein at least one of $R_a$, $R_b$ and $R_3$ comprises a halogen;
$R_4$ is hydrogen;
$R_5$ is selected from $C_1$ to $C_{12}$ alkyl, $C_2$ to $C_{12}$ alkenyl, $C_2$ to $C_{12}$ alkynyl, aryl, amine, heteroaryl, heterocyclyl, $C_5$ to $C_7$ cycloalkyl, $C_5$ to $C_7$ cycloalkenyl, $C_2$ to $C_9$ alkanoyl, $C_1$ to $C_{12}$ alkanoyloxy or carbamoyl all of which groups may be substituted or unsubstituted;
$R_6$ is hydrogen; and
$R_{18}$ and $R_{19}$ are hydrogen,
with the proviso that when $R_1$ and $R_2$ are methyl, $R_a$, $R_b$, and $R_3$ are all fluorine, W is O and $R_4$ is hydrogen then $R_5$ is not any of 4-dimethylaminophenyl, 4-methoxyphenyl, 4-methylphenyl, 4-tert-butylphenyl, isopropyl or 1-naphthyl.

2. The compound of claim 1 wherein at least one of $R_a$ and $R_b$ are fluorine or wherein $R_b$ and $R_3$ combine to form a 6-membered ring with one or more fluorine substituents on the ring.

3. The compound of claim 1 wherein $R_3$ is selected from halo, $C_1$ to $C_9$ alkyl, $C_2$ to $C_9$ alkenyl, $C_5$-$C_6$aryl, $C_5$-$C_6$ heteroaryl, $C_2$ to $C_{12}$ alkanone, $C_5$-$C_6$ cycloalkyl, $C_5$-$C_6$ cycloalkanone, $C_5$-$C_6$ cycloalkenyl, $C_2$ to $C_9$ alkanoyl, $C_2$ to $C_9$ alkanoyloxy, $C_2$ to $C_9$ alkoxycarbonyl, $C_2$ to $C_9$ carbamoyl, $C_2$ to $C_9$ carboxyl, haloalkyl, N-alkyl, N-aryl, N-heterocyclyl or $C_5$-$C_6$ heterocyclic, all of which groups may be substituted or unsubstituted.

4. The compound of claim 1 wherein $R_3$ is $C_1$ to $C_6$ perfluoroalkyl.

5. The compound of claim 1 wherein $R_a$, $R_b$ and $R_3$ and the carbon to which they are attached, together form a moiety selected from the group consisting of:

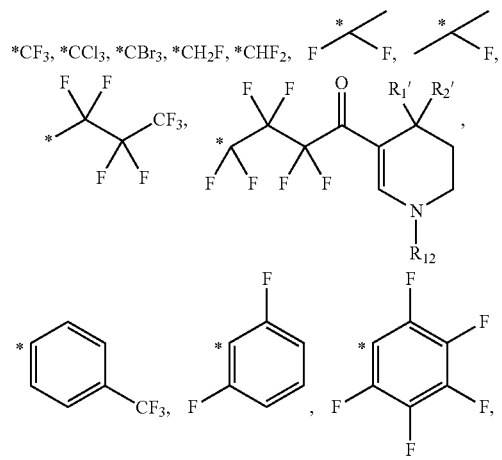

-continued

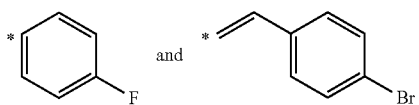

wherein, $R_1'$ and $R_2'$, may be selected from any group as defined for $R_1$ and $R_2$, respectively, and $R_{12}$ may be selected from hydrogen, $C_1$-$C_6$ alkyl or $C_1$-$C_6$ alkoxy.

6. The compound of claim 1 wherein $R_5$ is selected from $C_1$ to $C_6$ alkyl, $C_2$ to $C_6$ alkenyl, phenyl, aryl, naphthyl, $C_6$ cycloalkyl, $C_2$ to $C_6$ alkanoyl or $C_2$ to $C_6$ alkanoyloxy all of which groups may be substituted or unsubstituted.

7. The compound of claim 1 wherein $R_5$ is selected from the group consisting of:

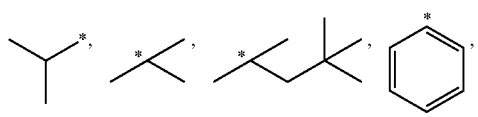

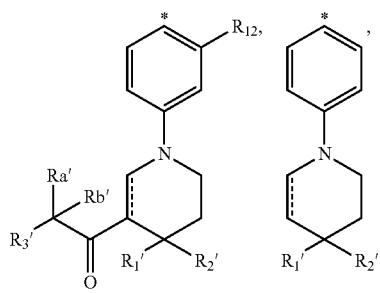

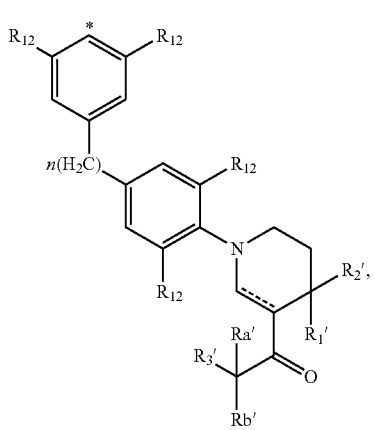

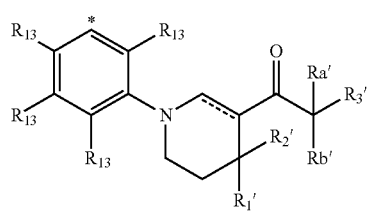

-continued

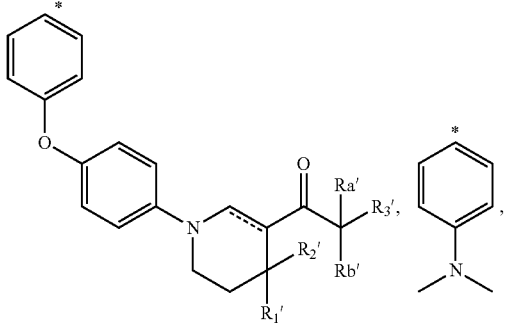

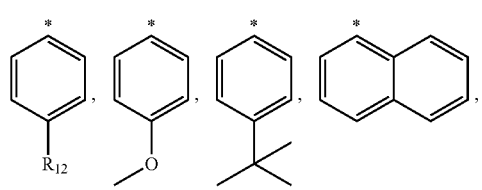

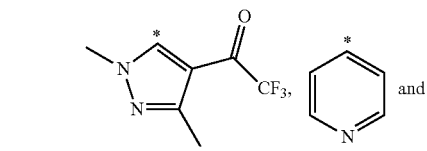

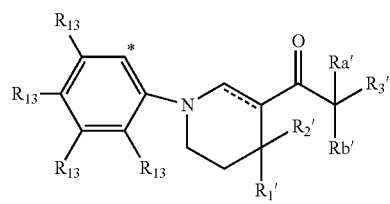

wherein, a dotted line may be a bond, n is from 0 to 5, $R_1'$, $R_2'$, $R_a'$, $R_b'$ and $R_3'$ may be selected from any group as defined in any one of the preceding claims for $R_1$, $R_2$, $R_a$, $R_b$ and $R_3$, respectively, and each incidence of $R_{12}$ and $R_{13}$ is independently selected from hydrogen, $C_1$-$C_6$ alkyl and $C_1$-$C_6$ alkoxy.

8. The compound of claim 1 wherein the compound is selected from:

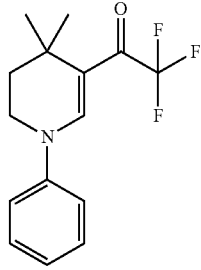

106

121
-continued
105
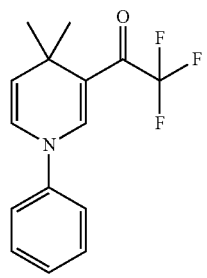
117
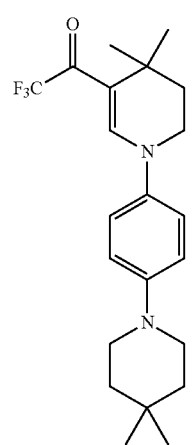
98
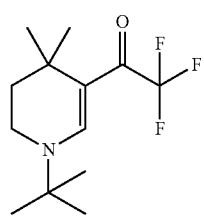
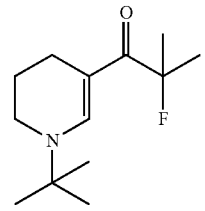
116
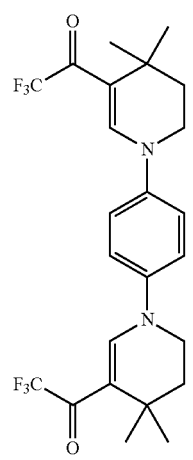
122
-continued
159
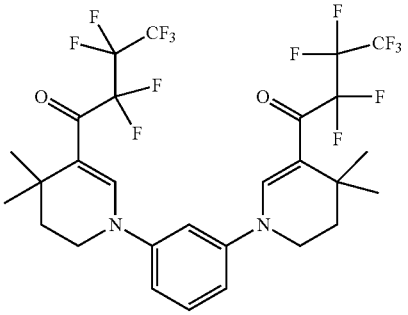
108
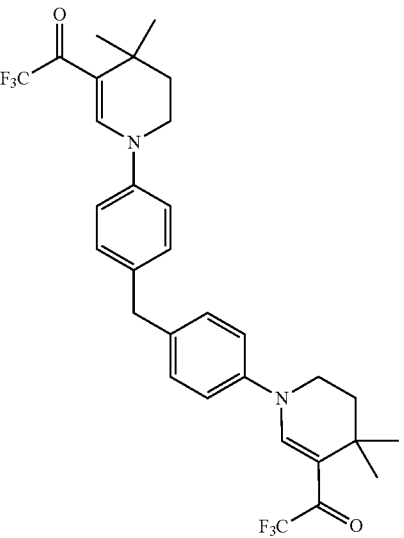
120
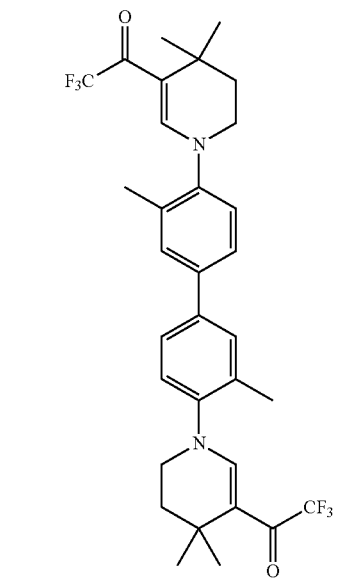

123
-continued
160
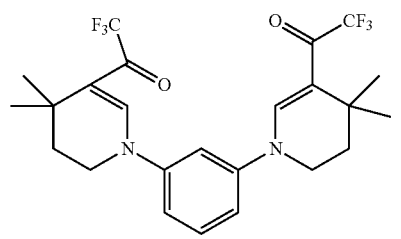
111
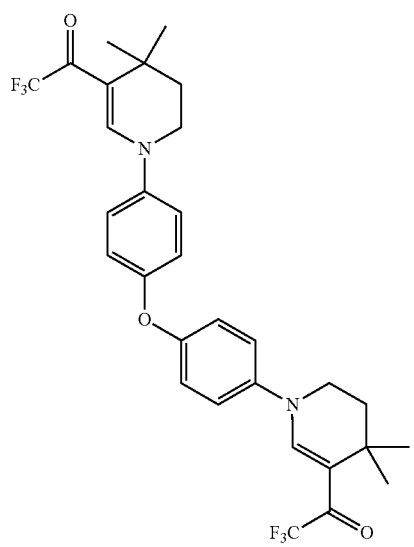
121
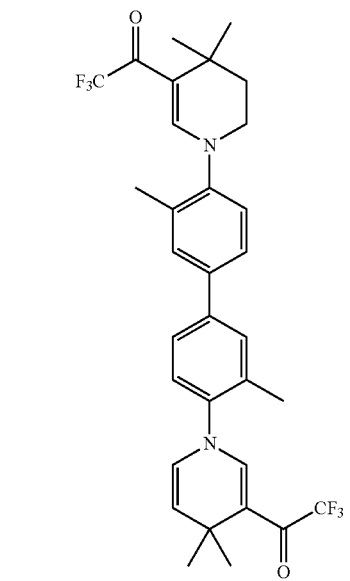
124
-continued
158
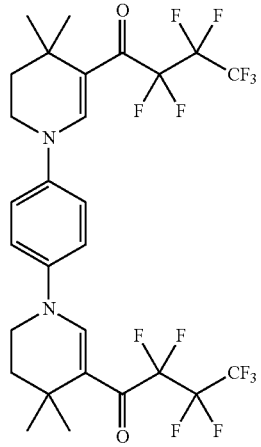
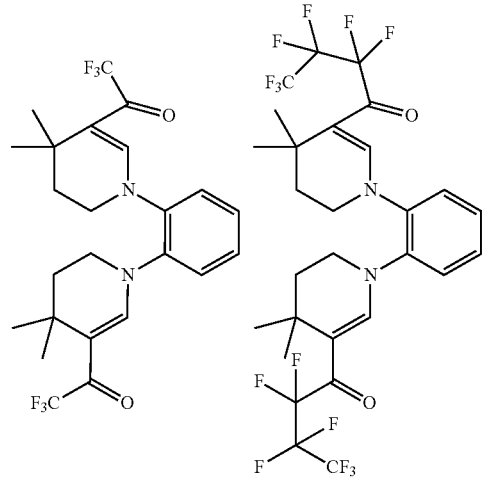
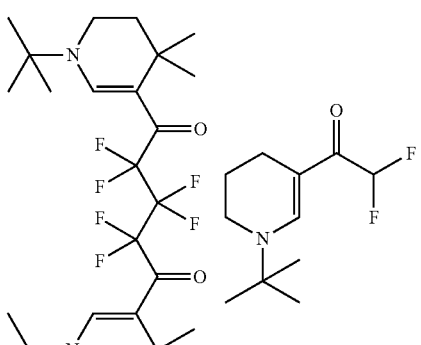
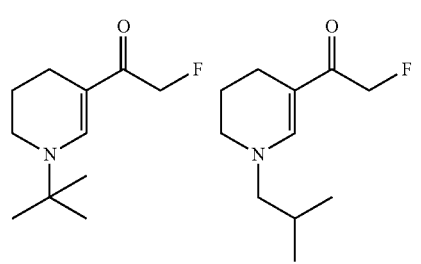

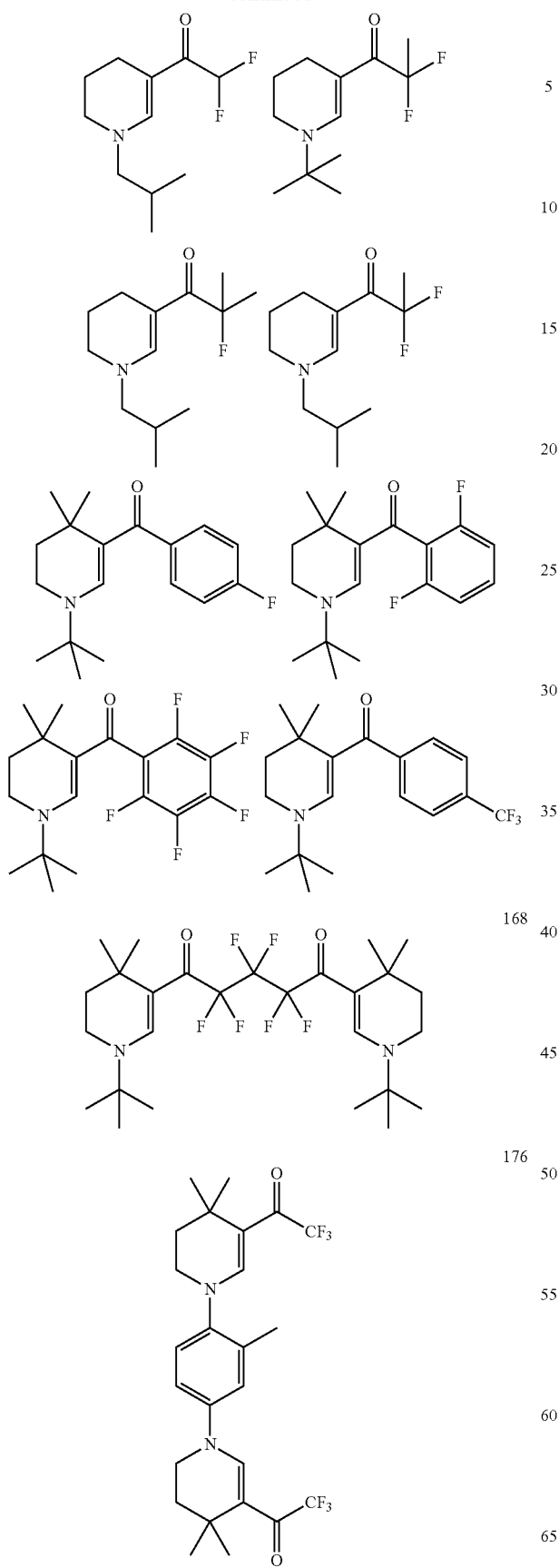
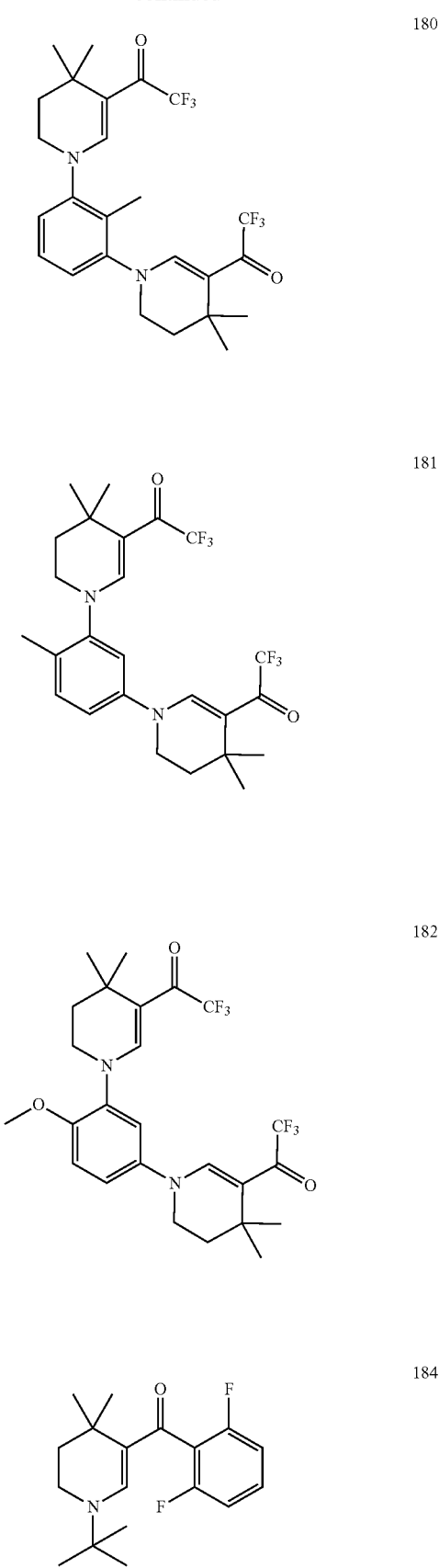

185 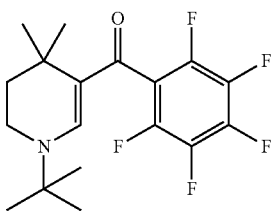
187 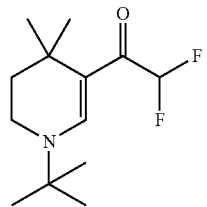
188 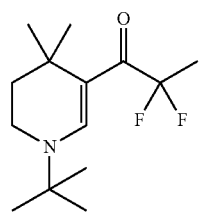
207 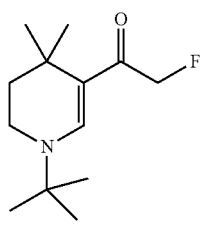
208 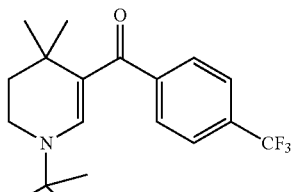
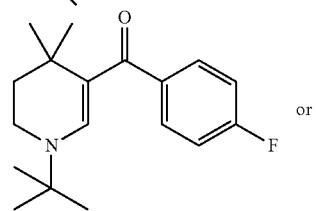 or
170 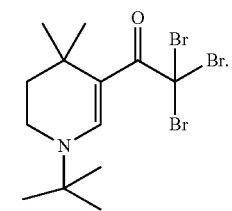
9. The compound of claim 1, wherein the dotted line is not a bond.
10. The compound of claim 1, wherein X is one carbon.
11. A composition comprising a compound of claim 1, or a salt thereof, and a suitable carrier.
12. A method of protecting a surface or tissue from UV rays including the step of applying a compound of claim 1, or a salt thereof, to the surface or tissue.
* * * * *